United States Patent
Kato et al.

(10) Patent No.: US 8,283,450 B2
(45) Date of Patent: Oct. 9, 2012

(54) HUMAN MONOCLONAL ANTIBODY HUMAN CD134 (OX40) AND METHODS OF MAKING AND USING SAME

(75) Inventors: Shinichiro Kato, Chiba (JP); Rachel Soloff Nugent, San Diego, CA (US); Hitoshi Yoshida, Gunma (JP); Michael Croft, San Diego, CA (US)

(73) Assignees: Kyowa Hakko Kirin Co., Ltd., Tokyo (JP); La Jolla Institute for Allergy and Immunology, La Jolla, CA (US)

( * ) Notice: Subject to any disclaimer, the term of this patent is extended or adjusted under 35 U.S.C. 154(b) by 441 days.

(21) Appl. No.: 12/087,436

(22) PCT Filed: Nov. 27, 2006

(86) PCT No.: PCT/US2006/045522
§ 371 (c)(1), (2), (4) Date: Dec. 31, 2009

(87) PCT Pub. No.: WO2007/062245
PCT Pub. Date: May 31, 2007

(65) Prior Publication Data
US 2010/0196359 A1  Aug. 5, 2010

Related U.S. Application Data

(60) Provisional application No. 60/739,659, filed on Nov. 25, 2005.

(51) Int. Cl.
*C12P 21/08* (2006.01)
(52) U.S. Cl. .............. 530/387.3; 530/388.1; 530/388.22
(58) Field of Classification Search .................. None
See application file for complete search history.

(56) References Cited

U.S. PATENT DOCUMENTS

| 6,312,700 B1 | 11/2001 | Weinberg |
| 2004/0136995 A1 | 7/2004 | Godfrey et al. |

FOREIGN PATENT DOCUMENTS

| JP | 2009-240311 | 10/2009 |
| WO | WO 95/12673 | 5/1995 |
| WO | 02/43478 A2 | 6/2002 |
| WO | 2004/019866 A2 | 3/2004 |
| WO | 2004/035607 A2 | 4/2004 |

OTHER PUBLICATIONS

Mariuzza et al. (Annu. Rev. Biophys. Biophys. Chem., 16: 139-159, 1987).*
Gussow et al (Methods in Enzymology 203: 99-121, 1991).*
Winkler et al (J. Imm., 265:4505-4514, 2000).*
Holt et al (TIB, 11:484-490, 2003).*
[Fundamental Immunology p. 242 (William E. Paul, M.D. ed., 3d ed; 1993)].*
Al-Shamkhani, A., et al., OX40 Is Differentially Expressed on Activated Rat and Mouse T Cells and is the Sole Receptor for the OX40 Ligand, Eur. J. Immunol., 26:1695-1699, 1996.
Sugamura, K., et al., Therapeutic Targeting of the Effector T-Cell Co-Stimulatory Molecule OX40, Nature, 4:420-431, 2004.
Taylor, L., et al., Identification of a Soluble OX40 Isoform: Development of a Specific and Quantitative Immunoassay, Journal of Immunological Methods, 255:67-72, 2001.
Weinberg, A.D., OX40: Targeted Immunotherapy—Implications for Tempering Autoimmunity and Enhancing Vaccines, Trends in Immunology, 23(2):102-109, 2002.
Higgins, L.M., et al., Regulation of T Cell Activation in Vitro and in Vitro by Targeting the OX40-OX40 Ligand Interaction: Amelioration of Ongoing Inflammatory Bowel Disease with an OX40-IgG Fusion Protein, But Not with an OX40 Ligand-IgG Fusion Protein, The Journal of Immunology, 1999, 162:486-493.
Imura, A., et al., The Human OX40/gp34 System Directly Mediates Adhesion of Activated T Cells to Vascular Endothelial Cells, J. Exp. Med., 1996, 183:2185-2195.
Kunitoni, A., et al., Vascular Endothelial Cells Provide T Cells With Costimulatory Signals Via The OX40/gp34 System, J. of Leukoc. Biol., 2000, 67:111-118.
Morris, N., et al., Development and Characterization of Recombinant Human Fc:OX4OL Fusion Protein Linked via a Coiled-Coil Trimerization Domain, Molecular Immunology,2007, 44:3112-3121.
Taylor, L., et al., In Vitro and In Vivo Activities of OX40 (CD134)-IgG Fusion Protein Isoforms with Different Levels of Immune-Effector Functions, J. Leukoc. Biol., 2002, 72:522-529.
Weinberg, A.D., et al., Blocking OX-40/OX-40 Ligand Interaction In Vitro and In Vivo Leads to Decreased T Cell Function and Amelioration of Experimental Allergic Encephalomyelitis, The Journal of Immunology, 1999, 162:1818-1826.

* cited by examiner

*Primary Examiner* — Anne Gussow
*Assistant Examiner* — Brad Duffy
(74) *Attorney, Agent, or Firm* — Pillsbury Winthrop Shaw Pittman, LLP

(57) ABSTRACT

The invention provides antibodies that specifically bind to OX40 (CD134), referred to as OX40 antibodies, anti-OX40 or anti-OX40 antibodies. Invention antibodies that specifically bind to OX40 include mammalian (human, primate, etc.), humanized and chimeric anti-OX40 antibodies. Invention antibodies and antibody subsequences (fragments) that specifically bind to OX40 include purified and isolated antibodies, as well as pharmaceutical formulations thereof, are useful in various methods including treatment, screening and detection methods.

11 Claims, 11 Drawing Sheets

Figure 7
A.
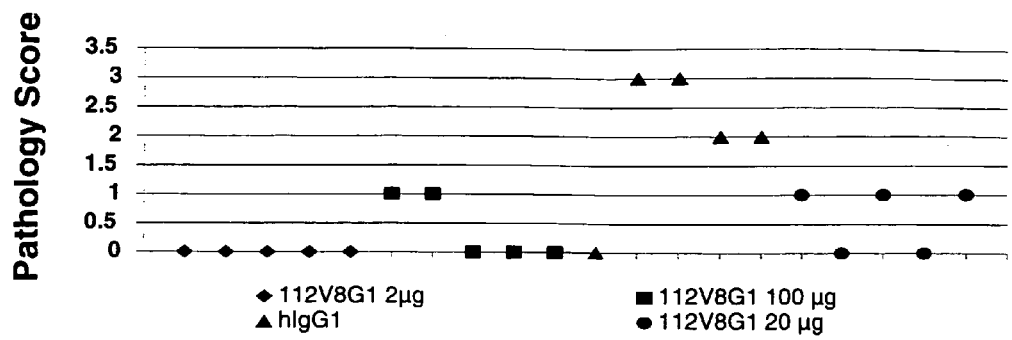
B.
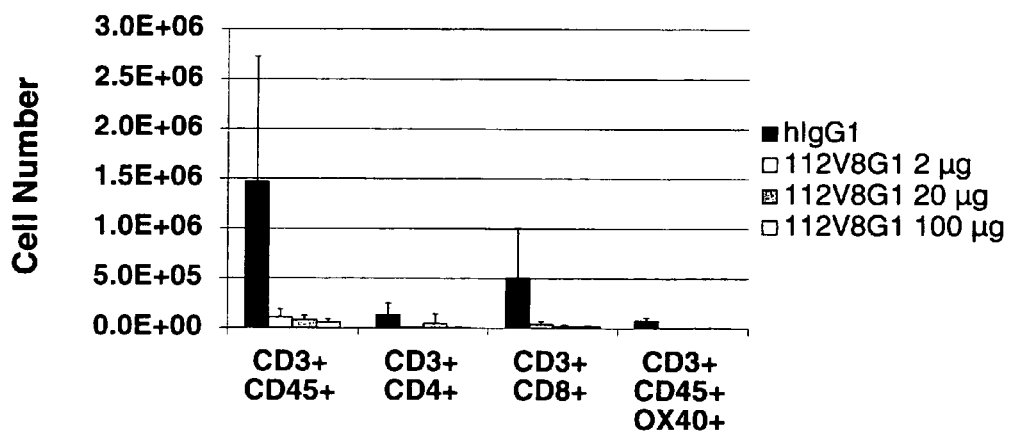
C.

Figure 9:
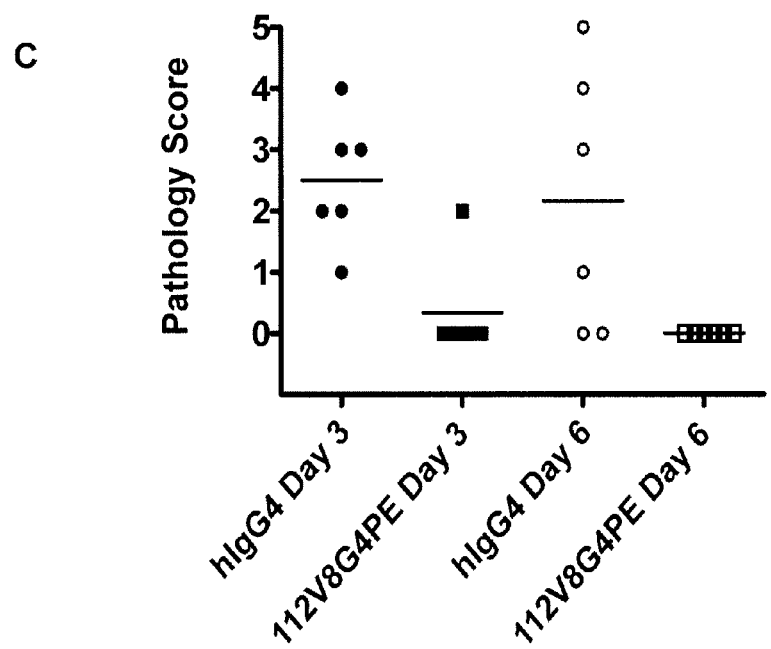

Figure 9
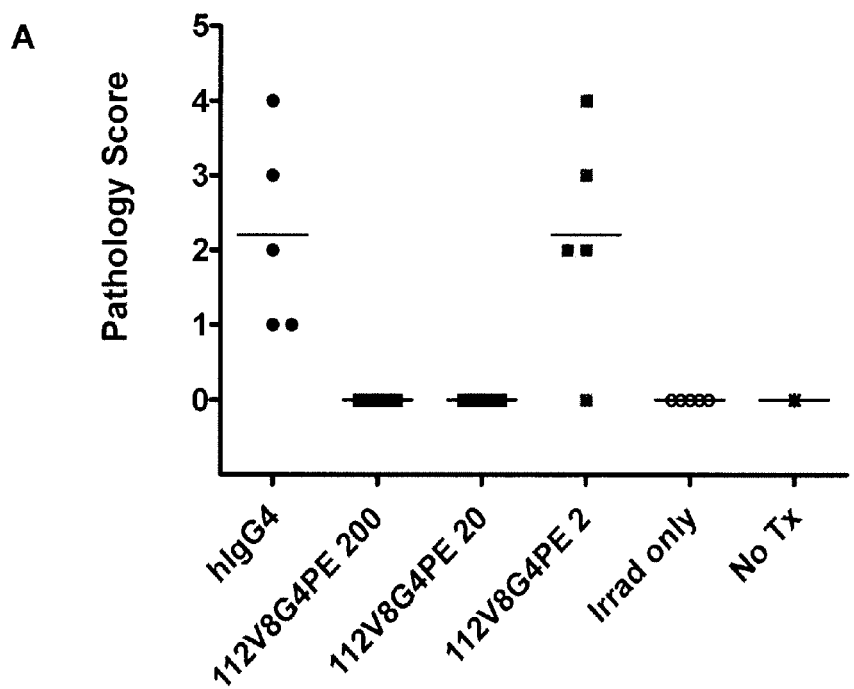
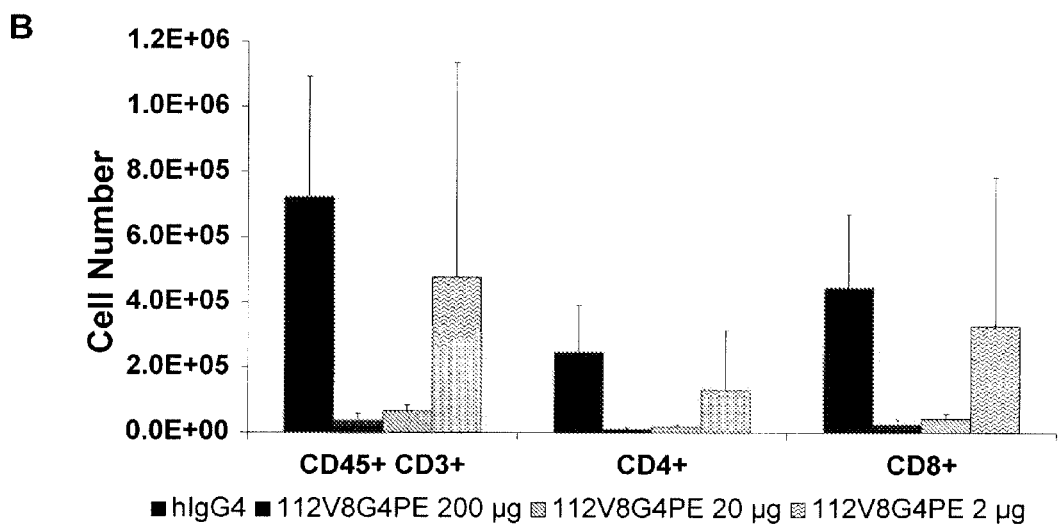

HUMAN MONOCLONAL ANTIBODY HUMAN CD134 (OX40) AND METHODS OF MAKING AND USING SAME

CROSS REFERENCE TO RELATED APPLICATIONS

This application claims priority to application Ser. No. 60/739,659, filed Nov. 25, 2005, and is expressly incorporated herein by reference.

INTRODUCTION

The immune system is composed of multiple cell types that work to protect the body from infectious diseases. This is dependent on the recognition of foreign antigens and the ability to distinguish self from non-self. In some cases the barrier between self and non-self is broken, leading to destruction of tissues by our own immune system. These autoimmune responses can lead to debilitating diseases such as diabetes, multiple sclerosis, and inflammatory bowel disease. One of the major mediators of these autoimmune responses is the T lymphocyte or T cell. Normally, T cells are tolerant to self-antigens, but in several autoimmune disorders this tolerance is lost and the T cells mount immune responses to healthy tissues. Removal of the autoimmune T cells or blockade of their activation or survival ameliorates the disease symptoms. However, this generic depletion of T cells or prevention of their activation leads to immunosuppression where patients become highly susceptible to infectious agents. New therapies are necessary that can specifically target the effector T cells and reduce only the auto-reactive T cells.

SUMMARY

The invention provides isolated or purified antibodies that specifically bind to an epitope in an amino acid sequence of OX40 extracellular domain (e.g., SEQ ID NO:50). Antibodies include human, humanized and chimeric antibodies that bind to mammalian (e.g., primate or human) OX40 sequence (e.g., SEQ ID NO:49) Antibodies also include those that have OX40 antagonist activity. Antibodies further include those that have OX40 agonist activity.

In particular embodiments, an antibody has OX40 antagonist activity and decreases or increases production of a cytokine or an interferon, survival or proliferation of activated, effector, memory or regulatory T cells, expression of an anti-apoptotic or pro-apoptotic protein. In particular non-limiting aspects, a cytokine is selected from IL-1, IL-2, IL-4, IL-5, IL-6, IL-9, IL-10, IL-14, IL-16, IL-17, IL-23, IL-26, TNF-α, interferon γ and GM-CSF; and an anti-apoptotic or pro-apoptotic protein is selected from Bcl-xL, Bcl-2, Bad and Bim.

In other particular embodiments, OX40 antibodies are produced by a hybridoma cell line denoted as 112F32 (ATCC No. PTA-7217, deposited Nov. 17, 2005), 112V8 (ATCC No. PTA-7219, deposited Nov. 17, 2005), 112Y55 (ATCC No. PTA-7220, deposited on Nov. 17, 2005), 112Y131 (ATCC No. PTA-7218, deposited on Nov. 17, 2005), and 112Z5 (ATCC No. PTA-7216, deposited on Nov. 17, 2005). In additional embodiments, OX40 antibodies bind to an amino acid sequence to which the antibody produced by a hybridoma cell line denoted as 112F32, 112V8, 112Y131, 112Y55, or 112Z5 binds; have an OX40 binding affinity within about 1-5000 fold of an antibody produced by a hybridoma cell line denoted as 112F32, 112V8, 112Y131, 112Y55, or 112Z5; have greater or less OX40 binding affinity than an antibody produced by a hybridoma cell line denoted as 112F32, 112V8, 112Y131, 112Y55, or 112Z5; have an OX40 binding affinity within about KD $10^{-6}$ M to about KD $10^{-13}$ M of an antibody produced by a hybridoma cell line denoted as 112F32, 112V8, 112Y131, 112Y55, or 112Z5; have the binding specificity of an antibody produced by a hybridoma cell line denoted as 112F32, 112V8, 112Y131, 112Y55, or 112Z5; competes with an antibody produced by a hybridoma cell line denoted as 112F32, 112V8, 112Y131, 112Y55, or 112Z5 for binding to OX40; inhibits or prevents binding of an antibody produced by a hybridoma cell line denoted as 112F32, 112V8, 112Y131, 112Y55, or 112Z5 to OX40, as determined in an ELISA assay (e.g., inhibits at least 50% of the binding of an antibody produced by a hybridoma cell line denoted as 112F32, 112V8, 112Y131, 112Y55, or 112Z5 to OX40); or binds to the same epitope as that of 112V8, 112Y55 and Y131, and inhibits or prevents OX40 binding to OX40 ligand (OX40L) (e.g., by 85% or more).

Antibodies additionally include those that specifically bind to OX40 expressed on cells. In particular embodiments, the antibody specifically binds OX40 expressed on non-T cells (e.g., natural killer cells, granulocytes, monocytes, B cells), or cell lines transfected with OX40 (e.g., CHO cells, L929 cells or HELA cells). In a particular aspect, the antibody specifically binds to activated human T cells, not resting T cells.

Antibodies include mature heavy or light chain variable region sequences, for example, as shown in SEQ ID NO:7-10 and SEQ ID NO:44-49. Antibodies also include modified and variant forms such as substitutions within or outside of a constant region, a complementary determining region (CDR) or a framework (FR) region antibody of a mature heavy or light chain variable region sequence, for example, as shown in SEQ ID NO:7-10 and SEQ ID NO:44-49. In particular aspects, substitutions include conservative amino acid substitutions. In additional particular aspects, substitutions include amino acid substitutions of 1-3, 3-5, 5-10 or more amino acid residues. In further particular aspects, an antibody has 80%-85%, 85%-90%, 90%-95%, 96%, 97%, 98%, 99%, or more identity to a sequence of mature heavy or light chain variable region sequence as shown in SEQ ID NO:7-10 and SEQ ID NO:44-49.

Antibodies also include subsequences of mature heavy or light chain variable region sequence, for example, as shown in SEQ ID NO:7-10 and SEQ ID NO:44-49. In particular aspects, a subsequence is selected from Fab, Fab', F(ab')$_2$, Fv, Fd, single-chain Fvs (scFv), disulfide-linked Fvs (sdFv) and $V_L$ or $V_H$.

Antibodies also include heterologous domains. In particular aspects, a heterologous domain includes a tag, detectable label or cytotoxic agent.

Modified and variant antibodies such as substitutions, subsequences and additions can retain a detectable activity of an OX40 antibody as set forth herein. In one embodiment, a modified antibody retains a detectable activity of an antibody produced by a hybridoma cell line denoted as 112F32, 112V8, 112Y131, 112Y55, or 112Z5. In another embodiment, a modified antibody modulates T cell expansion or survival, or numbers of activated, effector, memory or regulatory T cells, or depleting activated, effector, memory or regulatory T cells. In particular aspects, a modified antibody inhibits OX40 signaling or reduces or deletes numbers of auto-reactive T cells specific for a self-antigen (e.g., a self antigen such as myelin basic protein, myelin oligodendrocyte glycoprotein, proteolipid protein, collagen, synovial joint tissue antigens, insulin, glutamic acid decarboxylase, intestinal antigens, thyroid antigens, histone proteins, muscle antigens and skin antigens).

Antibodies also include those that compete with or do not compete with binding of antibody L106 to OX40. In a particular embodiment, an antibody does not inhibit or prevent the binding of antibody L106 to OX40, as determined in an ELISA assay.

Antibodies further include those that affect a function or activity of OX40. In particular embodiments, an antibody inhibits or prevents the binding of OX40 ligand to OX40; inhibits or prevents the binding of OX40 ligand to activated T cells; modulates OX40-mediated cell signaling (e.g., inhibits or prevents); modulates an OX40-mediated cell response; or OX40-mediated cell signaling (e.g., inhibits or prevents). In particular aspects, an OX40-mediated cell response comprises lymphocyte proliferation, cytokine expression, lymphocyte survival, activation of NF-kB, maintenance of PKB (Akt) activity, or upregulation of survivin. In further embodiments, an antibody induces lysis of EL4-human OX40 expressing cells or activated human T cells mediated by natural killer cells, macrophages or neutrophils, for example, the percent (%) specific cell lysis induced at 10 µg/ml of antibody is about 15 to 75%, 25 to 65%, or 30 to 60%, or 50-100%.

Antibodies further include those that have a function or activity in vivo. In particular embodiments, an antibody reduces, decreases or prevents a symptom of graft versus host disease in an acute or chronic xenograft host disease model, or causes a remission or regression of graft versus host disease in an acute or chronic xenograft host disease model (e.g., immunodeficient (SCID) mice that received human peripheral blood mononuclear cells (PBMC) after administration of anti-IL2Rbeta chain antibody and a sublethal dose of irradiation). In particular aspects, a symptom of graft versus host disease is weight loss, hair loss, skin rash, hematuria, hydroperitoneum, and inflammatory cell infiltrates in liver, intestinal tract, lung, skin, or death.

In additional embodiments, an antibody reduces, decreases or prevents inflammation in lung, skin, or bowel, or reduces, or decreases or prevents a symptom of an autoimmune disorder. In particular aspects, an antibody decreases or prevents a symptom of rheumatoid arthritis, multiple sclerosis, diabetes, Crohn's disease, inflammatory bowel disease, ulcerative colitis, celiac disease, psoriasis, proliferative lupus nephritis, granulomatous myopathy, or polymyositis.

Antibodies include monoclonal and polyclonal antibodies, any isotypes or subclasses thereof. In particular aspects, the antibody is an IgG (e.g., IgG1, IgG2, IgG3 or IgG4), IgA, IgM, IgE, or IgD isotype.

Antibodies can be included in pharmaceutical compositions. In one embodiment, an antibody includes a pharmaceutically acceptable carrier or excipient.

Antibodies can be encoded by nucleic acid sequences. In one embodiment, a nucleic acid encodes a sequence of mature heavy or light chain variable region sequence, for example, as shown in SEQ ID NO:7-10 and SEQ ID NO:44-49, or a subsequence thereof. In particular aspects, the nucleic acid sequences include SEQ ID NO:3-6 and SEQ ID NO:38-43, or sequences degenerate with respect to SEQ ID NO:3-6 and SEQ ID NO:38-43. In additional particular aspects, a nucleic acid encodes an amino acid sequence having one or more substituted, added or deleted amino acid residues of heavy or light chain variable region sequence as shown in SEQ ID NO:7-10 and SEQ ID NO:44-49. In further particular aspects, a nucleic acid that encodes an amino acid sequence having one or more substituted, added or deleted amino acid residues of heavy or light chain variable region sequence as shown in SEQ ID NO:7-10 and SEQ ID NO:44-49, has an activity of an antibody produced by a hybridoma cell line denoted as 112F32, 112V8, 112Y131, 112Y55, or 112Z5 (e.g., has binding affinity for an epitope of OX40 extracellular domain). In still further particular aspects, the nucleic acid sequence includes an expression control sequence or a vector.

Antibodies can be produced by host cells and isolated cells. In particular embodiments, a host or isolated cell is a hybridoma cell or CHO cell. In an additional particular embodiment, an isolated cell expresses an antibody having the binding specificity as antibody produced by a hybridoma cell line denoted as 112F32, 112V8, 112Y131, 112Y55, or 112Z5.

The invention provides kits. In particular embodiments, a kit includes an antibody produced by a hybridoma cell line denoted as 112F32, 112V8, 112Y131, 112Y55, or 112Z5, and instructions for administering the antibody to a subject in need of treatment with the antibody.

The invention provides in vivo methods, including treatment and therapeutic methods. In particular embodiments, a method for treating a chronic or acute immune disease or disorder, or a symptom of a chronic or acute immune disease or disorder in a subject in need of treatment includes administering to the subject an antibody or the pharmaceutical composition effective to treat the chronic or acute immune disease or disorder, or a symptom of the chronic or acute immune disease or disorder in the subject. In particular aspects, treatment results in alleviating or ameliorating one or more adverse symptoms or physical consequences associated with a chronic or acute immune disease or disorder.

In additional particular embodiments, a method for treating graft versus host disease includes administering to a subject in need of treatment an antibody or a pharmaceutical composition effective to treat graft versus host disease. In particular aspects, treatment reduces, decreases or prevents onset, frequency, duration or severity of one or more adverse symptoms or physical consequences associated with graft versus host disease (e.g., weight loss, hair loss, skin rash, hematuria, hydroperitoneum, inflammatory cell infiltrates in liver, intestinal tract, lung or death), results in a remission or regression of graft versus host disease, or results in preventing graft versus host disease. In additional aspects, a graft can include bone marrow, hematopoietic stem cells, peripheral blood stems cells or cord blood stem cells.

In further particular embodiments, a method for treating transplant rejection include administering to a subject in need of treatment an antibody or pharmaceutical composition effective to treat transplant rejection. In particular aspects, treatment reduces, decreases or prevents onset, frequency, duration or severity of one or more adverse symptoms or physical consequences associated with transplant rejection (e.g., an immune response against the transplant or transplant cell or tissue destruction), results in a remission or regression of transplant rejection, or results in preventing transplant rejection. In additional aspects, a transplant can include kidney, heart, lung, skin, liver or pancreas cells, tissue or organ.

In still further particular embodiments, a method for reducing, decreasing or preventing inflammation includes administering to a subject in need of treatment an antibody or pharmaceutical composition effective to reduce, decrease, or prevent onset, frequency, duration or severity of inflammation. In particular aspects, the inflammation is present in lung, joint, muscle, skin, central or peripheral nervous system, or bowel. In additional aspects, a treatment results in reducing onset, frequency, duration or severity of one or more adverse symptoms or physical consequences associated with inflammation.

In yet additional particular embodiments, a method for treating an autoimmune disorder includes administering to a subject in need of treatment an antibody or pharmaceutical composition effective to reduce, decrease or prevent onset, frequency, duration or severity of a symptom of an autoimmune disorder. In particular aspects, the autoimmune disorder includes rheumatoid arthritis, multiple sclerosis, diabetes, Crohn's disease, inflammatory bowel disease, ulcerative colitis, celiac disease, psoriasis, proliferative lupus nephritis, granulomatous myopathy, or polymyositis. In additional aspects, a treatment results in reducing, decreasing or preventing onset, frequency, duration or severity of one or more adverse symptoms or physical consequences associated with an autoimmune disorder.

Additional methods that can result in treatment or therapy, when practiced in vivo, include modulating OX40 activity or function. In particular embodiments, a method for inhibiting or preventing an OX40-mediated cell response includes administering to a subject in need of inhibiting or preventing an OX40-mediated cell response an antibody or pharmaceutical composition effective to inhibit or prevent an OX40-mediated cell response (e.g., lymphocyte proliferation, cytokine expression, or lymphocyte survival). In further embodiments, a method for inhibiting or blocking binding of an OX40 ligand to activated T cells includes administering to a subject in need of blocking, inhibiting or preventing binding of an OX40 ligand to activated T cells an antibody or pharmaceutical composition effective to inhibit or prevent binding of an OX40 ligand to activated T cells. In additional embodiments, a method for inhibiting or blocking binding of an OX40 ligand to OX40 includes administering to a subject in need of blocking, inhibiting or preventing binding of an OX40 ligand to OX40 an antibody or the pharmaceutical composition effective to inhibit or prevent binding of an OX40 ligand to OX40. In still further particular embodiments, a method for modulating OX40-mediated cell signaling includes administering to a subject in need of modulating OX40-mediated cell signaling an antibody or pharmaceutical composition effective to modulate OX40-mediated cell signaling. In yet additional particular embodiments, a method for reducing numbers of activated, effector, memory or regulatory T cells includes administering to a subject in need of reduced numbers of activated, effector, memory or regulatory T cells an amount of antibody sufficient to reduce numbers of activated, effector, memory or regulatory T cells.

In still additional particular embodiments, a method for decreasing the number of activated T cells in the blood, spleen, lymph nodes, intestines, liver, lung, or skin in an acute or chronic xenograft host disease model includes administering an amount of antibody to the acute or chronic xenograft host disease model sufficient to decrease the number of activated T cells in the blood, spleen, lymph nodes, intestines, liver, lung, or skin.

In even additional particular embodiments, a method for treating a disease or disorder caused by activated, effector, memory or regulatory T cells includes administering to a subject an amount of antibody sufficient to reduce, decrease or prevent progression of the disease or disorder caused by activated, effector, memory or regulatory T cells, or deplete activated, effector, memory or regulatory T cells. In particular aspects, the disease or disorder includes graft versus host disease, inflammation or an autoimmune disorder.

Subjects treatable in accordance with the invention include mammals (e.g., humans). In particular embodiments, a subject that is a candidate for or has been treated for a chronic or acute immune disease or disorder; a subject that is a candidate for or has been treated for graft versus host disease; a subject that is a candidate for or has been treated for transplant rejection; a subject that is a candidate for or has been treated for inflammation; or a subject that is a candidate for or has been treated for an autoimmune disorder; a that is subject is a candidate for or has been treated for an OX40-mediated cell response.

Methods of the invention that include administration or delivery of OX40 antibodies can be practiced by any acceptable method. In particular embodiments, an OX40 antibody is administered to a subject locally, regionally, or systemically.

The invention also provides methods for producing human OX40 antibodies that has OX40 antagonist activity. In one embodiment, a method includes administering a human OX40 extracellular domain conjugated with human Fc recombinant protein or activated human T cells to an animal capable of expressing human immunoglobulin (e.g., a transgenic mouse or transgenic cow); screening the animal for expression of human OX40 antibody; selecting an animal that produces a human OX40 antibody; isolating an antibody from the selected animal; and determining whether the human OX40 antibody has OX40 antagonist activity.

The invention further provides methods for producing human OX40 antibodies that inhibits or prevents OX40 binding to OX40 ligand (OX40L). In one embodiment, a method includes administering a human OX40 extracellular domain conjugated with human Fc recombinant protein or activated human T cells to an animal capable of expressing human immunoglobulin (e.g., a transgenic mouse or transgenic cow); screening the animal for expression of human OX40 antibody; selecting an animal that produces a human OX40 antibody; isolating an antibody from the selected animal; and determining whether the human OX40 antibody inhibits or prevents OX40 binding to OX40 ligand (OX40L).

The invention moreover provides non-human transgenic animals that express an OX40 antibody. In various embodiment, the expressed OX40 antibody is identical to an antibody produced by a hybridoma cell line denoted as 112F32, 112V8, 112Y131, 112Y55, or 112Z5; binds to an epitope in an amino acid sequence of OX40 extracellular domain to which an antibody produced by a hybridoma cell line denoted as 112F32, 112V8, 112Y131, 112Y55, or 112Z5; has an OX40 binding affinity within about 1-5000 fold of an antibody produced by a hybridoma cell line denoted as 112F32, 112V8, 112Y131, 112Y55, or 112Z5; has an OX40 binding affinity within about KD $10^{-6}$ M to about KD $10^{-12}$ M of an antibody produced by a hybridoma cell line denoted as 112F32, 112V8, 112Y131, 112Y55, or 112Z5; has the binding specificity of an antibody produced by a hybridoma cell line denoted as 112F32, 112V8, 112Y131, 112Y55, or 112Z5; or competes with an antibody produced by a hybridoma cell line denoted as 112F32, 112V8, 112Y131, 112Y55, or 112Z5 for binding to OX40.

DRAWING DESCRIPTIONS

FIGS. 1A-F: Flow cytometric analysis with human anti-human OX40 antibodies. A. Forward scatter versus side scatter profile of human CD4 T cells after three days of stimulation with PHA and IL2. B-F. Activated human T cells labeled with human anti-human OX40 antibodies or controls. The thick line represents staining on cells in the activated gate, while the thin line represents cells in the resting gate. Labeling of the activated cells by the isotype control IgG antibodies is shown by the dotted line in the histograms. B. 112F32, C. 112V8, D. 112Y55, E. 112Y131, and F. 112Z5.

Figure 1:
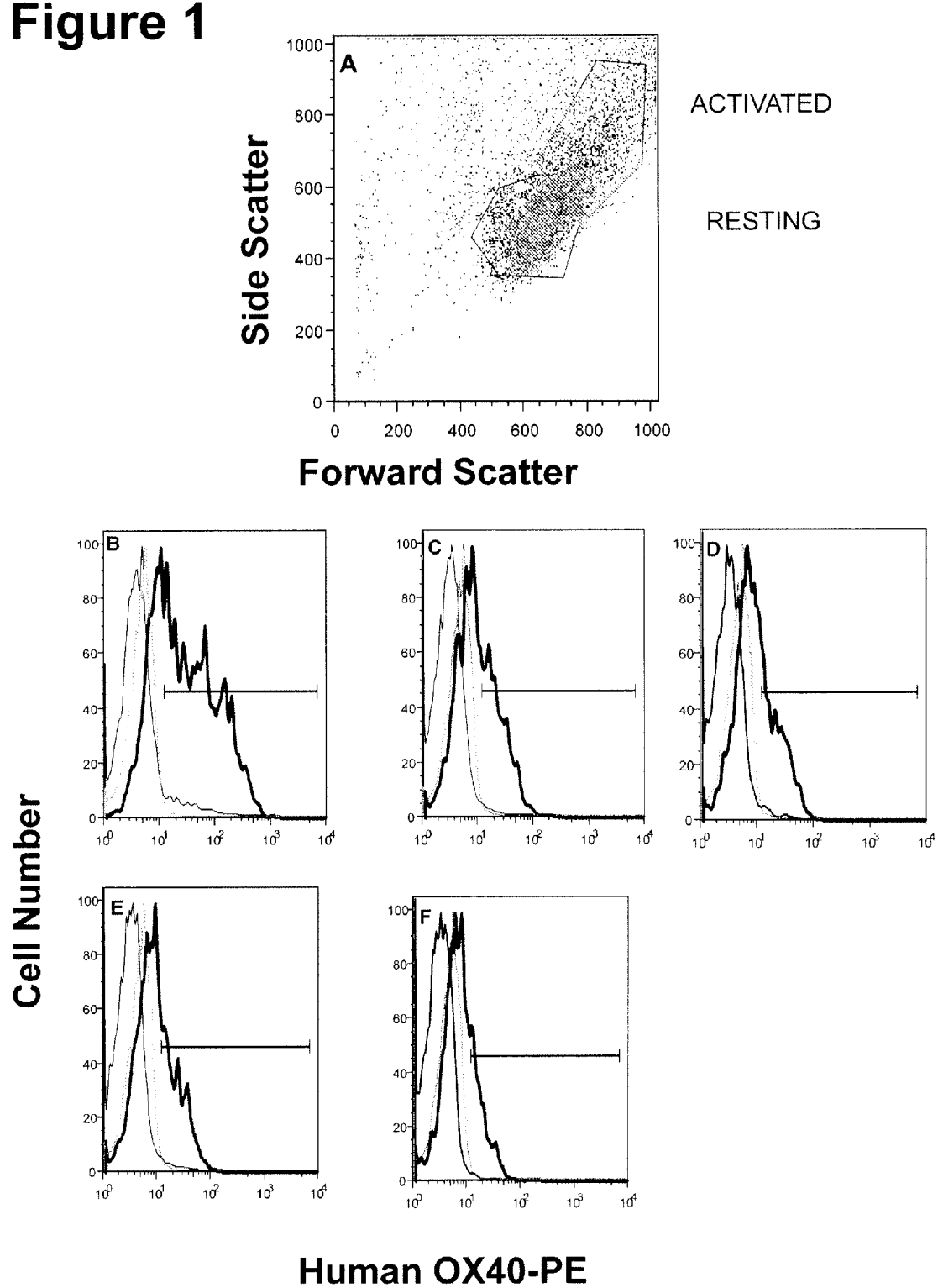
Figure 2:
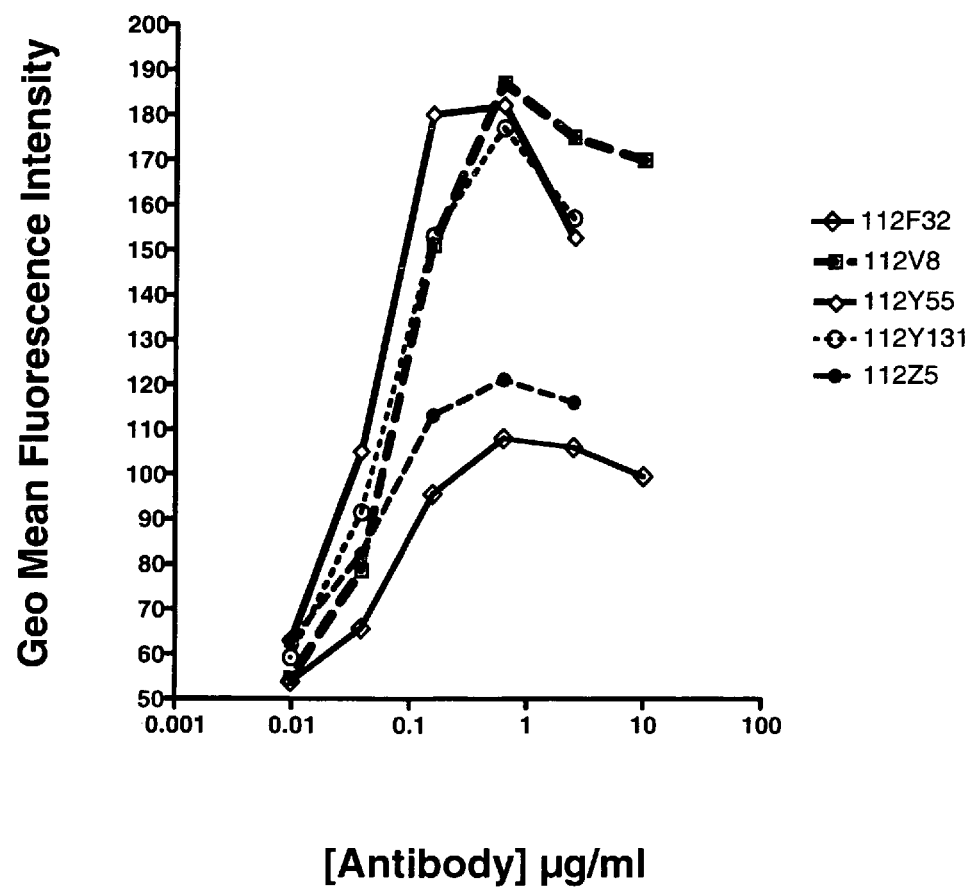

FIG. 2: Staining of activated human T cells by human anti-human OX40 monoclonal antibodies. The geometric mean fluorescence intensity data presented are derived from an activated T cell gate similar to the one depicted in FIG. 1A. These data were used to determine the KD and BMAX shown in Table 3.

Figure 3:
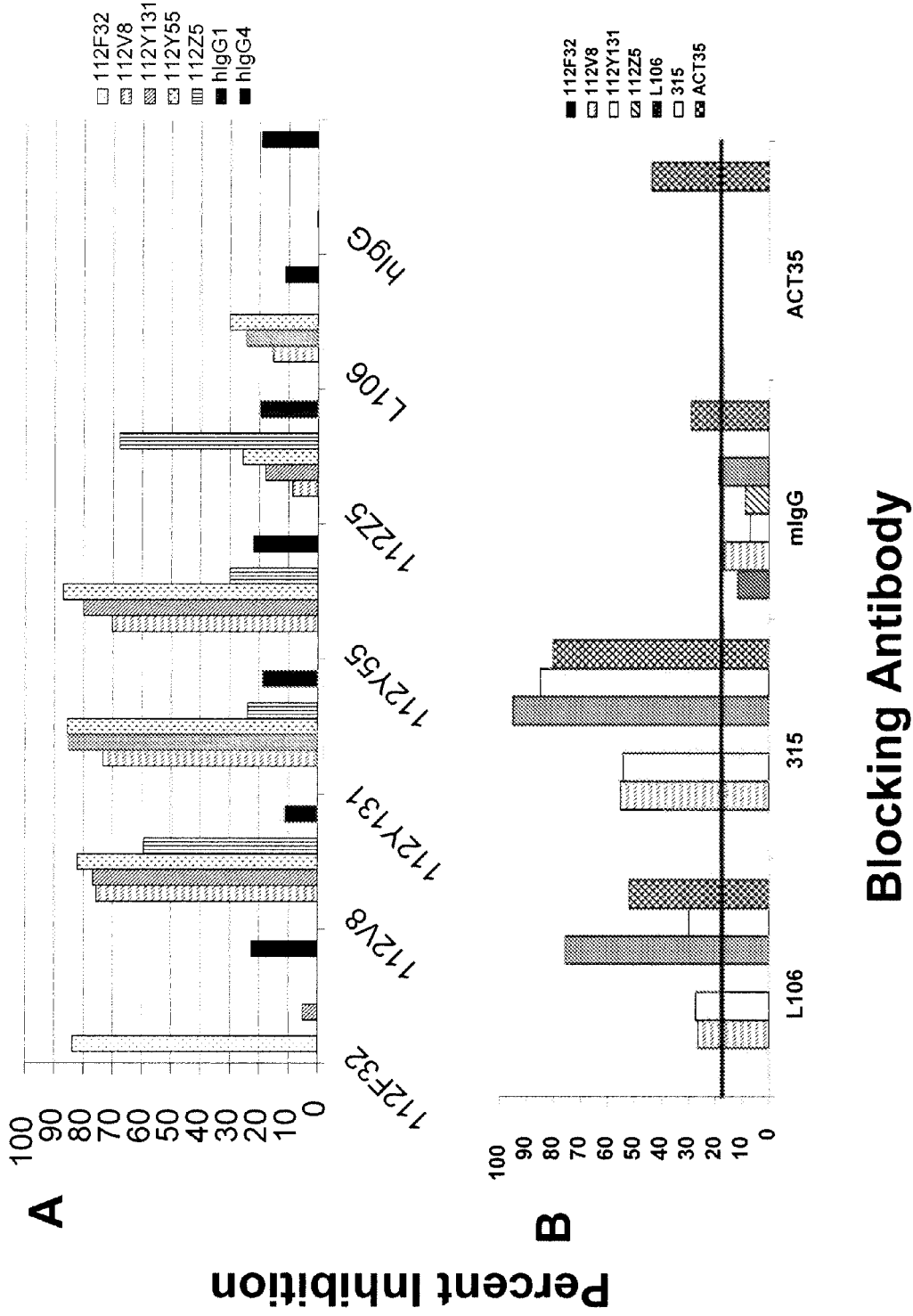

FIGS. 3A-B: Five OX40 antibodies compete for binding to OX40. A. Percent inhibition of bound hOX40:mFc to coated antibody detected with anti-mouse IgG-HRP. B. Percent inhibition of bound hOX40:hFc to mouse antibody detected with sheep anti-human IgG-HRP. Negative numbers not shown.

Figure 4:
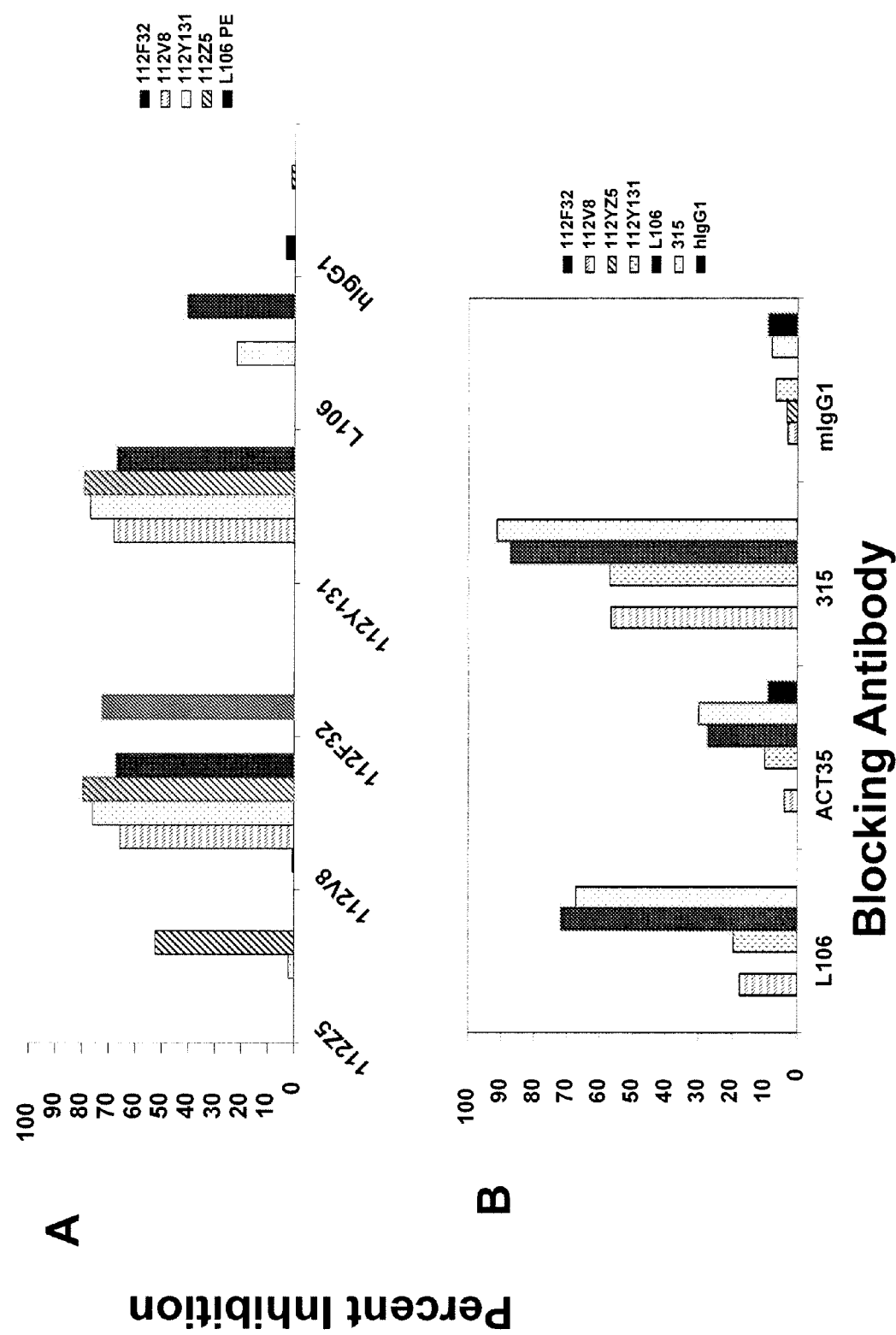

FIGS. 4A-B: Five OX40 antibodies compete for binding to OX40. A. Percent inhibition of activated T cells stained with blocking antibodies and biotinylated anti-OX40 antibodies detected with SA-PE. B. Percent inhibition of activated human T cells labeled with mouse anti-human OX40 antibodies and biotinylated anti-OX40 antibodies detected with SA-PE. Negative numbers not shown.

Figure 5:
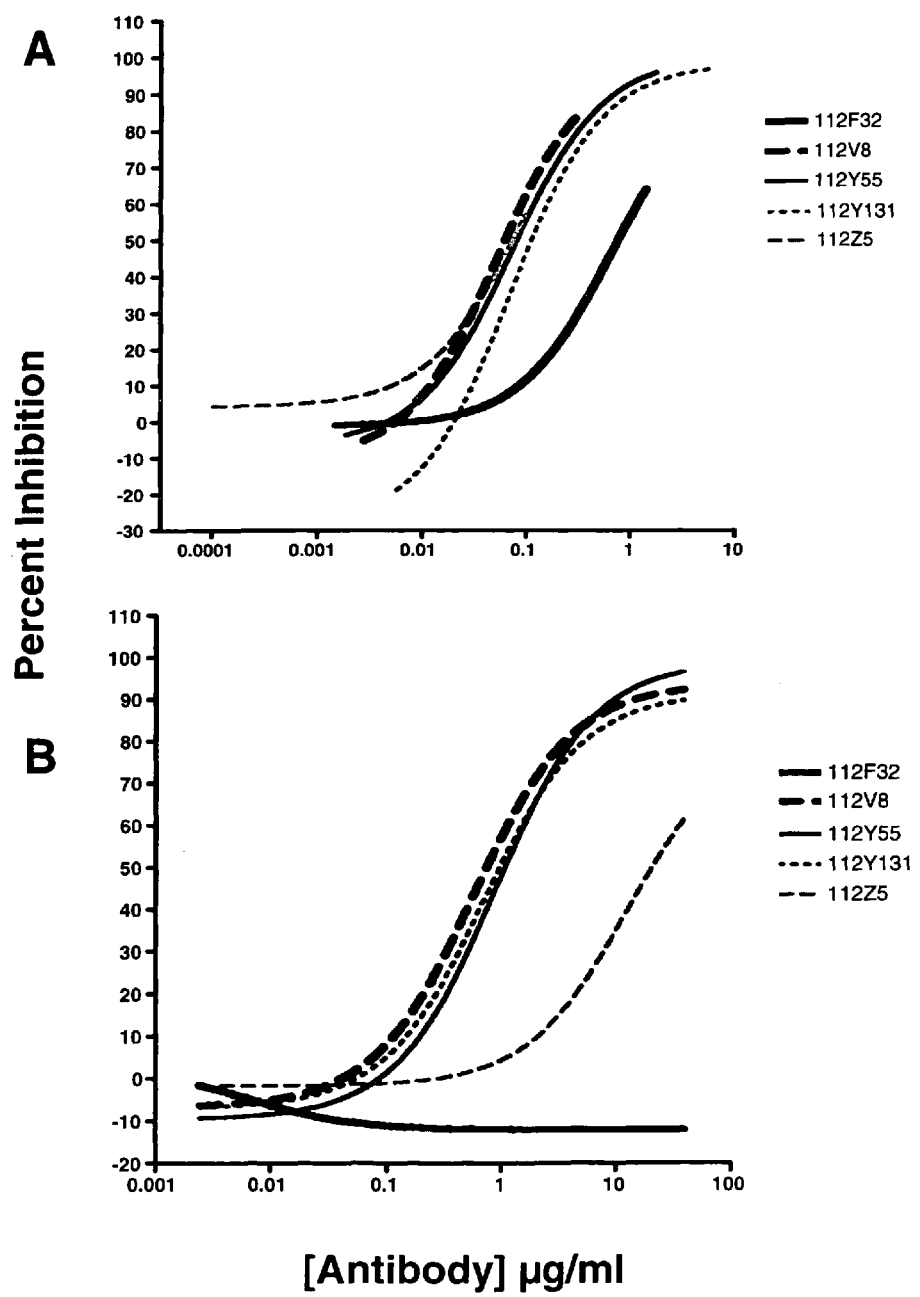

FIG. 5A-B: Blockade of OX40L binding to OX40 by human anti-human OX40 monoclonal antibodies measured by ELISA and flow cytometry. A. Percent inhibition of bound ligand was detected with anti-FLAG-HRP secondary antibody by ELISA. B. Percent inhibition of bound OX40L was detected with anti-FLAG-PE antibody by flow cytometry.

FIGS. 6A-C: Panels A-C represent three studies with three different donor pairs and depict the effect of anti-OX40 antibodies on T cell proliferation.

FIGS. 7A-C: Antibody 112V8G1 recombinant antibody ameliorated acute xenogenic graft versus host disease. A. Total gross pathology score. B. Single cell suspensions of the spleens analyzed by flow cytometry for the presence of human T cells. The average number of T cells and standard deviation of each population in each treatment group is shown. C. Human interferon gamma was measured in the serum of mice. The average amount of interferon gamma in pg/ml is shown for each group of mice plus the standard deviation.

Figure 8:
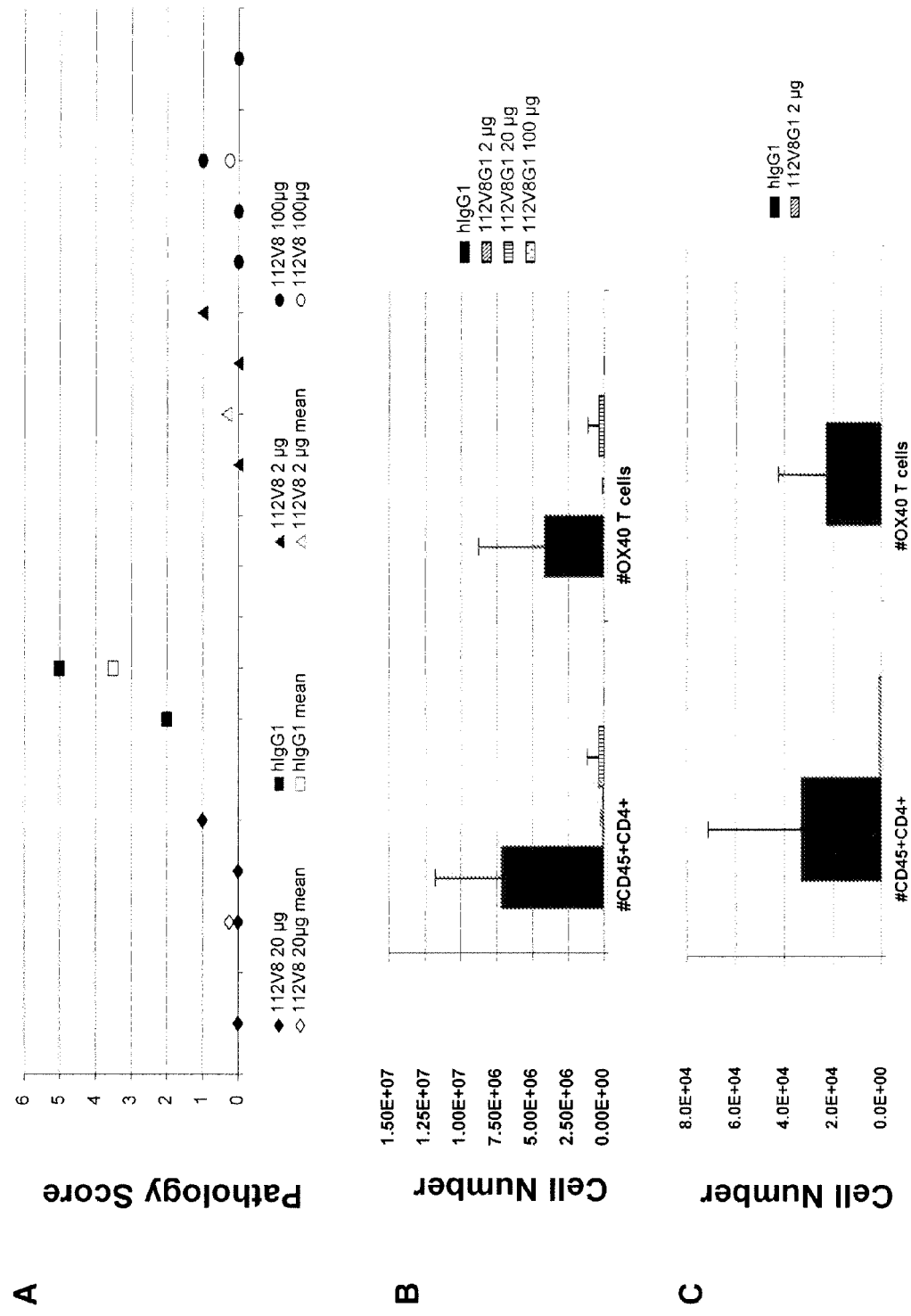

FIGS. 8A-C: Antibody 112V8G1 ameliorates chronic xenogenic graft versus host disease. A. Total gross pathology scores of individual mice. B. Average number of human T cells in the spleens of mice plus standard deviation as determined by flow cytometry. C. Average number of human T cells in the peripheral lymph nodes of SCID mice at day forty-eight post transfer of CD4 T cells.

FIGS. 9A-C: Antibody 112V8G4PE ameliorates acute xenogenic graft versus host disease when administered at day 0, 3, or 6. A. Total gross pathology scores of individual mice treated at day 0. B. Average number of human T cells in the spleens at day 12 from mice treated at day 0 plus standard deviation of the group. C. Total gross pathology scores of individual mice treated at day 3 or day 6.

Figure 10:
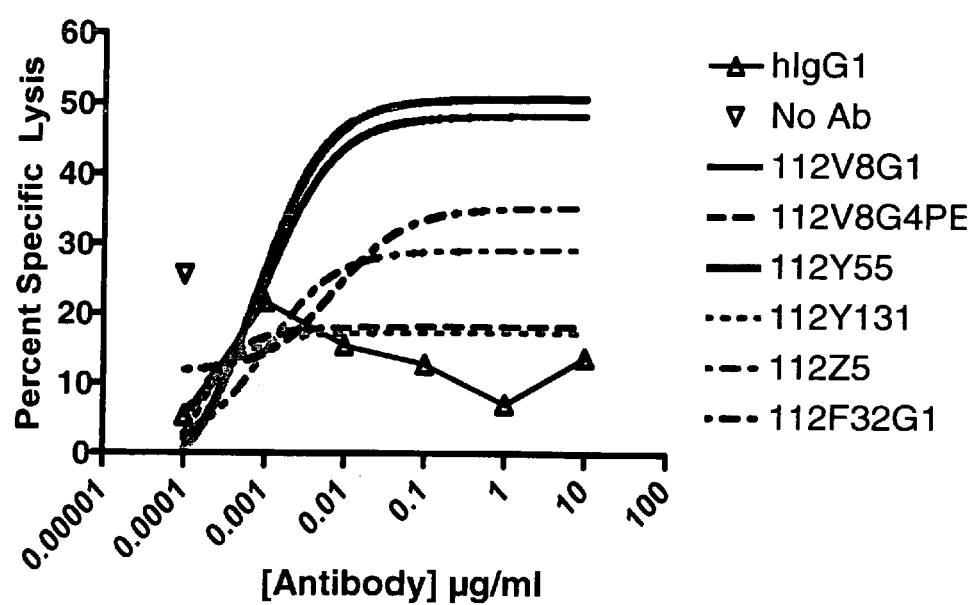

FIG. 10: Percent specific lysis by anti-human OX40 human IgG1 antibodies. Anti-human OX40 human IgG1 antibodies mediate ADCC of EL4-human OX40 targets.

DETAILED DESCRIPTION

The invention is based at least in part on antibodies that specifically bind to OX40 (CD134), which, for example, can be referred to as OX40 antibodies, anti-OX40 or anti-OX40 antibodies. Invention antibodies that specifically bind to OX40 include mammalian (human, primate, etc.), humanized and chimeric anti-OX40 antibodies. Invention antibodies and antibody subsequences (fragments) that specifically bind to OX40 include purified and isolated antibodies, as well as pharmaceutical formulations thereof.

OX40 is a 50 kilodalton (KDa) glycoprotein and a member of the tumor necrosis factor receptor superfamily (TNFRSF). The ligand for OX40, OX40L (also referred to as TNFSF4, CD252), has been reported to be expressed on endothelial cells, activated antigen presenting cells including macrophages, dendritic cells, B cells and natural killer cells. Although not wishing to be bound by theory, binding between CD40 on antigen presenting cells increases OX40L expression as can lipopolysaccharide (LPS). Expression of OX40 on T cells can be induced following signaling via the T cell antigen receptor. For example, OX40 is expressed on recently activated T cells at the site of inflammation. CD4 and CD8 T cells can upregulate OX40 under inflammatory conditions.

OX40 is also referred to as CD134, TNFRSF4, ACT35 and TXGP1L. OX40 includes mammalian (e.g., primate, human) forms of OX40. Invention OX40 antibodies therefore include antibodies that specifically bind to mammalian OX40 sequences such as human OX40, OX40 sequences, such as human OX40 include polymorphic variants. One non-limiting example of a full length human OX40 is a sequence set forth as:

(SEQ ID NO: 50)
MCVGARRLGRGPCAALLLLGLGLSTVTGLHCVGDTYPSNDRCCHE

CRPGNGMVSRCSRSQNTVCRPCGPGFYNDVVSSKPCKPCTWCNLRSGSER

KQLCTATQDTVCRCRAGTQPLDSYKPGVDCAPCPPGHFSPGDNQACKPWT

NCTLAGKHTLQPASNSSDAICEDRDPPATQPQETQGPPARPITVQPTEAW

PRTSQGPSTRPVEVPGGRAVAALGLGLVLGLLGPLAILLALYLLRRDQRL

PPDAHKPPGGGSFRTPIQEEQADAHSTLAKI.

OX40 antibodies, anti-OX40 and anti-OX40 antibodies refer to an antibodies that specifically bind to OX40. Specific binding is that which is selective for an epitope present in OX40. Specific binding can be distinguished from non-specific binding using assays known in the art (e.g., immunoprecipitation, ELISA, flow cytometry, Western blotting).

OX40 antibodies may bind to different proteins when all or a part of an antigenic epitope to which the antibody specifically binds is present on a different protein. Thus, depending on the extent of sequence or structural homology of the OX40 epitope, an OX40 antibody may specifically bind to another protein that has high sequence or structural homology to the OX40 epitope. Accordingly, OX40 antibodies may bind to different proteins when an epitope of sufficient sequence or structural homology is present on a different protein.

Invention OX40 antibodies include isolated and purified antibodies. Antibodies of the invention, including isolated or purified OX40 antibodies therefore do not include human beings.

The term "isolated" used as a modifier of a composition means that the composition is made by the hand of man or is separated from one or more other components in a naturally occurring in vivo environment, typically by one or more manipulative steps or processes. Generally, compositions so separated are substantially free of one or more materials with which they normally associate with in nature, for example, one or more protein, nucleic acid, lipid, carbohydrate, cell membrane. Thus, an isolated composition is separated from other biological components in the cell of the organism in which the composition naturally occurs, or from the artificial medium in which it is produced (e.g., synthetically or through cell culture). For example, an isolated OX40 antibody can be obtained from an animal in which the antibody is produced (e.g., a non-transgenic mammal or a transgenic mammal, such as a rodent (mouse) or an ungulate (bovine) animal) and is separated from other polypeptides and nucleic acid. Thus, serum containing the antibody obtained from the animal is considered isolated. The term "isolated" does not exclude alternative physical forms, for example, an isolated antibody could include antibody subsequences, chimeras, multimers, or derivatized forms.

The term "purified" used as a modifier of a composition refers to a composition free of most or substantially all of the materials with which it typically associates with in nature. Purified antibodies are typically removed from components normally present in the antibody milieu. Thus, an antibody supernatant separated from antibody producing hybridoma cell culture is considered purified. Purified therefore does not require absolute purity and is context specific. Furthermore, a "purified" composition can be combined with one or more other molecules. Thus, the term "purified" does not exclude combinations of compositions. Purity can be determined by any appropriate method, including, for example, UV spectroscopy, chromatography (e.g., HPLC, gas phase), gel electrophoresis (e.g., silver or coomassie staining) and sequence analysis (peptide and nucleic acid).

"Purified" proteins and nucleic acid include proteins and nucleic acids produced by standard purification methods. The term also includes proteins and nucleic acid produced by recombinant expression in a host cell as well as chemical synthesis. "Purified" can also refer to a composition in which the level of contaminants is below a level that is acceptable to a regulatory agency for administration to a human or non-human animal, for example, the Food and Drug administration (FDA).

Invention OX40 antibodies include antibodies that specifically bind to an epitope in an amino acid sequence of OX40 extracellular domain. In particular embodiments, exemplary OX40 antibodies specifically bind to three "epitopes" on OX40, as determined by a cross-blocking assay. An exemplary non-limiting human OX40 extracellular domain sequence is set forth as:

```
                                              (SEQ ID NO: 51)
MCVGARRLGR GPCAALLLLG LGLSTVTGLH CVDGTYPSND

RCCHECRPGN GMVSRCSRSQ NTVCRPCGPG FYNDVVSSKP

CKPCTWCNLR SGSERKQLCT ATQDTVCRCR AGTQPLDSYK

PGVDCAPCPP GHFSPGDNQA CKPWTNCTLA GKHTLQPASN

SSDAICEDRD PPATQPQETQ GPPARPITVQ PTEAWPRTSQ GPS.
```

Peptide epitopes typically are short amino acid sequences, e.g. about five to 15 amino acids in length. Techniques for identifying epitopes are known in the art and are described, for example, in U.S. Pat. No. 4,708,871. Briefly, a set of overlapping oligopeptides derived from OX40 polypeptide may be synthesized and bound to a solid phase array of pins, with a unique oligopeptide on each pin. The array of pins may comprise a 96-well microtiter plate, permitting one to assay 96 oligopeptides simultaneously. Discontinuous epitopes may be identified similarly using highly overlapping peptide scans of different lengths (e.g., 6-mers to 15-mers) immobilized at high density on a membrane support. High antibody concentrations are used and binding is detected by indirect immunodetection. If multiple binding sequences are identified and are separated by intervening sequences but the individual peptides are not recognized, then a discontinuous epitope has been identified. The separated sequences would be expected to form a continuous area on the surface of the target protein and represent a conformational epitope (Reineke, et al. *Protein Sci.* 7:951 (1998). Alternatively, phage display peptide library kits (New England BioLabs) are commercially available for epitope mapping. These and other methods can be used to determine binding affinity for every possible subset of consecutive amino acids in order to identify the epitope that a particular antibody binds. Epitopes may also be identified by inference when epitope length peptide sequences are used to immunize animals from which are obtained antibodies that bind to the peptide sequence. Continuous epitopes can also be predicted using computer programs such as BEPITOPE (Odorico et al., *J. Mol. Recognit.* 16:20 (2003)).

Antibodies of the invention are monoclonal or polyclonal immunoglobulin molecules that belong to any antibody class such as IgM, IgG, IgA, IgE, IgD, and any subclass thereof. Exemplary subclasses for IgG are $IgG_1$, $IgG_2$, $IgG_3$ and $IgG_4$. A "monoclonal" antibody refers to an antibody that is based upon, obtained from or derived from a single clone, including any eukaryotic, prokaryotic, or phage clone. A "monoclonal" antibody is therefore defined structurally, and not the method by which it is produced.

Particular exemplary antibodies that specifically bind to OX40 are denoted as 112F32 (ATCC No. PTA-7217, deposited Nov. 17, 2005), 112V8 (ATCC No. PTA-7219, deposited Nov. 17, 2005), 112Y55 (ATCC No. PTA-7220, deposited on Nov. 17, 2005), 112Y131 (ATCC No. PTA-7218, deposited on Nov. 17, 2005), and 112Z5 (ATCC No. PTA-7216, deposited on Nov. 17, 2005), which are human monoclonal anti-human OX40 antibodies (human antibodies that bind to human OX40). Exemplary invention OX40 antibodies 112F32, 112V8, 112Y55, 112Y131, and 112Z5 have mature heavy or light chain variable region sequences as shown in SEQ ID NO:7-10 and SEQ ID NO:44-49. The designation of 112F32, 112V8, 112Y55, 112Y131, and 112Z5 can refer to either the antibody or a cell line (e.g., hybridoma, CHO cell or other host cell) that produces the OX40 antibody.

Exemplary invention human anti-human OX40 antibodies were produced using trans-chromosomic mice (KM Mice™) (WO 02/43478, WO 02/092812, and Ishida, et al., IBC's 11th Antibody Engineering Meeting. Abstract (2000)) immunized with various forms of soluble recombinant human OX40 (OX40-hIgG1), fusion protein (hOX40:hFc) or activated human T cells that express OX40. Exemplary antibodies were identified that specifically labeled activated human T cells and not resting T cells. Exemplary antibodies delectably stained human OX40 stably transfected cell lines, EL4-OX40 and CHO-OX40, and not non-transformed parental cell lines, indicating that the antibodies specifically bind to human OX40. Exemplary antibodies also bind to rhesus macaque OX40 and cynomolgus macaque OX40, but do not detectably bind to murine OX40.

Antibodies of the invention can have kappa or lambda light chain sequences, either full length as in naturally occurring antibodies, mixtures thereof (i.e., fusions of kappa and lambda chain sequences), and subsequences/fragments thereof. Naturally occurring antibody molecules contain two kappa or two lambda light chains.

Invention OX40 antibodies also include, for example, antibodies that specifically bind to an amino acid sequence to which the antibody produced by a hybridoma cell line denoted as 112F32 (ATCC No. PTA-7217, deposited Nov. 17, 2005), 112V8 (ATCC No. PTA-7219, deposited Nov. 17, 2005), 112Y131 (ATCC No. PTA-7218, deposited on Nov. 17, 2005), 112Y55 (ATCC No. PTA-7220, deposited on Nov. 17, 2005), or 112Z5 (ATCC No. PTA-7216, deposited on Nov. 17, 2005) binds. Invention OX40 antibodies further include, for example, antibodies that specifically bind to an OX40 extracellular domain to which an antibody produced by a hybridoma cell line denoted as 112F32, 112V8, 112Y131, 112Y55, or 112Z5 binds. Invention OX40 antibodies additionally include, for example, antibodies that have the binding specificity of an antibody produced by a hybridoma cell line denoted as 112F32, 112V8, 112Y131, 112Y55, or 112Z5. Such OX40 antibodies typically exhibit partial or complete blocking, reduction or inhibition of 112F32, 112V8, 112Y131, 112Y55, or 112Z5 antibody binding to OX40.

OX40 antibodies that specifically bind to an amino acid sequence to which the antibody produced by a hybridoma cell line denoted as 112F32, 112V8, 112Y131, 112Y55, or 112Z5 binds, and antibodies having the binding specificity of 112F32, 112V8, 112Y131, 112Y55, or 112Z5 antibody can be identified using competition binding assays. Antibodies can be selected based upon an ability to compete for binding of 112F32, 112V8, 112Y131, 112Y55, or 112Z5 antibody to OX40. The ability of an antibody to compete for binding of 112F32, 112V8, 112Y131, 112Y55, or 112Z5 antibody to OX40, or to inhibit, reduce, decrease, prevent or block binding of 112F32, 112V8, 112Y131, 112Y55, or 112Z5 antibody to OX40, can be determined by various assays know in the art, including enzyme linked immunosorbent assay (ELISA). In particular aspects, an invention antibody inhibits or prevents binding of an antibody produced by a hybridoma cell line denoted as 112F32, 112V8, 112Y131, 112Y55, or 112Z5 to OX40, as determined in an ELISA assay. In further aspects, an invention antibody inhibits at least 50% of the binding of an antibody produced by a hybridoma cell line denoted as 112F32, 112V8, 112Y131, 112Y55, or 112Z5 to OX40, as determined in an ELISA assay.

Invention OX40 antibodies also include antibodies that specifically bind OX40 and that do not prevent or block binding of mouse anti-human OX40 antibody L106 (Becton Dickinson, catalog number 340420) to OX40. Further included are OX40 antibodies that specifically bind OX40 and that do not inhibit, reduce or decrease binding of antibody L106 to OX40. Antibody L106 is described, for example, in U.S. Pat. No. 6,277,962, WO 95/12673 and Schlossman et al., eds. (*Leukocyte Typing V: White Cell Differentiation Antigens*, Oxford: Oxford University Press (1995) pp 1157-60)

Invention OX40 antibodies include antibodies that specifically bind to OX40 having greater or less affinity for OX40 than antibody produced by a hybridoma cell line denoted as 112F32, 112V8, 112Y131, 112Y55, or 112Z5. For example, antibodies having an OX40 binding affinity within about 1-10,000 fold (e.g., 2-5, 5-10, 10-100, 100-1000 or 1000-10,000-fold greater or less affinity, or any numerical value or range within or encompassing such values) of an antibody produced by a hybridoma cell line denoted as 112F32, 112V8, 112Y131, 112Y55, or 112Z5 are provided. Invention OX40 antibodies therefore also include antibodies having greater or less OX40 binding affinity than antibody produced by a hybridoma cell line denoted as 112F32, 112V8, 112Y131, 112Y55, or 112Z5. In particular embodiments, an invention OX40 antibody has an OX40 binding affinity within about KD $10^{-6}$ M to about KD $10^{-13}$ M, or any numerical value or range within or encompassing such values, of an antibody produced by a hybridoma cell line denoted as 112F32, 112V8, 112Y131, 112Y55, or 112Z5.

Binding affinity can be determined by association ($K_a$) and dissociation ($K_d$) rate. Equilibrium affinity constant, KD, is the ratio of $K_a/K_d$. Association ($K_a$) and dissociation ($K_d$) rates can be measured using surface plasmon resonance (SPR) (Rich and Myszka, *Curr. Opin. Biotechnol.* 11:54 (2000); Englebienne, *Analyst.* 123:1599 (1998)). Instrumentation and methods for real time detection and monitoring of binding rates are known and are commercially available (BiaCore 2000, Biacore AB, Upsala, Sweden; and Malmqvist, *Biochem. Soc. Trans.* 27:335 (1999)). KD values can be defined as the OX40 antibody concentration required to saturate one half (50%) of the binding sites on OX40.

Invention OX40 antibodies include antibodies capable of binding to OX40 present on one or more cells in vivo, in primary cell isolates, passaged cells, cultured cells and immortalized cells. Specific non-limiting cell types that can express OX40 include activated and other T cells (e.g., activated, effector, memory or regulatory T cells) and non-T cells. Examples of non-T cells include natural killer (NK) cells, granulocytes (neutrophils), monocytes and B cells. Cells that do not naturally express OX40 can be made to express OX40, for example, by transfecting or transforming cells with an OX40 encoding nucleic acid. OX40 antibodies capable of binding to OX40 can bind to one or more transfected or transformed cells that express or produce OX40.

Invention antibodies include antibodies that bind to OX40 and modulate an OX40 function or activity in vivo or in vitro (e.g. in a subject). As used herein, the term "modulate" and grammatical variations thereof, when used in reference to an OX40 activity or function, means that the OX40 activity or function is detectably affected, altered or changed. Thus, an OX40 antibody that modulates an OX40 activity or function is an antibody that detectably affects, alters or changes one or more OX40 activities or functions, which can include, for example, binding of OX40 to OX40 ligand, OX40 mediated signaling or an OX40-mediated or OX40-modulatable cell response, or another OX40 activity or function as set forth herein or otherwise known or knowable.

Various non-limiting OX40 activities and functions that can be modulated include, for example, OX40-mediated signaling or an OX40-mediated or OX40-modulatable cell response, cell proliferation or expansion (e.g., lymphocytes such as activated, effector, memory or regulatory T cells), cell survival or apoptosis (e.g., lymphocytes such as activated, effector, memory or regulatory T cells), cytokine (e.g., Th1, Th2 and non Th1/Th2 cytokines) and interferon expression or production, anti-apoptotic or pro-apoptotic protein expression or production, and treatment, prevention or amelioration of disorders, diseases, physiological conditions, pathologies and symptoms thereof. Specific cytokines modulated include but are not limited to IL-1, IL-2, IL-4, IL-5, IL-6, IL-9, IL-10, IL-14, IL-16, IL-17, IL-23, IL-26, TNF-α, interferon γ, and GM-CSF (in vivo or vitro). Specific anti-apoptotic or pro-apoptotic protein expression include but are not limited to Bcl-xL, Bcl-2, Bad and Bim. Other non-limiting activities or functions of OX40 that can be modulated included, for example, activation of NF-kB, maintenance of PKB (Akt) activity, and upregulation of survivin (Ambrosini et al., *Nat. Med.* 3:917 (1997); and Song et al., *Immunity* 22:621 (2005)).

Exemplary antibodies as set forth herein therefore include antibodies that modulate one or more OX40-mediated signaling or an OX40-mediated or induced cell response, cell proliferation (e.g., activated, effector, memory or regulatory T cells), cell survival or apoptosis (e.g., activated, effector, memory or regulatory T cells), cytokine (e.g., Th1, Th2 and other non Th1/Th2 cytokines, e.g., IL-17, IL-23 and IL-26) and interferon expression or production such as Th1, Th2, non Th1/Th2, IL-1, IL-2, IL-4, IL-5, IL-6, IL-9, IL-10, IL-14, IL-16, IL-17, IL-23, IL-26, TNF-α, interferon γ, and GM-CSF (in vivo or vitro), anti-apoptotic or pro-apoptotic protein expression (e.g., Bcl-xL, Bcl-2, Bad or Bim), and treatment, prevention or amelioration of disorders, diseases, pathologies and symptoms thereof. In particular aspects, invention antibodies modulate T cell expansion or survival, modulate numbers of activated, effector, memory or regulatory T cells, or deplete activated, effector, memory or regulatory T cells. In further particular aspects, invention antibodies reduce or delete numbers of auto-reactive T cells specific for a self-antigen (e.g., myelin basic protein (MBP), myelin oligodendrocyte glycoprotein (MOG), proteolipid protein (PLP), collagen, synovial joint tissue antigens, insulin, glutamic acid decarboxylase, intestinal antigens, thyroid antigens, histone proteins, muscle antigens or skin antigens).

The term "antagonist" and grammatical variations thereof used in reference to an OX40 antibody, means an OX40 antibody that reduces, decreases, inhibits, retards, prevents or blocks OX40 binding to OX40 ligand, or reduces, decreases, inhibits, retards, prevents or blocks an OX40 activity or function. The term "agonist" and grammatical variations thereof used in reference to an OX40 antibody, means an OX40 antibody that stimulates, increases, enhances, promotes or induces OX40 binding to OX40 ligand, or stimulates, increases, enhances, promotes or induces an activity or function induced by OX40. Invention OX40 antibodies therefore include antagonist and agonist antibodies.

Invention OX40 antagonist antibodies, block, reduce, decrease, inhibit or prevent one or more activities or functions of OX40 in vitro or in vivo, for example. In particular embodiments, OX40 antibodies that can block, reduce, decrease, inhibit or prevent OX40 ligand (OX40L) binding to OX40 (CD134) in the soluble form or OX40 expressed on the surface of activated T cells are provided. In additional embodiments, an OX40 antibody induces lysis of EL4-human OX40 expressing cells or activated human T cells in the presence of lytic effector cells (e.g., natural killer cells, macrophages or neutrophils). In particular aspects, the percent (%) specific cell lysis induced at 10 μg/ml of antibody is between about 15 to 75%, 25 to 65%, or 30 to 60%, and can be as high as 100%, depending upon background levels in the studies. In addition, incubation of exemplary OX40 antibodies with human peripheral blood mononuclear cells (PBMC) co-cultured with PBMC from an allogeneic donor reduced cell proliferation by inhibiting allo-reactive CD4 and/or CD8 T cells.

Invention OX40 antibodies include modified forms, such as substitutions (e.g., amino acid substitutions), additions and deletions (e.g., subsequences or fragments), which can be referred to as "variants." Such modified antibody forms and variants retain at least partial function or activity of a reference OX40 antibody, for example, an OX40 antibody denoted as 112F32, 112V8, 112Y55, 112Y131, and 112Z5, such as binding to OX40, or modulating an activity or function of OX40 (e.g., OX40 signaling). Thus, a modified OX40 antibody can retain at least partial OX40 binding or the ability to modulate one or more OX40 functions or activities (e.g., signaling, a cell response, etc.), for example.

As used herein, the term "modify" and grammatical variations thereof, means that the composition deviates from a reference composition. Modified proteins, nucleic acids and other compositions may have greater or less activity than or a distinct function from a reference unmodified protein, nucleic acid or other composition.

In particular aspects, invention modified antibodies retain one or more of an ability to modulate T cell expansion or survival, modulate numbers of activated, effector, memory or regulatory T cells, or deplete activated, effector, memory or regulatory T cells. In further particular aspects, invention modified antibodies retain one or more of an ability to reduce or delete numbers of auto-reactive T cells specific for a self-antigen or B cells producing antibodies specific for a self-antigen (e.g., a myelin basic protein (MBP), myelin oligodendrocyte glycoprotein (MOG), proteolipid protein (PLP), collagen, synovial joint tissue antigens, insulin, glutamic acid decarboxylase, intestinal antigens, thyroid antigens, histone proteins, muscle antigens or skin antigens).

In various embodiments, the antibody mature heavy or light chain variable region sequence as shown in SEQ ID NOs:7-10 and SEQ ID NOs:44-49 has one or more amino acid substitutions within or outside of a constant region, a complementary determining region (CDR) or a framework (FR) region. In particular aspects, an amino acid substitution is a conservative substitution within or outside of a constant region, a complementary determining region (CDR) or a framework (FR) region. In further various embodiments, invention antibodies are at least 60%, 70%, 80%, 85%, 90%, 95%, 96%, 97%, 98%, 99%, or more identical, or any numerical value or range within or encompassing such percent values, to a heavy or light chain sequence of an antibody produced by a hybridoma cell line denoted as 112F32, 112V8, 112Y131, 112Y55, or 112Z5, SEQ ID NOs:7-10 or SEQ ID NOs:44-49. Typical numbers of substituted residues include 1-3, 3-5, 5-10 amino acid residues, or any numerical value or range within or encompassing such values, or more amino acid residues.

Such antibodies that include amino acid substitutions can be encoded by a nucleic acid. Consequently, nucleic acid sequences encoding antibodies that include amino acid substitutions are also provided.

The terms "identity" or "identical" mean that two or more referenced entities are the same. Thus, where two protein sequences (e.g., OX40 antibodies) are identical, they have the same amino acid sequence, at least within the referenced region or portion. An "area of identity" refers to a portion of two or more referenced entities that are the same. Thus, where two protein sequences are identical over one or more sequence regions they share identity within that region. "Substantial identity" means that a molecule is structurally or functionally conserved such that it has or is predicted to have at least partial function or activity of one or more of the reference molecule functions or activities, or relevant/corresponding region or portion of the reference molecule to which it shares identity. Thus, a polypeptide (e.g., OX40 antibody) with substantial identity has or is predicted to have at least partial activity or function as the reference polypeptide (e.g., OX40 antibody). For example, in a particular embodiment, an OX40 antibody having one or more modifications (e.g., amino acid substitutions, deletions or additions) that retains at least partial activity or function of unmodified OX40 antibody is considered to have substantial identity to the reference OX40 antibody.

Due to variation between structurally and functionally related proteins, the amount of sequence identity required to retain a function or activity depends upon the protein, the region and the function or activity of that region. Although there can be as little as 30% amino acid sequence identity for proteins to retain a given activity or function, typically there is more, e.g., 50%, 60%, 75%, 85%, 90%, 95%, 96%, 97%, 98%, identity to a reference sequence. The extent of identity between two sequences can be ascertained using a computer program and mathematical algorithm known in the art. Such algorithms that calculate percent sequence identity (homology) generally account for sequence gaps and mismatches over the comparison region. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch-2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Natl. Acad. Sci. USA* 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Common.* 304:320 (2003)).

A "conservative substitution" is the replacement of one amino acid by a biologically, chemically or structurally similar residue. Biologically similar means that the substitution does not destroy a biological activity, e.g., OX40 binding activity. Structurally similar means that the amino acids have side chains with similar length, such as alanine, glycine and serine, or a similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

Modified antibodies also include one or more D-amino acids substituted for L-amino acids (and mixtures thereof), structural and functional analogues, for example, peptidomimetics having synthetic or non-natural amino acids or amino acid analogues and derivatized forms. Modifications include cyclic structures such as an end-to-end amide bond between the amino and carboxy-terminus of the molecule or intra- or inter-molecular disulfide bond.

Additional specific non-limiting examples of amino acid modifications include OX40 subsequences and fragments. Exemplary OX40 subsequences and fragments comprise a portion of an OX40 sequence to which an exemplary OX40 antibody of the invention binds. Exemplary OX40 subsequences and fragments also include an immunogenic portion, for example, a portion of OX40 that includes a sequence to which an exemplary OX40 antibody of the invention binds.

In accordance with the invention, there are provided OX40 antibody and nucleic acids encoding OX40 antibody subsequences or fragments that retain, at least a part of, a function or activity of an unmodified or a reference OX40 antibody. As used herein, the term "subsequence" or "fragment" means a portion of the full length molecule. A subsequence of an OX40 antibody encoding an OX40 antibody has at least one fewer amino acids than a full length OX40 (e.g., one or more internal or terminal amino acid deletions from either amino or carboxy-termini). A subsequence of OX40 antibody has at least one fewer amino acid than a full length OX40 antibody. A nucleic acid subsequence has at least one less nucleotide than a full length comparison nucleic acid sequence. Subsequences therefore can be any length up to the full length native OX40.

OX40 antibody subsequences and fragments of the invention include a mature heavy or light chain variable region sequence as shown in SEQ ID NOs:7-10 and SEQ ID NOs: 44-49. OX40 antibody subsequences and fragments of the invention also include Fab, Fab' and F(ab')$_2$, Fv, Fd, single-chain Fv (scFv), disulfide-linked Fvs (sdFv), $V_L$ and $V_H$ domain fragments.

OX40 antibody subsequences and fragments can have the binding affinity as full length antibody, the binding specificity as full length antibody, or one or more activities or functions of as a full length antibody, e.g., a function or activity of OX40 antagonist or agonist antibody. The terms "functional subsequence" and "functional fragment" when referring to an antibody means an antibody portion that retains at least a part of one or more functions or activities as full length reference antibody, e.g., a function or activity of OX40 antibody. For example, an antibody subsequence or fragment that binds to OX40 or a fragment of OX40 is considered a functional subsequence.

Antibody subsequences and fragments can be combined. For example, $V_L$ or $V_H$ subsequences can be joined by a linker sequence thereby forming a $V_L$-$V_H$ chimera. A combination of single-chain Fvs (scFv) subsequences can be joined by a linker sequence thereby forming an scFv-scFv chimera. OX40 antibody subsequences and fragments, include single-chain antibodies or variable region(s) alone or in combination with all or a portion of other OX40 antibody subsequences.

Antibody subsequences and fragments can be prepared by proteolytic hydrolysis of antibody, for example, by pepsin or papain digestion of whole antibodies. Antibody subsequences and fragments produced by enzymatic cleavage with pepsin provide a 5S fragment denoted F(ab')$_2$. This fragment can be further cleaved using a thiol reducing agent to produce 3.5S Fab' monovalent fragments. Alternatively, an enzymatic cleavage using pepsin produces two monovalent Fab' fragments and the Fe fragment directly (see, e.g., U.S. Pat. Nos. 4,036,945 and 4,331,647; and Edelman et al., *Methods Enymol.* 1:422 (1967)). Other methods of cleaving antibodies, such as separation of heavy chains to form monovalent light-heavy chain fragments, further cleavage of fragments, or other enzymatic or chemical may also be used.

Proteins and antibodies, as well as subsequences and fragments thereof, can be produced by genetic methodology. Techniques include expression of all or a part of the gene encoding the protein or antibody into a host cell such as Cos cells or *E. coli*. The recombinant host cells synthesize full length or a subsequence, for example, an scFv (see, e.g., Whitlow et al., In: *Methods: A Companion to Methods in Enzymology* 2:97 (1991), Bird et al., *Science* 242:423 (1988); and U.S. Pat. No. 4,946,778). Single-chain Fvs and antibodies can be produced as described in U.S. Pat. Nos. 4,946,778 and 5,258,498; Huston et al., *Methods Enzymol.* 203:46 (1991); Shu et al., *Proc. Natl. Acad. Sci. USA* 90:7995 (1993); and Skerra et al., *Science* 240:1038 (1988).

Modified forms include derivatized sequences, for example, amino acids in which free amino groups form amine hydrochlorides, p-toluene sulfonyl groups, carbobenzoxy groups; the free carboxy groups from salts, methyl and ethyl esters; free hydroxl groups that form O-acyl or O-alkyl derivatives, as well as naturally occurring amino acid derivatives, for example, 4-hydroxyproline, for proline, 5-hydroxylysine for lysine, homoserine for serine, ornithine for lysine, etc. Modifications can be produced using methods known in the art (e.g., PCR based site-directed, deletion and insertion mutagenesis, chemical modification and mutagenesis, cross-linking, etc.).

Modified forms of protein (e.g., antibody), nucleic acid, and other compositions include additions and insertions. For example, an addition can be the covalent or non-covalent attachment of any type of molecule to a protein (e.g., antibody), nucleic acid or other composition. Typically additions and insertions confer a distinct function or activity.

Additions and insertions include fusion (chimeric) polypeptide or nucleic acid sequences, which is a sequence having one or more molecules not normally present in a reference native (wild type) sequence covalently attached to the sequence. A particular example is an amino acid sequence of another protein (e.g., antibody) to produce a multifunctional protein (e.g., multispecific antibody).

Antibodies of the invention also include chimeras or fusions with one or more additional domains covalently linked thereto to impart a distinct or complementary function or activity. Antibodies include chimeras or fusions in which two or more amino acid sequences are linked together that do not naturally exist in nature.

In accordance with the invention, there are provided OX40 antibodies and nucleic acid encoding OX40 antibodies that include a heterologous domain. Heterologous domains can be an amino acid addition or insertion, but are not restricted to amino acid residues. Thus, a heterologous domain can consist of any of a variety of different types of small or large functional moieties. Such moieties include nucleic acid, peptide, carbohydrate, lipid or small organic compounds, such as a drug, metals (gold, silver), etc.

Particular non-limiting examples of heterologous domains include, for example, tags, detectable labels and cytotoxic agents. Specific examples of tags and detectable labels include T7-, His-, myc-, HA- and FLAG-tags; enzymes (horseradish peroxidase, urease, catalase, alkaline phosphatase, beta-galactosidase, chloramphenicol transferase); enzyme substrates; ligands (e.g., biotin); receptors (avidin); radionuclides (e.g., $C^{14}$, $S^{35}$, $P^{32}$, $P^{33}$, $H^3$, $I^{125}$ and $I^{131}$); electron-dense reagents; paramagnetic labels; fluorophores (fluorescein, rhodamine, phycoerthrin); chromophores; chemi-luminescent (imidazole, luciferase); and bio-luminescent agents. Specific examples of cytotoxic agents include diptheria, toxin, cholera toxin and ricin.

Linker sequences may be inserted between the protein (e.g., antibody), nucleic acid, or other composition and the addition or insertion (e.g., heterologous domain) so that the two entities maintain, at least in part, a distinct function or activity. Linker sequences may have one or more properties that include a flexible structure, an inability to form an ordered secondary structure or a hydrophobic or charged character, which could promote or interact with either domain. Amino acids typically found in flexible protein regions include glycine, asparagine and serine. Other near neutral amino acids, such as threonine and alanine, may also be used in the linker sequence. The length of the linker sequence may vary (see, e.g., U.S. Pat. No. 6,087,329). Linkers further include chemical cross-linking and conjugating agents, such as sulfo-succinimidyl derivatives (sulfo-SMCC, sulfo-SMPB), disuccinimidyl suberate (DSS), disuccinimidyl glutarate (DSG) and disuccinimidyl tartrate (DST).

Further examples of additions include glycosylation, fatty acids, lipids, acetylation, phosphorylation, amidation, formylation, ubiquitinatation, and derivatization by protecting or blocking groups and any of numerous chemical modifications. Other permutations and possibilities will be readily apparent to those of ordinary skill in the art, and are considered to be within the scope of the invention.

Such modified sequences can be made using recombinant DNA technology via cell expression or in vitro translation. Polypeptide and nucleic acid sequences can also be produced by chemical synthesis using methods known in the art, for example, an automated peptide synthesis apparatus (see, e.g., Applied Biosystems, Foster City, Calif.).

OX40 protein suitable for generating antibodies can be produced by any of a variety of standard protein purification or recombinant expression techniques. For example, an OX40 sequence can be produced by standard peptide synthesis techniques, such as solid-phase synthesis. A portion of the protein may contain an amino acid sequence such as a T7 tag or polyhistidine sequence to facilitate purification of expressed or synthesized protein. The protein may be expressed in a cell and purified. The protein may be expressed as a part of a larger protein (e.g., a fusion or chimera) by recombinant methods.

Methods of producing polyclonal and monoclonal antibodies are known in the art. For example, OX40 or an immunogenic fragment thereof, optionally conjugated to a carrier such as keyhole limpet hemocyanin (KLH) or ovalbumin (e.g., BSA), or mixed with an adjuvant such as Freund's complete or incomplete adjuvant, and used to immunize an animal. Using hybridoma technology, splenocytes from immunized animals that respond to OX40 can be isolated and fused with myeloma cells. Monoclonal antibodies produced by the hybridomas can be screened for reactivity with OX40 or an immunogenic fragment thereof.

Animals that may be immunized include primates, mice, rats, rabbits, goats, sheep, cattle, or guinea pigs. Initial and any optional subsequent immunization may be through intravenous, intraperitoneal, intramuscular, or subcutaneous routes. Additionally, to increase the immune response, antigen can be coupled to another protein such as ovalbumin or keyhole limpet hemocyanin (KLH), thyroglobulin and tetanus toxoid, or mixed with an adjuvant such as Freund's complete or incomplete adjuvant. Initial and any optional subsequent immunization may be through intraperitoneal, intramuscular, intraocular, or subcutaneous routes. Subsequent immunizations may be at the same or at different concentrations of OX40 preparation, and may be at regular or irregular intervals.

Animals include those genetically modified to include human gene loci, which can be used to produce human antibodies. Transgenic animals with one or more human immunoglobulin genes are described, for example, in U.S. Pat. No. 5,939,598, WO 02/43478, and WO 02/092812. Using conventional hybridoma technology, splenocytes from immunized mice that are high responders to the antigen can be isolated and fused with myeloma cells. A monoclonal antibody can be obtained that binds to OX40.

Additional methods for producing human polyclonal antibodies and human monoclonal antibodies are described (see, e.g., Kuroiwa et al., *Nat. Biotechnol.* 20:889 (2002); WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598).

The term "human" when used in reference to an antibody, means that the amino acid sequence of the antibody is fully human, i.e., human heavy and human light chain variable and human constant regions. Thus, all of the amino acids are human or exist in a human antibody. An antibody that is non-human may be made fully human by substituting the non-human amino acid residues with amino acid residues that exist in a human antibody. Amino acid residues present in human antibodies, CDR region maps and human antibody consensus residues are known in the art (see, e.g., Kabat, *Sequences of Proteins of Immunological Interest*, 4th Ed. US Department of Health and Human Services. Public Health Service (1987); Chothia and Lesk (1987). A consensus sequence of human $V_H$ subgroup III, based on a survey of 22 known human $V_H$ III sequences, and a consensus sequence of human $V_L$ kappa-chain subgroup I, based on a survey of 30 known human kappa I sequences is described in Padlan *Mol. Immunol.* 31:169 (1994); and Padlan *Mol. Immunol.* 28:489 (1991). Human antibodies therefore include antibodies in which one or more amino acid residues have been substituted with one or more amino acids present in any other human antibody.

OX40 antibodies include humanized antibodies which can be produced using techniques known in the art including, for example, CDR-grafting (EP 239,400; WO91/09967; U.S. Pat. Nos. 5,225,539; 5,530,101; and 5,585,089), veneering or resurfacing (EP 592,106; EP 519,596; Padlan, *Molecular Immunol.* 28:489 (1991); Studnicka et al., *Protein Engineering* 7:805 (1994); Roguska. et al., *Proc. Nat'l. Acad. Sci. USA* 91:969 (1994)), and chain shuffling (U.S. Pat. No. 5,565, 332). Human consensus sequences (Padlan, *Mol. Immunol.* 31:169 (1994); and Padlan, *Mol. Immunol.* 28:489 (1991)) have previously used to produce humanized antibodies (Carter et al., *Proc. Natl. Acad. Sci. USA* 89:4285 (1992); and Presta et al., *J. Immunol.* 151:2623 (1993)).

The term "humanized" when used in reference to an antibody, means that the amino acid sequence of the antibody has non-human amino acid residues (e.g., mouse, rat, goat, rabbit, etc.) of one or more complementarity determining regions (CDRs) that specifically bind to the desired antigen in an acceptor human immunoglobulin molecule, and one or more human amino acid residues in the Fv framework region (FR), which are amino acid residues that flank the CDRs. Antibodies referred to as "primatized" are within the meaning of "humanized" except that the acceptor human immunoglobulin molecule and framework region amino acid residues may be any primate amino acid residue (e.g., ape, gibbon, gorilla, chimpanzees orangutan, macaque), in addition to any human residue. Human FR residues of the immunoglobulin can be replaced with corresponding non-human residues. Residues in the CDR or human framework regions can therefore be substituted with a corresponding residue from the non-human CDR or framework region donor antibody to alter, generally to improve, antigen affinity or specificity, for example. A humanized antibody may include residues, which are found neither in the human antibody nor in the donor CDR or framework sequences. For example, a FR substitution at a particular position that is not found in a human antibody or the donor non-human antibody may be predicted to improve binding affinity or specificity human antibody at that position. Antibody framework and CDR substitutions based upon molecular modeling are well known in the art, e.g., by modeling of the interactions of the CDR and framework residues to identify framework residues important for antigen binding and sequence comparison to identify unusual framework residues at particular positions (see, e.g., U.S. Pat. No. 5,585,089; and Riechmann et al., *Nature* 332:323 (1988)).

OX40 antibodies include chimeric antibodies. As used herein, the term "chimeric" and grammatical variations thereof, when used in reference to an antibody, means that the amino acid sequence of the antibody contains one or more portions that are derived from, obtained or isolated from, or based upon two or more different species. For example, a portion of the antibody may be human (e.g., a constant region) and another portion of the antibody may be non-human (e.g., a murine heavy or murine light chain variable region). Thus, an example of a chimeric antibody is an antibody in which different portions of the antibody are of different species origins. Unlike a humanized or primatized antibody, a chimeric antibody can have the different species sequences in any region of the antibody.

Methods for producing chimeric antibodies are known in the art (e.g., Morrison, *Science* 229:1202 (1985); Oi et al., *BioTechniques* 4:214 (1986); Gillies et al., *J. Immunol. Methods* 125:191 (1989); and U.S. Pat. Nos. 5,807,715; 4,816,567; and 4,816,397). Chimeric antibodies in which a variable domain from an antibody of one species is substituted for the variable domain of another species are described, for example, in Munro, *Nature* 312:597 (1984); Neuberger et al., *Nature* 312:604 (1984); Sharon et al., *Nature* 309:364 (1984); Morrison et al., *Proc. Nat'l. Acad. Sci. USA* 81:6851 (1984); Boulianne et al., *Nature* 312:643 (1984); Capon et al., *Nature* 337:525 (1989); and Traunecker et al., *Nature* 339:68 (1989).

OX40 antibodies can also be generated using hybridoma, recombinant, and phage display technologies, or a combination thereof (see U.S. Pat. Nos. 4,902,614, 4,543,439, and 4,411,993; see, also *Monoclonal Antibodies, Hybridomas: A New Dimension in Biological Analyses*, Plenum Press, Kennett, McKearn, and Bechtol (eds.), 1980, and Harlow et al., *Antibodies: A Laboratory Manual*, Cold Spring Harbor Laboratory Press, 2nd ed. 1988).

Suitable techniques that additionally may be employed in antibody methods include OX40-based affinity purification, non-denaturing gel purification, HPLC or RP-HPLC, size exclusion, purification on protein A column, or any combination of these techniques. OX40 antibody isotype can be determined using an ELISA assay, for example, a human Ig can be identified using mouse Ig-absorbed anti-human Ig.

OX40 suitable for generating antibodies can be produced by any of a variety of standard protein purification or recombinant expression techniques known in the art. Forms of OX40 suitable for generating an immune response include OX40 subsequences, such as an immunogenic fragment. Additional forms OX40 include OX40 expressing cells, OX40 containing preparations or cell extracts or fractions, partially purified OX40.

In accordance with the invention, there are provided isolated or purified cells that express OX40 antibodies, subsequences and fragments thereof, and nucleic acids encoding OX40 antibodies, subsequences and fragments of the invention. In one embodiment, an isolated cell expresses an antibody having the amino acid sequences of heavy or light chain variable region of an antibody denoted as 112F32, 112V8, 112Y131, 112Y55, or 112Z5. In another embodiment, an isolated cell expresses an antibody having the binding specificity as antibody produced by a hybridoma cell line denoted as 112F32, 112V8, 112Y131, 112Y55, or 112Z5. In a further embodiment, an isolated cell expresses an antibody that competes with antibody produced by a hybridoma cell line denoted as 112F32, 112V8, 112Y131, 112Y55, or 112Z5 for the binding of OX40. In an additional embodiment, an isolated cell expresses an antibody that has greater or less binding affinity for OX40 than antibody produced by a hybridoma cell line denoted as 112F32, 112V8, 112Y131, 112Y55, or 112Z5. In particular aspects, binding affinity for OX40 is within about 1-5000 fold of antibody produced by a hybridoma cell line denoted as 112F32, 112V8, 112Y131, 112Y55, or 112Z5. In additional particular aspects, binding affinity for OX40 is within about $KD10^{-6}$ M to about $KD10^{-13}$ M of an antibody produced by a hybridoma cell line denoted as 112F32, 112V8, 112Y131, 112Y55, or 112Z5. Specific non-limiting example of isolated or purified cells that express OX40 antibodies, subsequences and fragments thereof, and nucleic acids encoding OX40 antibodies, subsequences and fragments of the invention include spleen cells, hybridoma cells and CHO cells. The isolated or purified cells may be a plurality or population of cells from a primary cell isolate (e.g., splenocytes), a secondary or passaged cell isolate, or an established or immortalized cell culture (hybridoma or CHO cells).

In accordance with the invention, further provided are methods of producing antibodies that specifically bind to OX40. In one embodiment, a method for producing an OX40 antibody includes administering a human OX40, subsequence or fragment (e.g., an OX40 extracellular domain), optionally conjugated with human Fc recombinant protein, to an animal capable of expressing human immunoglobulin (e.g., transgenic mouse or transgenic cow), screening the animal for expression of human OX40 antibody, and selecting an animal that produces a human OX40 antibody, isolating an antibody from the selected animal. In one aspect, the method determines whether the human OX40 antibody has OX40 antagonist or agonist activity.

In accordance with the invention, additionally provided are methods of producing human OX40 antibodies that inhibit or prevent OX40 binding to OX40 ligand (OX40L). In one embodiment, a method for producing a human OX40 antibody includes administering OX40, subsequence or fragment (e.g., an OX40 extracellular domain), optionally conjugated with human Fc recombinant protein to an animal capable of expressing human immunoglobulin (e.g., transgenic mouse or transgenic cow), screening the animal for expression of human OX40 antibody, selecting an animal that produces a human OX40 antibody, and isolating an antibody from the selected animal that produces human OX40 antibody. In one aspect, the method determines whether the human OX40 antibody inhibits or prevents OX40 binding to OX40 ligand (OX40L).

In accordance with the invention, there are provided non-human transgenic animals that express an OX40 antibody having one or more of the following characteristics: a) is identical to an antibody produced by a hybridoma cell line denoted as 112F32, 112V8, 112Y131, 112Y55, or 112Z5; b) binds to an epitope in an amino acid sequence of OX40 extracellular domain to which an antibody produced by a hybridoma cell line denoted as 112F32, 112V8, 112Y131, 112Y55, or 112Z5; c) has an OX40 binding affinity within about 1-5000 fold of an antibody produced by a hybridoma cell line denoted as 112F32, 112V8, 112Y131, 112Y55, or 112Z5; d) has an OX40 binding affinity within about KD $10^{-6}$ M to about KD $10^{-12}$ M of an antibody produced by a hybridoma cell line denoted as 112F32, 112V8, 112Y131, 112Y55, or 112Z5; e) has the binding specificity of an antibody produced by a hybridoma cell line denoted as 112F32, 112V8, 112Y131, 112Y55, or 112Z5; or f) competes with an antibody produced by a hybridoma cell line denoted as 112F32, 112V8, 112Y131, 112Y55, or 112Z5 for binding to OX40.

In accordance with the invention, there are also provided isolated or purified nucleic acids encoding OX40 antibodies, subsequences and fragments thereof. In various embodiments a nucleic acid sequence encodes a sequence of mature heavy or light chain variable region sequence as shown in SEQ ID NOs:7-10 and SEQ ID NOs:44-49, or a subsequence thereof. In additional embodiments a nucleic acid sequence comprises any of SEQ ID NOs:3-6 and SEQ ID NOs:38-43, and subsequences thereof. In a further embodiment a nucleic acid sequence comprises a sequence degenerate with respect to any of SEQ ID NOs:3-6 and SEQ ID NOs:38-43, and subsequences thereof.

Nucleic acids can be of various lengths. Lengths of nucleic acids that encode invention OX40 antibodies or subsequences thereof typically range from about 100 nucleotides to 600 nucleotides, or any numerical value or range within or encompassing such lengths, 100 to 150, 150 to 200, 200 to 250, 250 to 300, 300 to 350, 350 to 400, 400 to 450, 450 to 500, 500 to 550, or about 550 to 600 nucleotides in length, or any numerical value or range or value within or encompassing such lengths. Lengths of nucleic acids that specifically hybridize to nucleic acids encoding invention OX40 antibodies or subsequences thereof typically range from about 10-20, 20-30, 30-50, 50-100, 100-150, 150-200, 200-250, 250-300, 300-400, 400-500, 500-600 nucleotides, or any numerical value or range within or encompassing such lengths.

The terms "nucleic acid" and "polynucleotide" refer to at least two or more ribo- or deoxy-ribonucleic acid base pairs (nucleotides) that are linked through a phosphoester bond or equivalent. Nucleic acids include polynucleotides and polynucleosides. Nucleic acids include single, double or triplex, circular or linear, molecules. Exemplary nucleic acids include but are not limited to: RNA, DNA, cDNA, genomic nucleic acid, naturally occurring and non naturally occurring nucleic acid, e.g., synthetic nucleic acid. Short nucleic acids and polynucleotides (e.g., 10-20, 20-30, 30-50, 50-100 nucleotides) are commonly referred to as "oligonucleotides" or "probes" of single- or double-stranded DNA.

Nucleic acids are provided that encode an amino acid sequence having one or more substituted, added or deleted amino acid residues of heavy or light chain variable region sequence as shown in any of SEQ ID NOs:7-10 and SEQ ID NOs:44-49. In one embodiment the substituted, added or deleted heavy or light chain variable region sequence has binding affinity for an epitope of OX40 extracellular domain. In another embodiment the substituted, added or deleted heavy or light chain variable region sequence has an activity of an antibody produced by a hybridoma cell line denoted as 112F32, 112V8, 112Y131, 112Y55, or 112Z5, for example, modulating a function or activity of OX40.

The invention provides nucleic acids that hybridize to a nucleic acid that encodes all or a subsequence of an OX40 antibody produced by a hybridoma cell line denoted as 112F32, 112V8, 112Y131, 112Y55, or 112Z5, that is at least 80-90% complementary or homologous to the nucleic acid sequence that encodes all or a subsequence or fragment of antibody produced by a hybridoma cell line denoted as 112F32, 112V8, 112Y131, 112Y55, or 112Z5. In one embodiment, the nucleic acid sequence has a length from about 10-20, 20-30, 30-50, 50-100, 100-150, 150-200, 200-250, 250-300, 300-400, 400-500, 500-600, nucleotides, or any numerical value or range within or encompassing such lengths. In particular aspects, the nucleic acid sequence hybridizes to a heavy or light chain variable region sequence, or portion thereof (e.g., a CDR, an FR, etc.) of an antibody produced by a hybridoma cell line denoted as 112F32, 112V8, 112Y131, 112Y55, or 112Z5.

The term "hybridize" and grammatical variations thereof refer to the binding between nucleic acid sequences. Hybridizing sequences will generally have more than about 50% homology to a nucleic acid that encodes an amino acid sequence of a reference (e.g., OX40 antibody) sequence. The hybridization region between hybridizing sequences typically is at least about 12-15 nucleotides, 15-20 nucleotides, 20-30 nucleotides, 30-50 nucleotides, 50-100 nucleotides, 100 to 200, 300 to 400 nucleotides or more, or any numerical value or range within or encompassing such lengths.

Nucleic acid sequences further include nucleotide and nucleoside substitutions, additions and deletions, as well as derivatized forms and fusion/chimeric sequences (e.g., encoding OX40 antibody fused to a heterologous domain). For example, due to the degeneracy of the genetic code, nucleic acids include sequences and subsequences degenerate with respect to nucleic acids that encode antibody produced by a hybridoma cell line denoted as 112F32, 112V8, 112Y131, 112Y55, and 112Z5. Other examples are nucleic acids complementary to a sequence that encodes an antibody produced by a hybridoma cell line denoted as 112F32, 112V8, 112Y131, 112Y55, or 112Z5, subsequences and fragments thereof.

Nucleic acids can be produced using various standard cloning and chemical synthesis techniques. Techniques include, but are not limited to nucleic acid amplification, e.g., polymerase chain reaction (PCR), with genomic DNA or cDNA targets using primers (e.g., a degenerate primer mixture) capable of annealing to antibody encoding sequence. Nucleic acids can also be produced by chemical synthesis (e.g., solid phase phosphoramidite synthesis) or transcription from a gene. The sequences produced can then be translated in vitro, or cloned into a plasmid and propagated and then expressed in a cell (e.g., a host cell such as yeast or bacteria, a eukaryote such as an animal or mammalian cell or in a plant).

In accordance with the invention, there are further provided nucleic acid sequences of the invention that include vectors. In one embodiment, a vector includes a nucleic acid sequence encoding an OX40 antibody, subsequence or fragment thereof. In particular embodiments, a vector includes a nucleic acid sequence encoding any antibody produced by a hybridoma cell line denoted as 112F32, 112V8, 112Y131, 112Y55, and 112Z5, subsequence or fragment thereof.

Vectors are vehicles that can be manipulated by insertion or incorporation of a nucleic acid. Vectors include plasmid, viral, prokaryotic (bacterial) and eukaryotic (plant, fungal, mammalian) vectors. Vectors can be used for expression of nucleic acids in vitro or in vivo. Such vectors, referred to as "expression vectors," are useful for introducing nucleic acids, including nucleic acids that encode OX40 antibodies, subsequences and fragments thereof, and expressing the encoded protein in vitro (e.g., in solution or in solid phase), in cells or in a subject in vivo.

Vectors can also be used for manipulation of nucleic acids. For genetic manipulation "cloning vectors" can be employed, and to transcribe or translate the inserted nucleic acid, in vitro (e.g., in solution or in solid phase), in cells or in a subject in vivo.

A vector generally contains an origin of replication for propagation in a cell in vitro or in vivo. Control elements, including expression control elements, present within a vector, can be included to facilitate transcription and translation, as appropriate.

Vectors can include a selection marker. A "selection marker" is a gene that allows for the selection of cells containing the gene. "Positive selection" refers to a process of selecting cells that contain the selection marker upon exposure to the positive selection. Drug resistance is one example of a positive selection marker-cells containing the marker will survive in a culture medium containing the drug, and cells lacking the marker will die. Selection markers include drug resistance genes such as neo, which confers resistance to G418; hygr, which confers resistance to hygromycin; and puro, which confers resistance to puromycin. Other positive selection marker genes include genes that allow identification or screening of cells containing the marker. These genes include genes for fluorescent proteins (GFP and GFP-like chromophores, luciferase), the lacZ gene, the alkaline phosphatase gene, and surface markers such as CD8, among others. "Negative selection" refers to a process in which cells containing a negative selection marker are killed upon exposure to an appropriate negative selection agent. For example, cells which contain the herpes simplex virus-thymidine kinase (HSV-tk) gene (Wigler et al., Cell 11:223 (1977)) are sensitive to the drug gancyclovir (GANC). Similarly, the gpt gene renders cells sensitive to 6-thioxanthine.

Viral vectors include those based upon retroviral (lentivirus for infecting dividing as well as non-dividing cells), foamy viruses (U.S. Pat. Nos. 5,624,820, 5,693,508, 5,665, 577, 6,013,516 and 5,674,703; WO92/05266 and WO92/14829), adenovirus (U.S. Pat. Nos. 5,700,470, 5,731,172 and 5,928,944), adeno-associated virus (AAV) (U.S. Pat. No. 5,604,090), herpes simplex virus vectors (U.S. Pat. No. 5,501,979), cytomegalovirus (CMV) based vectors (U.S. Pat. No. 5,561,063), reovirus, rotavirus genomes, simian virus 40 (SV40) or papilloma virus (Cone et al., Proc. Natl. Acad. Sci. USA 81:6349 (1984); *Eukaryotic Viral Vectors*, Cold Spring Harbor Laboratory, Gluzman ed., 1982; Sarver et al., Mol. Cell. Biol. 1:486 (1981); U.S. Pat. No. 5,719,054). Adenovirus efficiently infects slowly replicating and/or terminally differentiated cells and can be used to target slowly replicating and/or terminally differentiated cells. Additional viral vectors useful for expression include parvovirus, Norwalk virus, coronaviruses, paramyxo- and rhabdoviruses, togavirus (e.g., sindbis virus and semliki forest virus) and vesicular stomatitis virus (VSV).

Vectors including a nucleic acid can be expressed when the nucleic acid is operably linked to an expression control element. The term "operably linked" refers to a physical or a functional relationship between the elements referred to that permit them to operate in their intended fashion. Thus, a nucleic acid "operably linked" to an expression control element means that the control element modulates nucleic acid transcription and as appropriate, translation of the transcript.

An "expression control element" or "expression control sequence" is a polynucleotide that influences expression of an operably linked nucleic acid. Promoters and enhancers are particular non-limiting examples of expression control elements and sequences. A "promoter" is a cis-acting DNA regulatory region capable of initiating transcription of a downstream (3' direction) nucleic acid sequence. The promoter sequence includes nucleotides that facilitate transcription initiation. Enhancers also regulate nucleic acid expression, but can function at a distance from the transcription start site of the nucleic acid to which it is operably linked. Enhancers function when located at either 5' or 3' ends of the nucleic acid, as well as within the nucleic acid (e.g., introns or coding sequences). Additional expression control elements include leader sequences and fusion partner sequences, internal ribosome binding sites (IRES) elements for the creation of multigene, or polycistronic, messages, splicing signal for introns, maintenance of the correct reading frame of the gene to permit in-frame translation of mRNA, polyadenylation signal to provide proper polyadenylation of the transcript of interest, and stop codons.

Expression control elements include "constitutive" elements in which transcription of an operably linked nucleic acid occurs without the presence of a signal or stimuli. Expression control elements that confer expression in response to a signal or stimuli, which either increase or decrease expression of operably linked nucleic acid, are "regulatable." A regulatable element that increases expression of operably linked nucleic acid in response to a signal or stimuli is referred to as an "inducible element." A regulatable element that decreases expression of the operably linked nucleic acid in response to a signal or stimuli is referred to as a "repressible element" (i.e., the signal decreases expression; when the signal is removed or absent, expression increases).

For bacterial expression, constitutive promoters include T7, as well as inducible promoters such as pL of bacteriophage λ, plac, ptrp, ptac (ptrp-lac hybrid promoter). In insect cell systems, constitutive or inducible promoters (e.g., ecdysone) may be used. In yeast, constitutive promoters include, for example, ADH or LEU2 and inducible promoters such as GAL (see, e.g., Ausubel et al., In: *Current Protocols in Molecular Biology*, Vol. 2, Ch. 13, ed., Greene Publish. Assoc. & Wiley Interscience, 1988; Grant et al., In: *Methods* in *Enzymology,* 153:516-544 (1987), eds. Wu & Grossman, 1987, Acad. Press, N.Y.; Glover, *DNA Cloning,* Vol. II, Ch. 3, IRL Press, Wash., D.C., 1986; Bitter, In: *Methods in Enzymology,* 152:673-684 (1987), eds. Berger & Kimmel, Acad. Press, N.Y.; and, Strathern et al., *The Molecular Biology of the Yeast Saccharomyces* eds. Cold Spring Harbor Press, Vols. I and II (1982)).

For mammalian expression, constitutive promoters of viral or other origins may be used. For example, CMV, SV40, or viral long terminal repeats (LTRs) and the like, or inducible promoters derived from the genome of mammalian cells (e.g., metallothionein IIA promoter; heat shock promoter, steroid/thyroid hormone/retinoic acid response elements) or from mammalian viruses (e.g., the adenovirus late promoter; mouse mammary tumor virus LTR) are used.

Expression control elements include elements active in a particular tissue or cell type, referred to as "tissue-specific expression control elements." Tissue-specific expression control elements are typically more active in specific cell or tissue types because they are recognized by transcriptional activator proteins, or other transcription regulators active in the specific cell or tissue type, as compared to other cell or tissue types. Particular non-limiting examples of such expression control elements are promoters such as hexokinase II, COX-2, alpha-fetoprotein, carcinoembryonic antigen, DE3/MUC1, prostate specific antigen, C-erB2/neu, glucose-dependent insulinotropic polypeptide (GIP), telomerase reverse transcriptase and hypoxia-responsive promoter.

In accordance with the invention, host cells transformed or transfected with OX40 nucleic acid or vector of the invention are provided. Host cells include but are not limited to prokaryotic and eukaryotic cells such as bacteria, fungi (yeast), plant, insect, and animal (e.g., mammalian, including primate and human) cells. Non-limiting examples of transformed cells include bacteria transformed with recombinant bacteriophage nucleic acid, plasmid nucleic acid or cosmid nucleic acid expression vectors; yeast transformed with recombinant yeast expression vectors; plant cells infected with recombinant virus expression vectors (e.g., cauliflower mosaic virus, CaMV; tobacco mosaic virus, TMV) or transformed with recombinant plasmid expression vectors (e.g., Ti plasmid); insect cells infected with recombinant virus expression vectors (e.g., baculovirus); and animal cells infected with recombinant virus expression vectors (e.g., retroviruses, adenovirus, vaccinia virus), or transformed animal cells engineered for stable expression. A non-limiting example of a mammalian host cell that expresses OX40 antibodies, subsequences and fragments thereof include a CHO cell. The host cells may be a plurality or population of cells from a primary cell isolate, a secondary or passaged cell isolated, or an established or immortalized cell culture.

The term "transformed" or "transfected" when use in reference to a cell (e.g., a host cell) or organism, means a genetic change in a cell following incorporation of an exogenous molecule, for example, a protein or nucleic acid (e.g., a transgene) into the cell. Thus, a "transfected" or "transformed" cell is a cell into which, or a progeny thereof in which an exogenous molecule has been introduced by the hand of man, for example, by recombinant DNA techniques.

The nucleic acid or protein can be stably or transiently transfected or transformed (expressed) in the cell and progeny thereof. The cell(s) can be propagated and the introduced protein expressed, or nucleic acid transcribed. A progeny of a transfected or transformed cell may not be identical to the parent cell, since there may be mutations that occur during replication.

Typically, cell transfection or transformation employs a vector. A vector can be encompassed within a viral particle or vesicle and optionally targeted to particular cell types by inclusion of a protein on the particle or vesicle surface that binds to a target cell ligand or receptor. Thus, the viral particle or vesicle itself, or a protein on the viral surface can be made to target cells for transfection or transformation in vitro, ex vivo or in vivo. Accordingly, viral and non-viral vector means of delivery into cells, tissue or organs, in vitro, in vivo and ex vivo are included.

Introduction of nucleic acid into target cells (e.g., host cells) can also be carried out by methods known in the art such as osmotic shock (e.g., calcium phosphate), electroporation, microinjection, cell fusion, etc. Introduction of nucleic acid and polypeptide in vitro, ex vivo and in vivo can also be accomplished using other techniques. For example, a polymeric substance, such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. A nucleic acid can be entrapped in microcapsules prepared by coacervation techniques or by interfacial polymerization, for example, by the use of hydroxymethylcellulose or gelatin-microcapsules, or poly(methylmethacrolate) microcapsules, respectively, or in a colloid system. Colloidal dispersion systems include macromolecule complexes, nano-capsules, microspheres, beads, and lipid-based systems, including oil-in-water emulsions, micelles, mixed micelles, and liposomes.

Liposomes for introducing various compositions into cells are known in the art and include, for example, phosphatidylcholine, phosphatidylserine, lipofectin and DOTAP (e.g., U.S. Pat. Nos. 4,844,904, 5,000,959, 4,863,740, and 4,975,282; and GIBCO-BRL, Gaithersburg, Md.). Piperazine based amphilic cationic lipids useful for gene therapy also are known (see, e.g., U.S. Pat. No. 5,861,397). Cationic lipid systems also are known (see, e.g., U.S. Pat. No. 5,459,127). Polymeric substances, microcapsules and colloidal dispersion systems such as liposomes are collectively referred to herein as "vesicles."

Invention OX40 antibodies are useful in treatment, therapeutic and diagnostic applications, including clinical and diagnostic methods. For example, in a mouse model of acute and chronic graft versus host disease (GVHD) where human PBMC were transferred into irradiated severe combined immunodeficient (SCID) mice, human anti-human OX40 antagonist antibodies reduced human T cell numbers and disease pathology when administered before or after disease onset. Thus, invention OX40 antibodies are capable of reducing, decreasing or preventing a symptom of graft versus host disease (GVHD) in an acute or chronic xenograft host disease model; and causing a remission or regression of graft versus host disease in an acute or chronic xenograft host disease model (e.g., an immunodeficient (SCID) mouse). Invention antibodies were also able to induce lysis of OX40 expressing cells by natural killer cells. Although not wishing to be bound by any theory, lysis of OX40 expressing cells may be due to antibody dependent cellular cytotoxicity (ADCC).

Invention OX40 antibodies are therefore useful in treatment or therapy of disorders and diseases which are amenable or may respond favorably by modulating an OX40 activity or function. Thus, an OX40 antagonist antibody can be used to treat disorders, diseases, physiological conditions, pathologies and symptoms thereof that are amenable to or are likely to respond favorably to reducing, decreasing, inhibiting, preventing or blocking OX40 activity or function, whereas an OX40 agonist antibody can be used to treat disorders, diseases, physiological conditions, pathologies and symptoms thereof that are amenable to or are likely to respond favorably to stimulating, increasing, enhancing, promoting or inducing OX40 activity or function.

In accordance with the invention, there are provided methods of treating disorders, diseases, conditions, pathologies and adverse symptoms or abnormalities associated with undesirable or aberrant immune responses. As used herein, an "undesirable immune response" or "aberrant immune response" refers to any immune response, activity or function that is greater or less than desired or physiologically normal. An undesirable immune response, function or activity can be a normal response, function or activity. Thus, normal immune responses so long as they are undesirable, even if not considered aberrant, are included within the meaning of these terms. An undesirable immune response, function or activity can also be an abnormal response, function or activity. An abnormal (aberrant) immune response, function or activity deviates from normal. Undesirable and aberrant immune responses can be humoral, cell-mediated or a combination thereof, either chronic or acute.

An example of an undesirable or aberrant immune response is an immune response that is hyper-responsive, such as in the case of an autoimmune disorder or disease (e.g., autoimmunity). Another example of an undesirable or aberrant immune response is where an immune response leads to acute or chronic inflammation in any tissue or organ. Yet another example of an undesirable or aberrant immune response is where an immune response leads to destruction of cells, tissue or organ, such as a transplant rejection, graft vs. host disease (GVHD), an autoimmune disorder or disease, or inflammation. Still another example of an undesirable or aberrant immune response is where the immune response is hypo-responsive, such as where response to an antigen is less than desired, e.g., tolerance has occurred.

Undesirable and aberrant immune responses therefore include chronic and acute immune disorders and diseases characterized by physiological conditions, pathologies and adverse symptoms or abnormalities, depending upon the disorder or disease. Particular non-limiting examples of immune disorders and diseases to which the invention applies include graft versus host disease (GVHD), transplant rejection, autoimmune disorders and inflammation.

In accordance with the invention, there are provided in vivo treatment and therapeutic methods based, at least in part, upon the ability of OX40 antibodies to modulate an OX40 activity or function. In particular methods of treatment embodiments, disorders, diseases, physiological conditions, pathologies and symptoms amenable to or that may respond to treatment or therapy with invention OX40 antibodies include, for example, a chronic or acute immune disease or disorder. In further methods of treatment embodiments, disorders, diseases, physiological conditions, pathologies and symptoms amenable to treatment or therapy with invention OX40 antibodies include, for example, inflammation, transplant rejection, graft versus host disease (GVHD), an autoimmune disorder or disease, such as rheumatoid arthritis, multiple sclerosis, diabetes (e.g., insulin-dependent diabetes mellitus, IDDM, type I diabetes), Crohn's disease (CD), inflammatory bowel disease (IBD), ulcerative colitis (UC), celiac disease, psoriasis, systemic lupus erythematosus (SLE), proliferative lupus nephritis, granulomatous myopathy, polymyositis, and an OX40-mediated cell response that is undesirable or aberrant, for example.

The invention therefore provides methods in which OX40 antibodies, subsequences or fragments are used for reducing, decreasing, inhibiting, preventing and blocking a chronic or acute immune disease or disorder, inflammation, transplant rejection, graft versus host disease (GVHD), or an autoimmune disorder, such as rheumatoid arthritis, multiple sclerosis, diabetes (e.g., insulin-dependent diabetes mellitus, IDDM, type I diabetes), Crohn's disease (CD), inflammatory bowel disease (IBD), ulcerative colitis (UC), celiac disease, psoriasis, systemic lupus erythematosus (SLE), proliferative lupus nephritis, granulomatous myopathy, polymyositis, or an OX40-mediated cell response that is undesirable or aberrant, treating and reducing, decreasing, inhibiting, preventing and blocking lung inflammation in airway hyper-reactivity/hypersensitivity (e.g., asthma, allergic asthma) and in other tissues and organs. Specific non-limiting examples of a symptom of graft versus host disease treatable in accordance with the invention is weight loss, hair loss, skin rash, hematuria, hydroperitoneum, and inflammatory cell infiltrates in liver, intestinal tract, lung, skin, and death.

OX40 antibodies are also useful for reducing, decreasing, inhibiting, preventing and blocking inflammation present in lung, joint, muscle, skin, central or peripheral nervous system or bowel. OX40 antibodies are additionally useful for reducing, decreasing, inhibiting, preventing and blocking inflammation that results from response of a subject to infectious agents (e.g., bacterial, viral or parasitic infectious agents).

Additional conditions amenable to treatment or therapy with OX40 antibodies include, for example, osteoarthritis, psoriatic arthritis, encephalomyelitis, myasthenia gravis, autoimmune thyroiditis, atopic dermatitis, eczematous dermatitis, psoriasis, Sjögren's Syndrome, aphthous ulcer, iritis, conjunctivitis, keratoconjunctivitis, cutaneous lupus erythematosus, scleroderma, vaginitis, proctitis, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia (ITP), polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, interstitial lung fibrosis, Hashimoto's thyroiditis, autoimmune polyglandular syndrome, immune-mediated infertility, autoimmune Addison's disease, pemphigus vulgaris, pemphigus foliaceus, dermatitis herpetiformis, autoimmune alopecia, Vitiligo, autoimmune hemolytic anemia, autoimmune thrombocytopenic purpura, pernicious anemia, Guillain-Barre syndrome, Stiff-man syndrome, acute rheumatic fever, sympathetic ophthalmia, Goodpasture's syndrome, systemic necrotizing vasculitis, antiphospholipid syndrome, asthma (e.g., allergic asthma) and allergies.

As used herein, the terms "transplant," "transplantation" and grammatical variations thereof mean grafting, implanting, or transplanting a cell, tissue or organ from one part of the body to another part, or from one individual or animal to another individual or animal. The transplanted cell, tissue or organ may therefore be an allograft or xenograft. Exemplary transplant cells include bone marrow, hematopoietic stem cells, peripheral blood stem cells or cord blood stem cells, allogeneic or non-allogeneic cells, and neural cells. Exemplary transplant tissues include skin, blood vessel, eye and bone marrow. Exemplary transplant organs include kidney, heart, lung, pancreas and liver. The term also includes genetically modified cells, tissue and organs, e.g., by ex vivo gene therapy in which the transformed cells, tissue and organs are obtained or derived from a subject (e.g., human or animal) who then receives the transplant from a different subject (e.g., human or animal).

Inflammation treatable in accordance with the invention include inflammatory responses mediated by OX40 or amendable to treatment with OX40 antibody due to modulation of OX40, which in turn can modulate one or more of cell proliferation, survival, death, or activity of lymphocytes (e.g., activated, effector, memory or regulatory T cells), etc. Methods (e.g., treatment) can result in a reduction in occurrence, frequency, severity, progression, or duration of inflammation. Exemplary symptoms of inflammation include one or more of swelling, pain, rash, headache, fever, nausea, skeletal joint stiffness, or tissue or cell damage.

Inflammation may cause, directly or indirectly, cell, tissue or organ damage, either to multiple cells, tissues or organs, or to a single cell type, tissue type or organ. Exemplary tissues and organs that can exhibit damage include epidermal or mucosal tissue, gut, bowel, pancreas, thymus, liver, kidney, spleen, skin, or a skeletal joint (e.g., knee, ankle, hip, shoulder, wrist, finger, toe, or elbow). Treatment in accordance with the invention can result in reducing, inhibiting or preventing progression or worsening of tissue damage, or lead to regeneration of a damaged organ or tissue, e.g., skin, mucosum, liver.

As used herein, the terms "treat," "treating," "treatment" and grammatical variations thereof mean a protocol, regimen, process or remedy performed on an individual subject or patient, in which it is desired to obtain a physiologic effect or outcome in that patient. Methods of the invention therefore include, among other things, treatment and therapeutic methods that provide a measurable improvement or beneficial effect in a disorder, disease, physiological condition, pathology or a symptom of a given subject. A measurable improvement or beneficial effect is any objective or subjective, transient, temporary, or long-term improvement in the disorder, disease, physiological condition, pathology or symptom, or a reduction in onset, severity, duration or frequency of an adverse symptom associated with or caused by the disorder, disease, physiological condition, pathology or condition. An invention method need not take effect immediately and there may be some delay, but over time eventual improvement or beneficial effect, stabilization or amelioration in a given subject will occur.

A satisfactory clinical endpoint of a treatment method in accordance with the invention is achieved, for example, when there is an incremental or a partial decrease or reduction in severity, duration or frequency of one or more pathologies, adverse symptoms or complications, associated with the disorder, disease, pathology or condition, or inhibition, reduction, prevention or reversal of one or more of the physiological, pathological, biochemical or cellular manifestations or characteristics of the disorder, disease, physiological condition, pathology or symptom (e.g., a chronic or acute immune disease or disorder, GVHD, transplant rejection, inflammation, or an autoimmune disorder). A therapeutic benefit or improvement therefore can but need not be a cure, or ablation of a majority or all pathologies, adverse symptoms or complications associated with or caused by the disorder, disease, physiological condition, pathology or symptom (e.g., a chronic or acute immune disease or disorder, GVHD, transplant rejection, inflammation, or an autoimmune disorder). Thus, a therapeutic benefit or improvement need not result in a complete cure of any or all pathologies, adverse symptoms or complications associated with or caused by the disorder, disease, physiological condition, or pathology (e.g., a chronic or acute immune disease or disorder, GVHD, transplant rejection, inflammation, or an autoimmune disorder). For example, partial reduction, decrease or inhibition, or a stabilization, or slowing progression or worsening of a pathology, adverse symptom or complication associated with or caused by the disorder, disease, physiological condition or pathology (e.g., a chronic or acute immune disease or disorder, GVHD, transplant rejection, inflammation, or an autoimmune disorder), even if only for a few days, weeks or months, or even if one or more pathologies, adverse symptoms or complications associated with or caused by a the disease, disorder, pathology or condition remain (e.g., a chronic or acute immune disease or disorder, GVHD, transplant rejection, inflammation, or an autoimmune disorder) is a satisfactory clinical outcome.

In various particular embodiments, treatment methods include alleviating or ameliorating one or more adverse (physical) symptoms or consequences associated with a chronic or acute immune disorder or disease. In various additional particular embodiments, treatment methods include reducing, decreasing or preventing onset, frequency, duration or severity of one or more adverse symptoms or physical consequences associated with graft versus host disease (e.g., weight loss, hair loss, skin rash, hematuria, hydroperitoneum, inflammatory cell infiltrates in liver, intestinal tract, lung and death), or result in a remission or regression of graft versus host disease, or result in preventing graft versus host disease. In various further particular embodiments, treatment methods include reducing, decreasing or preventing onset, frequency, duration or severity of one or more adverse symptoms or physical consequences associated with transplant or graft rejection (e.g., an immune response against the transplant or graft, or transplant or graft cell destruction), or result in a remission or regression of transplant or graft rejection, or result in preventing transplant or graft rejection. In various still further particular embodiments, treatment methods include reducing, decreasing or preventing onset, frequency, duration or severity of one or more adverse symptoms or physical consequences associated with rheumatoid arthritis, multiple sclerosis, diabetes (e.g., insulin-dependent diabetes mellitus, IDDM, type I diabetes), Crohn's disease (CD), inflammatory bowel disease (IBD), ulcerative colitis (UC), celiac disease, psoriasis, systemic lupus erythematosus (SLE), proliferative lupus nephritis, granulomatous myopathy, polymyositis, or an OX40-mediated cell response that is undesirable or aberrant. In yet further various particular embodiments, treatment methods include reducing numbers or proliferation of self-reactive cells or cells producing anti-self protein antibodies, inhibiting or preventing an increase in numbers, proliferation or survival of self-reactive cells or cells producing anti-self protein antibodies.

In the case of an immune disorder or disease, a measurable improvement or beneficial effect includes modulating numbers, proliferation or an activity of lymphocytes (e.g., activated, effector, memory or regulatory T cells) towards physiologically normal baseline levels is considered a successful treatment outcome. An additional example of a measurable improvement or beneficial effect for an immune disorder or immune disease is an improvement in a histopathological change caused by or associated with the immune disorder or disease. For example, preventing further or reducing skeletal joint infiltration or tissue destruction, or pancreas, thymus, kidney, liver, spleen, epidermal (skin) or mucosal tissue, gut or bowel infiltration or tissue destruction.

In accordance with the invention, there are provided methods of blocking, inhibiting preventing, reducing, or decreasing binding of an OX40 ligand (OX40L) to activated T cells or OX40, in vitro or in vivo. In one embodiment, a method includes contacting activated T cells with an OX40 antibody effective to inhibit or prevent binding of an OX40 ligand to activated T cells. In another embodiment, a method includes contacting OX40 with an OX40 antibody effective to inhibit or prevent binding of an OX40 ligand to OX40. In particular aspects, a method is performed on a subject in need of blocking, reducing, decreasing, inhibiting or preventing binding of an OX40 ligand (OX40L) to activated T cells, optionally with an OX40 pharmaceutical composition.

In accordance with the invention, there are provided methods of modulating OX40-mediated cell signaling, in vitro or in vivo. In one embodiment, a method includes administering to a subject in need of modulating OX40-mediated cell signaling an OX40 antibody effective to modulate OX40-mediated cell signaling.

In accordance with the invention, there are provided methods of reducing numbers of activated, effector, memory or regulatory T cells, in vitro or in vivo. In one embodiment, a method includes administering to a subject in need of reduced numbers of activated, effector, memory or regulatory T cells an amount of OX40 antibody sufficient to reduce numbers of activated, effector, memory or regulatory T cells.

In accordance with the invention, there are provided methods of treating a disease or disorder caused by activated, effector, memory or regulatory T cells. In one embodiment, a method includes administering to a subject an amount of an OX40 antibody sufficient to reduce, decrease or prevent progression of the disease or disorder caused by activated, effector, memory or regulatory T cells, or deplete activated, effector, memory or regulatory T cells. In particular aspects, the disease or disorder comprises: graft versus host disease, inflammation or an autoimmune disorder.

In accordance with the invention, there are provided methods of decreasing the number of activated T cells in the blood, spleen, lymph nodes, intestines, liver, lung, or skin in a subject. In one embodiment, a method includes administering to the subject an amount of an OX40 antibody sufficient to decrease the number of activated T cells in the blood, spleen, lymph nodes, intestines, liver, lung, or skin. In one aspect, a method of decreasing the number of activated T cells in the blood, spleen, lymph nodes, intestines, liver, lung, or skin is in an acute or chronic xenograft host disease model.

Invention compositions and methods can be combined with any other treatment or therapy that provides a desired effect. In particular, treatments, and therapies that have been characterized as having a complementary or synergistic effect are applicable. Exemplary treatments and therapies include immune suppressive agents or drugs. Such immune-suppressive treatments and therapies can be performed prior to, substantially contemporaneously with any other methods of the invention, for example, a treatment or therapy.

The invention therefore provides combination methods in which the methods of the invention are used in a combination with any therapeutic regimen, treatment protocol or composition, such as an immune suppressive protocol, agent or drug set forth herein or known in the art. In one embodiment, a method includes administering an OX40 antibody, subsequence or fragment thereof and an immune suppressive treatment, agent or drug. The immune suppressive treatment, agent or drug can be administered prior to, substantially contemporaneously with or following administration of OX40 antibody, subsequence or fragment thereof to a subject.

As used herein, the term "immune suppressive" or grammatical variations thereof, when used in reference to a treatment, therapy, agent or drug means that the treatment, therapy, agent or drug provides an decrease, reduction, inhibition or prevention of an immune response, humoral or cell-mediated. Such therapies can suppress immune response generally or systemically, or suppress immune response in a specific region or location.

Specific non-limiting classes of immune suppressive agents and drugs include alkylating agents, anti-metabolites, plant extracts, plant alkaloids, nitrosoureas, hormones (steroids such as glucocorticoids), nucleoside and nucleotide analogues. Specific examples of immune suppressive drugs include cyclophosphamide, azathioprine, cyclosporin A, tacrolimus (FK506), rapamycin, methotrexate, FTY720, cox-2 inhibitors and interleukins (e.g., IL-12).

Polyclonal and monoclonal antibodies are a particular example of an immune suppressive treatment or therapy. Immune suppressive antibodies include, for example, infliximab (Remicade®), Rituxan®, Atgam®, and Thymoglobuline®, Xenapax®, Simulect®, Humira®, Raptiva®, Tysabri®, and Orthoclone® (OKT3).

Methods of the invention also include, among other things, methods that result in a reduced need or use of another treatment protocol or therapeutic regimen, process or remedy. For example, for inflammation, GVHD or an autoimmune disorder, a method of the invention has a therapeutic benefit if in a given subject a less frequent or reduced dose or elimination of an immune suppressive treatment or therapy results.

Thus, in accordance with the invention, methods of reducing need or use of an immune suppressive treatment or therapy are provided. In one embodiment, a method includes administering an OX40 antibody, fragment or subsequent thereof to a subject that is undergoing or has undergone an immune suppressive therapy. In one aspect, a method includes administering an OX40 antibody, fragment or subsequent thereof in an amount effective to reduce dosage, frequency or duration or eliminate need for an immune-suppressive treatment or therapy of inflammation, GVHD or an autoimmune disorder. The methods can be performed prior to, substantially contemporaneously with or following administration of an immune-suppressive treatment or therapy.

The doses or "amount effective" or "amount sufficient" in a method of treatment or therapy in which it is desired to achieve a therapeutic benefit or improvement includes, for example, any objective or subjective alleviation or amelioration of one, several or all pathologies, adverse symptoms or complications associated with or caused by the target disease, disorder, pathology or an adverse symptom or complication, to a measurable or detectable extent. Preventing, inhibiting or delaying a progression or worsening of the target disease, disorder, pathology or an adverse symptom or complication is also a satisfactory outcome. An amount sufficient or an amount effective means sufficiency or effectiveness in a particular subject, not a group of subjects or the general population. Thus, the "amount effective" or "amount sufficient" will be enough to provide a therapeutic benefit to a given subject.

An amount sufficient or an amount effective can but need not be provided in a single administration and, can but need not be, administered alone or in combination with another treatment, protocol or therapeutic regimen. For example, the amount may be proportionally increased as indicated by the need of the subject, status of the disorder, disease or condition treated or the side effects of treatment. In addition, an amount sufficient or an amount effective need not be sufficient or effective if given in single or multiple doses without a second treatment, protocol or therapeutic regimen, since additional doses, amounts or duration above and beyond such doses, or additional treatments, protocols or therapeutic regimens may be included to be effective or sufficient in a given subject. Amounts considered effective or sufficient also include amounts that result in a reduction of the use of another treatment, therapeutic regimen or protocol.

Exemplary non-limiting amounts (doses) are in a range of about 0.1 mg/kg to about 100 mg/kg, and any numerical value or range or value within such ranges. Greater or lesser amounts (doses) can be administered, for example, 0.01-500 mg/kg, and any numerical value or range or value within such ranges. Additional exemplary non-limiting amounts (doses) range from about 0.5-50 mg/kg, 1.0-25 mg/kg, 1.0-10 mg/kg, and any numerical value or range or value within such ranges.

Methods of the invention may be practiced by any mode of administration or delivery, or by any route, systemic, regional and local administration or delivery. Exemplary administration and delivery routes include intravenous, intrarterial, intradermal, intramuscular, subcutaneous, intra-pleural, transdermal (topical), transmucosal, intra-cranial, intra-spinal, intra-ocular, rectal, oral (alimentary) and mucosal.

Methods of the invention may be practiced one or more times (e.g., 1-10, 1-5 or 1-3 times) per day, week, month, or year. The skilled artisan will know when it is appropriate to delay or discontinue administration. A non-limiting dosage schedule is 1-7 times per week, for 1, 2, 3, 4, 5, 6, 7, 8, 9, 10, 15, 20 or more weeks, and any numerical value or range or value within such ranges.

Of course, as is typical for any treatment or therapy, different subjects will exhibit different responses to treatment and some may not respond or respond inadequately to a particular treatment protocol, regimen or process. Amounts effective or sufficient will therefore depend at least in part upon the disease, disorder, pathology treated (e.g., inflammation, GVHD, transplant rejection, or an autoimmune disorder, and if it is advanced, late or early stage), the therapeutic effect desired, as well as the individual subject (e.g., the bioavailability within the subject, gender, age, etc.) and the subject's response to the treatment or therapy which will be based, in part, upon genetic and epigenetic variability (e.g., pharmacogenomics). Furthermore, since every treated subject or patient may not respond to a particular treatment or therapeutic method, protocol, regimen, process or remedy, the treatment or therapeutic methods are not required to achieve a particular measurable improvement or beneficial effect, clinical endpoint or desired outcome in each and every subject or patient, or a given population so treated. Accordingly, a given subject or patient, or population may fail to respond, respond inadequately or may exhibit undesirable responses, such as a side effect, to an invention treatment or therapeutic method.

The terms "subject" and "patient" are used interchangeably herein and refer to animals, typically mammals, such as humans, non-human primates (gorilla, chimpanzee, orangutan, macaque, gibbon), domestic animals (dog and cat), farm and ranch animals (horse, cow, goat, sheep, pig), laboratory and experimental animals (mouse, rat, rabbit, guinea pig). Subjects include disease model animals (e.g., such as mice, rats and non-human primates) for studying in vivo efficacy (e.g., a GVHD animal model). Human subjects include children, for example, newborns, infants, toddlers and teens, between the ages of 1 and 5, 5 and 10 and 10 and 18 years, adults between the ages of 18 and 60 years, and the elderly, for example, between the ages of 60 and 65, 65 and 70 and 70 and 100 years.

Subjects include mammals (e.g., humans) in need of treatment, that is, they have a disease, disorder, pathology or symptom thereof that is amenable to or that may respond to treatment or therapy with an OX40 antibody, subsequence or fragment. Subjects include those having or at risk of having a chronic or acute immune disorder or disease, inflammation, GVHD, transplant rejection, inflammation, an autoimmune disease or an OX40-mediated cell response. Subjects also include those that are candidates for or have been treated for one or more of: a chronic or acute immune disorder or disease, GVHD, transplant rejection, inflammation, an autoimmune disease or an OX40-mediated cell response. Thus, a subject that is a candidate for or has received a cell, tissue or organ transplant or graft, such as a kidney, heart, lung, skin, eye blood vessel, liver or pancreas transplant, or bone marrow, hematopoietic stem cell, peripheral blood stem cells or cord blood stem cells, either allogeneic or non-allogeneic cells, neural cells, is a candidate for treatment with an OX40 antibody.

Subjects further include those in need of an immune suppressive treatment or therapy due to a lab or clinical diagnosis warranting such treatment, subjects undergoing an immune suppressive treatment or therapy (e.g., due to a transplant), and subjects having undergone an immune suppressive treatment or therapy, and are at risk of relapse or recurrence. At risk subjects include those with a family history of genetic predisposition towards, or who have suffered previously from a chronic or acute immune disease or disorder, inflammation, GVHD, transplant rejection, inflammation, an autoimmune disease or an OX40-mediated cell response. Such at risk subjects can be identified using screens, such as auto-reactive T cells or anti-self protein antibodies. For example, subjects that express rheumatoid factor are at risk for rheumatoid arthritis. Subjects that express antibodies against MBP, MOG or PLP, are at risk for multiple sclerosis.

At risk subjects can therefore be treated in order to inhibit or reduce the likelihood of developing a chronic or acute immune disease or disorder, inflammation, GVHD, transplant rejection, inflammation, an autoimmune disease, or an OX40-mediated cell response, or suffering a relapse or recurrence of a chronic or acute immune disease or disorder, inflammation, GVHD, transplant rejection, inflammation, an autoimmune disease, or an OX40-mediated cell response. The result of such treatment can be to reduce the risk of developing a chronic or acute immune disease or disorder, inflammation, GVHD, transplant rejection, inflammation, an autoimmune disease, or an OX40-mediated cell response.

The antibodies, nucleic acids, and other compositions and methods of the invention can be included in or employ pharmaceutical formulations. Such pharmaceutical formulations are useful for treatment of, or administration or delivery to, a subject in vivo locally, regionally or systemically, or ex vivo.

Pharmaceutical formulations include "pharmaceutically acceptable" and "physiologically acceptable" carriers, diluents or excipients. The terms "pharmaceutically acceptable" and "physiologically acceptable" include solvents (aqueous or non-aqueous), solutions, emulsions, dispersion media, coatings, isotonic and absorption promoting or delaying agents, compatible with pharmaceutical administration. Such formulations can be contained in a liquid; emulsion, suspension, syrup or elixir, or solid form; tablet (coated or uncoated, immediate, delayed, continuous, or pulsatile release), capsule (hard or soft, immediate, delayed, continuous, or pulsatile release), powder, granule, crystal, or microbead. Supplementary compounds (e.g., preservatives, antibacterial, antiviral and antifungal agents) can also be incorporated into the formulations.

Pharmaceutical formulations can be made to be compatible with a particular local, regional or systemic administration or delivery route. Thus, pharmaceutical formulations include carriers, diluents, or excipients suitable for administration by particular routes. Specific non-limiting examples of routes of administration for compositions of the invention are parenteral, e.g., intravenous, intrarterial, intradermal, intramuscular, subcutaneous, intra-pleural, transdermal (topical), transmucosal, intra-cranial, intra-spinal, intra-ocular, rectal, oral (alimentary), mucosal administration, and any other formulation suitable for the treatment method or administration protocol.

Solutions or suspensions used for parenteral application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Pharmaceutical formulations for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as mannitol, sorbitol, sodium chloride can be included in the composition. Including an agent which delays absorption, for example, aluminum monostearate or gelatin can prolong absorption of injectable compositions.

Sterile injectable formulations can be prepared by incorporating the active composition in the required amount in an appropriate solvent with one or a combination of above ingredients. Generally, dispersions are prepared by incorporating the active composition into a sterile vehicle containing a basic dispersion medium and any other ingredient. In the case of sterile powders for the preparation of sterile injectable solutions, methods of preparation include, for example, vacuum drying and freeze-drying which yields a powder of the active ingredient plus any additional desired ingredient from a previously prepared solution thereof.

For transmucosal or transdermal administration, penetrants appropriate to the barrier to be permeated are used in the formulation. Such penetrants are known in the art, and include, for example, for transmucosal administration, detergents, bile salts, and fusidic acid derivatives. Transmucosal administration can be accomplished through the use of nasal sprays, inhalation devices (e.g., aspirators) or suppositories. For transdermal administration, the active compounds are formulated into ointments, salves, gels, creams or patches.

The pharmaceutical formulations can be prepared with carriers that protect against rapid elimination from the body, such as a controlled release formulation or a time delay material such as glyceryl monostearate or glyceryl stearate. The formulations can also be delivered using articles of manufacture such as implants and microencapsulated delivery systems to achieve local, regional or systemic delivery or controlled or sustained release.

Biodegradable, biocompatible polymers can be used, such as ethylene vinyl acetate, polyanhydrides, polyglycolic acid, collagen, polyorthoesters, and polylactic acid. Methods for preparation of such formulations are known to those skilled in the art. The materials can also be obtained commercially from Alza Corporation (Palo Alto, Calif.). Liposomal suspensions (including liposomes targeted to cells or tissues using antibodies or viral coat proteins) can also be used as pharmaceutically acceptable carriers. These can be prepared according to known methods, for example, as described in U.S. Pat. No. 4,522,811.

Additional pharmaceutical formulations appropriate for administration are known in the art (see, e.g., Gennaro (ed.), *Remington: The Science and Practice of Pharmacy*, 20$^{th}$ ed., Lippincott, Williams & Wilkins (2000); Ansel et al., *Pharmaceutical Dosage Forms and Drug Delivery Systems*, 7$^{th}$ ed., Lippincott Williams & Wilkins Publishers (1999); Kibbe (ed.), *Handbook of Pharmaceutical Excipients American Pharmaceutical Association*, 3$^{rd}$ ed. (2000); and *Remington's Pharmaceutical Principles of Solid Dosage Forms*, Technonic Publishing Co., Inc., Lancaster, Pa., (1993)).

The compositions used in accordance with the invention, including OX40 antibodies, nucleic acids, treatments, therapies, agents, drugs and pharmaceutical formulations can be packaged in dosage unit form for ease of administration and uniformity of dosage. "Dosage unit form" as used herein refers to physically discrete units suited as unitary dosages treatment; each unit contains a quantity of the composition in association with the carrier, excipient, diluent, or vehicle calculated to produce the desired treatment or therapeutic (e.g., beneficial) effect. The unit dosage forms will depend on a variety of factors including, but not necessarily limited to, the particular composition employed, the effect to be achieved, and the pharmacodynamics and pharmacogenomics of the subject to be treated.

The invention further provides kits, including OX40 antibodies, nucleic acids, agents, drugs and pharmaceutical formulations, packaged into suitable packaging material, optionally in combination with instructions for using the kit components, e.g., instructions for performing a method of the invention. In one embodiment, a kit includes an OX40 antibody, subsequence or fragment and instructions for detecting OX40. In another embodiment, a kit includes an OX40 antibody, subsequence or fragment and instructions for treating a subject in need of treatment (e.g., a subject having a disease, disorder, pathology, or condition amendable or that may respond to treatment or therapy) with the OX40 antibody, subsequence or fragment. In one aspect, the instructions are for treating a chronic or acute immune disease or disorder, inflammation, GVHD, transplant rejection, inflammation, an autoimmune disease or an OX40-mediated cell response. In further aspects, a kit includes an immune-suppressive treatment, therapy or agent.

The term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions, for example, a diagnostic or treatment method of the invention. Instructions can therefore include instructions for practicing any of the methods of the invention described herein. Thus, in various embodiments, a kit includes a label or packaging insert including instructions for practicing a method of the invention in solution, in vitro, in vivo, or ex vivo. In one aspect, the instructions include administering or delivering the OX40 antibody, subsequence or fragment into a subject locally, regionally or systemically in a treatment or therapeutic method of the invention.

Instructions may additionally include indications of a satisfactory clinical endpoint or any adverse symptoms or complications that may occur. Instructions may further include storage information, expiration date, or any information required by regulatory agencies such as the Food and Drug Administration for use in a human subject.

The instructions may be on "printed matter," e.g., on paper or cardboard within the kit, on a label affixed to the kit or packaging material, or attached to a vial or tube containing a component of the kit. Instructions may comprise audio or video medium and additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Invention kits can additionally include a buffering agent, a preservative, or a stabilizing agent. The kit can also include control components for assaying for activity, e.g., a control sample or a standard. Each component of the kit can be enclosed within an individual container or in a mixture and all of the various containers can be within single or multiple packages.

In accordance with the invention further provided are cell-free (e.g., in solution, in solid phase) and cell-based (e.g., in vitro or in vivo) methods of screening, detecting and identifying OX40. The methods can be performed in solution, in vitro using a biological material or sample, and in vivo, for example, a sample of cells (e.g., lymphocytes) from an animal. In one embodiment, a method includes contacting a biological material or sample with an antibody that binds to OX40 under conditions allowing binding of the antibody OX40; and assaying for binding of the antibody to OX40. The binding of the antibody to OX40 detects the presence of OX40. In one aspect, OX40 is present on a cell or tissue. In another aspect, the biological material or sample is obtained from a mammalian subject The term "contacting," when used in reference to a composition such as a protein (e.g., OX40 antibody), material, sample, or treatment, means a direct or indirect interaction between the composition (e.g., OX40 antibody) and the other referenced entity. A particular example of direct interaction is binding. A particular example of an indirect interaction is where the composition acts upon an intermediary molecule, which in turn acts upon the referenced entity. Thus, for example, contacting a cell (e.g., a lymphocyte) with an OX40 antibody includes allowing the antibody to bind to the cell (e.g., through binding to OX40), or allowing the antibody to act upon an intermediary that in turn acts upon the cell.

The terms "assaying" and "measuring" and grammatical variations thereof are used interchangeably herein and refer to either qualitative or quantitative determinations, or both qualitative and quantitative determinations. When the terms are used in reference to binding, any means of assessing the relative amount, affinity or specificity of binding is contemplated, including the various methods set forth herein and known in the art. For example, OX40 antibody binding to OX40 can be assayed or measured by an ELISA assay.

Unless otherwise defined, all technical and scientific terms used herein have the same meaning as commonly understood by one of ordinary skill in the art to which this invention relates. Although methods and materials similar or equivalent to those described herein can be used in the practice or testing of the invention, suitable methods and materials are described herein.

All publications, patents, Genbank accession numbers and other references cited herein are incorporated by reference in their entirety. In case of conflict, the present specification, including definitions, will control.

As used herein, singular forms "a", "and," and "the" include plural referents unless the context clearly indicates otherwise. Thus, for example, reference to "an antibody" includes a plurality of antibodies and reference to "a treatment or therapy" can include multiple, sequential or simultaneous treatments or therapies, and so forth.

As used herein, all numerical values or numerical ranges include whole integers within or encompassing such ranges and fractions of the values or the integers within or encompassing ranges unless the context clearly indicates otherwise. Thus, for example, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. In another example, reference to a range of 1-5,000 fold includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and so forth.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed.

A number of embodiments of the invention have been described. Nevertheless, it will be understood that various modifications may be made without departing from the spirit and scope of the invention. Accordingly, the following examples are intended to illustrate but not limit the scope of invention described in the claims.

The Substitute Sequence Listing submitted herewith in computer readable form is incorporated herein by reference.

EXAMPLES

Example 1

This example describes various materials and methods.

Antigen preparation: RNA was isolated from human peripheral blood mononuclear cells activated for two days with phytohemaglutinin (PHA, Remel, Lenexa, Kans.) using Tri Reagent (Invitrogen Corp., Carlsbad, Calif.). The sequence encoding the extracellular domain of human OX40 was amplified by reverse-transcription polymerase chain reaction. The amplified product was sequenced and confirmed to be identical to the published sequence of human OX40 (WO95/12673, SEQ NO:1). The product was subcloned in frame into the pfastbac-hFc baculovirus donor plasmid. This vector was generated from the pfastbac plasmid (Invitrogen Corp.) and the Fc portion of human IgG1 ("hIgG1"). The hIgG1 sequence was excised from the pV11392.fc vector. Recombinant baculovirus were generated that encoded the human OX40:hIgG1 fusion protein (hOX40: hFc). *Trichoplusia ni* High-Five BTI-TN-5b1-4 ("Tn5") insect cells (Invitrogen Corp.) were infected with the hOX40: hFc recombinant baculovirus for protein production. The full-length OX40 sequence was amplified and cloned into the pCDNA3.1 vector (Invitrogen Corp.) for expression in eucaryotic cells. EL-4 (ATCC TIB-39) and CHO-K1 (ATCC CCL-61) cells were transfected using lipofectamine 2000 (Invitrogen Corp.) and stable transfectants were selected using hygromycin B (Fisher Scientific, Pittsburgh, Pa.) or geneticin (Invitrogen Corp.), respectively. hOX40:hFc was conjugated to ovalbumin by glutaraldehyde coupling. One mg of hOX40:hFc was mixed with 0.5 mg of ovalbumin (Pierce, Rockford, Ill.) in 1 ml phosphate buffered saline (PBS). 50 µl of 1% EM grade gluataraldehyde (Sigma, St. Louis, Mo.) was slowly added and gentle shaking for five minutes mixed the solution. After three hours at room temperature 50 µl of 1 M ethanolamine (pH 7) was added and the solution was incubated for two more hours followed by buffer exchange on a NAP10 column (Amersham Biosciences, Piscataway, N.J.) with phosphate buffered saline.

Nucleotide sequence of human OX40:human IgG1 fusion protein from initiation codon (ATG) through human OX40 extracellular domain to end of human Fc sequence (underlined) SEQ ID NO:1

```
ATGTGCGTGG GGGCTCGGCG GCTGGGCCGC GGGCCGTGTG CGGCTCTGCT CCTCCTGGGC   60

CTGGGGCTGA GCACCGTGAC GGGGCTCCAC TGTGTCGGGG ACACCTACCC CAGCAACGAC  120

CGGTGCTGCC ACCAGTCCAG GCCAGGCAAC GGGATGGTGA GCCGCTGCAG CCGCTCCCAG  180

AACACGGTGT GCCGTCCGTG CGGGCCGGGC TTCTACAACG ACGTGGTCAG CTCCAAGCCG  240

TGCAAGCCCT GCACGTGGTG TAACCTCAGA AGTGGGAGTG AGCGGAAGCA GCTGTGCACG  300

GCCACACAGG ACACAGTCTG CCGCTGCCGG GCGGGCACCC AGCCCCTGGA CAGCTACAAG  360

CCTGGAGTTG ACTGTGCCCC CTGCCCTCCA GGGCACTTCT CCCCAGGCGA CAACCAGGCC  420

TGCAAGCCCT GGACCAACTG CACCTTGGCT GGGAAGCACA CCCTGCAGCC GGCCAGCAAT  480

AGCTCGGACG CAATCTGTGA GGACAGGGAC CCCCCAGCCA CGCAGCCCCA GGAGACCCAG  540

GGCCCCCCGG CCAGGCCCAT CACTGTCCAG CCCACTGAAG CCTGGCCCAG AACCTCACAG  600

GGACCCTCCA GATCTTGTGA CAAAACTCAC ACATGCCCAC CGTGCCCAGC ACCTGAACTC  660

CTGGGGGGAC CGTCAGTCTT CCTCTTCCCC CCAAAACCCA AGGACACCCT CATGATCTCC  720

CGGACCCCTG AGGTCACATG CGTGGTGGTG GACGTGAGCC ACGAAGACCC TGAGGTCAAG  780

TTCAACTGGT ACGTGGACGG CGTGGAGGTG CATAATGCCA AGACAAAGCC GCGGGAGGAG  840

CAGTACAACA GCACGTACCG TGTGGTCAGC GTCCTCACCG TCCTGCACCA GGACTGGCTG  900

AATGGCAAGG AGTACAAGTG CAAGGTCTCC AACAAAGCCC TCCCAGCCCC CATCGAGAAA  960

ACCATCTCCA AAGCCAAAGG GCAGCCCCGA GAACCACAGG TGTACACCCT GCCCCCATCC 1020

CGGGATGAGC TGACCAAGAA CCAGGTCAGC CTGACCTGCC TGGTCAAAGG CTTCTATCCC 1080

AGCGACATCG CCGTGGAGTG GGAGAGCAAT GGGCAGCCGG AGAACAACTA CAAGACCACG 1140

CCTCCCGTGC TGGACTCCGA CGGCTCCTTC TTCCTCTACA GCAAGCTCAC CGTGGACAAG 1200

AGCAGGTGGC AGCAGGGGAA CGTCTTCTCA TGCTCCGTGA TGCATGAGGC TCTGCACAAC 1260

CACTACACGC AGAAGAGCCT CTCCCTGTCT CCGGGTAAAT GA                    1320
```

Amino acid sequence of human OX40-extracellular domain fused to the Fc portion of human IgG1 (underlined) SEQ ID NO:2

```
MCVGARRLGR GPCAALLLLG LGLSTVTGLH CVGDTYPSND RCCHECRPGN GMVSRCSRSQ   60

NTVCRPCGPG FYNDVVSSKP CKPCTWCNLR SGSERKQLCT ATQDTVCRCR AGTQPLDSYK  120

PGVDCAPCPP GHFSPGDNQA CKPWTNCILA GKHTLQPASN SSDAICEDRD PPATQPQETQ  180

GPPARPITVQ PTEAWPRTSQ GPSRSCDKTH TCPPCPAPEL LGGPSVFLFP PKPKDTLMIS  240

RTPEVTCVVV DVSHEDPEVK FNWYVDGVEV HNAKTKPREE QYNSTYRVVS VLTVLHQDWL  300

NGKEYKCKVS NKALPAPIEK TISKAKGQPR EPQVYTLPPS RDELTKNQVS LTCLVKGFYP  360

SDIAVEWESN GQPENNYKTT PPVLDSDGSF FLYSKLTVDK SRWQQGNVFS CSVMHEALHN  420

HYTQKSLSLS PGK                                                    433
```

Mice: Human trans-chromosomic KM Mice™ (WO 02/43478, WO 02/092812, Ishida, et al., IBC's 11th Antibody Engineering Meeting. Abstract (2000); Kataoka, S. IBC's 13th Antibody Engineering Meeting. Abstract (2002)) harboring human chromosome fragments encoding the human immunoglobulin region were obtained from Kirin Brewery Co., Ltd., Japan, and were housed in the animal facility at the La Jolla Institute for Allergy and Immunology. An overview of the technology for producing human antibodies is described in Lonberg (Lonberg, et al., Int Rev Immunol 13(1): 65-93 (1995)). Transgenic animals with one or more human immunoglobulin genes (kappa or lambda) that do not express endogenous immunoglobulins are described, for example in, U.S. Pat. No. 5,939,598. Additional methods for producing human antibodies and human monoclonal antibodies are described (see, e.g., WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598). Development of bovine carrying human immunoglobulin genes, TC cows, is described in (Kuroiwa, et al., *Nat Biotechnol* 20(9): 889-94 (2002); Kuroiwa, et al., *Nat Genet* 36(7): 775-80 (2004)). *Immunization*: hOX40:hFc recombinant protein was mixed with an equal volume of complete Freund's adjuvant (CFA, Sigma) and an emulsion was prepared. Mice were immunized with 10 to 25 µg of protein intraperitoneally and were boosted intraperitoneally with 5 to 10 µg of protein emulsified in incomplete Freund's adjuvant (IFA, Sigma) at two week intervals for 2 to 4 boosts. A final intraperitoneal injection of 5 to 10 µg of soluble hOX40:hFc without adjuvant was given five days prior to fusion. Another group of mice was immunized with hOX40:hFc that was heat denatured by incubation at 80° C. for ten minutes in PBS then mixed 1:1 with RIBI adjuvant (Sigma). Mice were immunized as described above. A third group of mice was immunized with hOX40:hFc conjugated to ovalbumin. The mice were either primed with 30 µg of hOX40:hFc-OVA alone or in a mixture with hOX40:hFc, 10 µg and 20 µg respectively, in RIBI. The former received a boost of 30 µg hOX40:hFc-OVA in RIBI, followed by 10 µg of hOX40:hFc in RIBI at two week intervals. A final boost of 20 µg hOX40:hFc-OVA in PBS was given five weeks later. The latter group's two boosts consisted of 5 µg hOX40:hFc-OVA+10 µg hOX40:hFc in RIBI at two week intervals, with a final boost of 10 µg hOX40:hFc in PBS. All injections were intraperitoneal. A final group of mice was immunized with CD4+ human T cells that had been stimulated for two days with PHA (1 µg/ml) and recombinant human interleukin 2 (IL2, 10 ng/ml, BD Pharmingen, San Diego, Calif.). Prior to injection the cells received 25 Gy of irradiation from a cesium source and were diluted 1:1 in RIBI adjuvant.

Hybridoma production: The mice with the highest anti-OX40 IgG specific antibody titer in their serum were selected for the production of monoclonal antibodies. The spleens were harvested and single cell suspensions were fused to a myeloma cell line (SP2/O-Ag14) (ATCC, Rockville, Md.) at a ratio of 3:1 with 50% polyethylene glycol (Boehringer Mannheim, Indianapolis, Ind.). The fusions were plated into 96 well flat bottom plates at an optimal density and cultured in complete DMEM-10 medium (Dulbecco's Modified Engle's Medium with 10% fetal bovine serum (FBS, Invitrogen Corp.)), 1% non-essential amino acids, 2 mM L-glutamine, 100 U/ml penicillin, 100 µg/ml streptomycin sulfate (all from BioWhittaker, Walkersville, Md.), HAT supplement (Sigma), and 10% Hybridoma Cloning Factor (HCF, Biovaris, San Diego, Calif.) in a 10% $CO_2$, 37° C. incubator. Approximately 4000 wells from four fusions were screened by ELISA for human kappa containing OX40 specific antibodies. Human anti-human OX40 IgG antibodies were confirmed by flow cytometric analysis. Positive wells were expanded and subjected to three to four rounds of limiting dilution cloning to obtain monoclonal antibodies.

Antibody and protein purification: For antibody purification, hybridomas were cultured in 2 liter roller bottles at 350 milliliter to 1 liter/bottle or in a 1 liter Integra system (INTEGRA Bioscience, Inc. Ijamsville, Md.) with hybridoma-SFM medium (Invitrogen Corp.) supplemented with ultra low IgG fetal bovine serum (Invitrogen Corp.). Human OX40:hFc recombinant protein was generated by infecting 1 liter of Tn5 cells for four days. Human monoclonal antibodies and OX40:hFc were purified from culture media using recombinant Protein A-Sepharose Fast Flow gel (Amersham Biosciences). Conditioned medium generated in roller bottles was first concentrated using an Ultrasette tangential flow system (Pall Corp., East Hills, N.Y.). The conditioned medium was filtered with a 0.22 µm vacuum filter unit (Millipore, Bedford, Mass.) and loaded onto a Protein A-Sepharose Fast Flow column (Amersham Biosciences) of appropriate size for the amount of human antibody in the medium. The column was washed thoroughly with 20 column volumes of PBS and the antibody was eluted with 0.1 M Gly-HCl, pH 3.6, 0.15 M NaCl and neutralized with 1 M Tris-HCl, pH 8.0. The fractions were analyzed by SDS-PAGE and the positive fractions were pooled and concentrated with a centrifugal concentrator (Vivaspin, 50,000 MWCO: Sartorius, Gettingen, Germany). Sephadex G-25 desalting columns, (NAP, Amersham Biosciences), were used for buffer exchange to PBS, pH 7.4. Finally, the antibody was filter sterilized using syringe filters with 0.22 µm pore diameters and the antibody concentration was determined by the Lowry method. Pyrogen content was determined using a Limulus Amebocyte Lysate ("LAL") assay (Associates of Cape Cod, Falmouth, Mass.). The limits of detection of this assay are 0.06 EU/mg. If the test was negative, the samples were considered endotoxin free.

Human IgG Quantitation ELISA: To determine the amount of human antibody present in supernatants and purified stocks the following protocol was used. Goat anti-human Fcγ specific antibody (Jackson Immunoresearch Laboratories, West Grove, Pa.) was coated to the 96 well plates (Nunc, Denmark) in carbonate buffer at 0.5 µg/well for one hour at 37° C. The plates were then blocked with Superblock (Pierce, Rockford, Ill.) for 30 minutes followed by addition of the samples to the plates. Standard curves were generated using total human IgG (Sigma) or purified human IgG1 or IgG4 (Kirin Brewery Co., Ltd). The plates were incubated for one hour at 37° C., washed in PBS/1% BSA/0.1% Tween20 (Sigma), and the bound antibody was detected with goat anti-human Fcγ specific antibody conjugated to horseradish peroxidase (HRP, Jackson Immunoresearch) for one hour at 37° C. The TMB substrate (Sigma) was added for 10 minutes and the reaction was stopped with $H_2SO_4$ (LabChem Inc., Pittsburgh, Pa.). The optical density (OD) was measured at 450 nm on a microplate reader.

OX40 Specific Antibody Detection ELISA: Antibody titers, specificity, and production by hybridomas were determined by ELISA. In brief, 96 well flat bottom plates were coated with 50 µl of hOX40:hFc at 5 µg/ml in carbonate buffer (pH 9.4) overnight at 4° C. or at 37° C. for one hour. After washing twice with PBS/0.1% Tween 20, plates were blocked with PBS/1% BSA/0.1% Tween20 at 37° C. for one hour. The serum, supernatant, or purified antibody was diluted in blocking buffer, added to the wells, and the plates were incubated for one hour at 37° C. The plates were washed four times with PBS/0.1% Tween 20 and the peroxidase conjugated sheep anti-human kappa detection antibody (The Binding Site, Birmigham, UK) was added at a dilution of 1:2000. Following one hour incubation at 37° C., the plates were washed and the TMB (Sigma) substrate was added and incubated at room temperature for ten to thirty minutes. The reaction was stopped with $H_2SO_4$ (LabChem) and the optical density was measured at 450 nm by a microplate reader.

Flow Cytometry: Antibody titers, specificity, and relative binding affinities were determined by flow cytometric analysis using human OX40 stable CHO-K1 transfectants or three day PHA+IL2 activated human PBMC. The cells were washed once in staining buffer: PBS+2% FBS+0.1% $NaN_3$+10 mM EDTA, then resuspended in serum, supernatant, or purified antibodies in a volume of 50 µl. The cells were incubated with the antibodies on ice for twenty minutes, washed twice in staining buffer, then resuspended in an anti-human IgG-phycoerythrin labeled secondary antibody. Two different antibodies were used: (1) goat anti-human IgG (Southern Biotechnology Associates, Birmingham, Ala.) or (2) mouse anti-human IgG (BD Pharmingen, San Diego, Calif.). Following twenty minute incubation on ice, the cells were washed once and fixed ten minutes with 1% paraformaldehyde. After a final wash the cells were resuspended in staining buffer and the samples were acquired using FACScan or FACS Calibur flow cytometers (Becton Dickinson Biosciences, Palo Alto, Calif.), and the data were analyzed using Cellquest (Becton Dickinson Biosciences) or Flow Jo (Tree-Star, Inc., San Carlos, Calif.) software. The activated T cells were also stained with mouse anti-human OX40 antibody L106 (Becton Dickinson), which was directly conjugated to phycoerythrin or whose binding was detected with anti-mouse IgG-PE (Southern Biotechnology Associates.)

OX40L Blocking Assays: To determine if the anti-human OX40 antibodies could block OX40L binding to soluble OX40 both ELISA and flow cytometric protocols were used. In the ELISA 96 well Nunc flat bottom plates were coated with recombinant soluble hOX40:hFc at 2 µg/ml in carbonate buffer (pH9.4) for one hour at 37° C. The plates were washed with PBS/0.1% Tween 20 and Superblock (Pierce) was added to the wells to block non-specific binding. The test antibodies were diluted to 1 µg/ml in PBS/Tween and added to the plates. After one hour incubation at 37° C., FLAG tagged recombinant soluble human OX40L (Alexis Biochemicals, San Diego, Calif.) was added to the appropriate wells without washing out the anti-OX40 antibodies. Following one hour incubation, the plates were washed and an anti-FLAG-peroxidase conjugated antibody (Sigma) was added to the wells for one hour at 37° C. The TMB substrate was added, after ten minutes the reaction was stopped with $H_2SO_4$, and the results were read at 450 nm using a microplate reader. In the flow cytometric assay, human CD4+ T cells were purified and activated with PHA+IL2 for two days. The cells were washed and resuspended in staining buffer and then incubated with increasing amounts of human anti-human OX40 antibodies for twenty minutes on ice, from 0.005-50 µg/ml. Soluble recombinant OX40L-FLAG was then added to the cells. The cells were washed and incubated with anti-FLAG conjugated to PE (Sigma). After another wash, the cells were fixed with 1% paraformaldehyde and analyzed on a FACScan or FACScalibur. The percent inhibition was determined using the OD or percent positive in the following formula: % inhibition=100−((sample/Maximum binding)*100).

Anti-OX40 Antibody Cross-blocking Assays: In order to determine if the antibodies bind the same "epitope" of human OX40 an ELISA protocol was used. Nunc 96 well flat bottom ELISA plates were coated with the human anti-human OX40 antibodies in carbonate buffer at 2 µg/ml for one hour at 37° C. The plates were washed and then blocked with PBS/1% BSA/Tween 20. Two to 20 µg/ml of the human anti-human OX40 antibodies and the mouse anti human-OX40 antibodies L106 (BD Biosciences, San Jose, Calif.), clone 315 (Nichirei Biosciences, Tokyo, Japan), or ACT35 (BD Pharmingen) were then pre-incubated with 2 µg/ml recombinant human OX40:mFc fusion protein (Alexis Corporation, San Diego, Calif.) for thirty minutes at room temperature. The combinations of antibody-OX40:mFc protein were added to the plate and incubated for one hour at 37° C. After three washes, bound OX40:mFc was detected with peroxidase conjugated sheep anti-mouse Ig (Amersham Biosciences). The ELISA was completed as described above. The percent inhibition was determined using the OD of each sample in the following formula: % inhibition=100−((sample/Maximum binding) *100). To determine if these human anti-human OX40 antibodies block the mouse anti-human OX40 antibodies a variation of this ELISA was performed. The method was the same except the mouse anti-human OX40 antibodies were coated on the plates and 112V8, 112F32, 112Y131, and 112Z5 were pre-incubated with human OX40:hFc protein. Binding of the OX40 protein to the coated antibodies was detected with a sheep anti-human IgG-horseradish peroxidase secondary antibody (Amersham Biosciences).

A flow cytometric assay was also used to determine if the antibodies crossblock one another. Human CD4 T cells were purified from peripheral blood mononuclear cells as described below and activated with 1 µg/ml phytohemaglutinin (Remel, Lenexa, Kans.) and 10 ng/ml recombinant human interleukin 2 (BD Pharmingen) for two to three days. The cells were washed and labeled with 10 µg/ml of the test antibodies for thirty minutes on ice in PBS supplemented with 2% fetal calf serum, and 0.1% sodium azide. Without washing, biotinylated versions of the same antibodies were added to the wells at 10 µg/ml and the cells were incubated for another thirty minutes on ice. The cells were then washed by addition of buffer and spinning at 1200 RPM for three minutes at 4° C. Binding of the biotinylated antibodies was detected by incubation with streptavidin-phycoerythrin (SA-PE, BD Pharmingen) for twenty minutes followed by another wash as described. The cells were fixed ten minutes in 1% parafomaldehyde. After a final wash the cells were resuspended in staining buffer and the samples were acquired using a FACS Calibur flow cytometer (Becton Dickinson Biosciences, Palo Alto, Calif.). The data were analyzed using Cellquest (Becton Dickinson Biosciences) or Flow Jo (Tree-Star, Inc., San Carlos, Calif.) software. The antibodies tested included 112F32, 112V8, 112Y55, 112Y131, 112Z5, anti-DNP (human IgG1 negative control), mouse anti-human OX40 antibodies, clone L106 clone 315, and clone ACT35. The percent inhibition was determined using the following formula: 100−(Geometric mean of test antibody/Max Geometric mean)*100. The antibodies were tested for inhibition of binding of themselves as well as each other.

Purification of human PBMC from whole blood: Whole blood was collected from healthy donors between the ages of 18 and 50 by the normal blood donor program at Scripps Green Hospital (La Jolla, Calif.). Heparin was added to prevent clotting. No race, ethnicity, or gender was specified. The blood was diluted in PBS and then underlayed with Ficoll-Plaque Plus (Amersham Biosciences). The mononuclear cells were separated from the serum and platelets by centrifugation at 1800 RPM without the brake. The interface containing the PBMC was collected and washed two times with PBS.

Purification of CD4+ T cells: Human CD4+ T cells were purified using a negative isolation kit from Miltenyi Biotec. (Auburn, Calif.). The PBMC were labeled with the hapten conjugated antibody mix specific for CD8, CD11b, CD16, CD19, CD36, and CD56 for fifteen minutes at 4° C. in PBS/ 0.5% BSA/2 mM EDTA. After washing twice the cells were resuspended in the anti-hapten magnetic beads (MACS beads) and the cells were incubated at 4° C. for fifteen minutes. The cells were then washed and applied to a LS/VS+ column that had been pre-washed and inserted in the magnet. The column was washed three times with buffer. The "untouched" CD4+ cells were contained in the flow through from the column. Purity was confirmed by flow cytometric analysis using antibodies specific for human CD3 and human CD4, both directly conjugated to fluorochromes (BD Pharmingen). Alternatively, CD4+ cells were positively selected with CD4 microbeads (Miltenyi Biotec.) The procedure was similar to that described above except that the cells that adhered to the column were eluted by removing the column from the magnet and forcing 5 ml of buffer through the column with a plunger.

Mixed Lymphocyte Reaction Assay: PBMC from two donors were purified and $1\times10^5$ cells from each donor were added to a 96 well U bottom plate in the presence or absence of human anti-human OX40 antibodies or negative control human IgG4 (anti-human serum albumin, Kirin Brewery Co., Ltd.) (Ukyo, et al., *Immunology* 109(2):226 (2003)). Antibodies were tested from 0.005 to 100 µg/ml, depending on the study. Multiple donor pairs were tested. The media used was RPMI-1640 supplemented with 10% human AB serum (MP Biomedical, Irvine, Calif.), penicillin/streptomycin, L-glutamine, and 2-mercaptoethanol. At day six 1 µCi tritiated thymidine ($^3$HTdR) was added to each well for the last eighteen hours of culture. The cells were lysed and transferred to glass filter mats, which were counted using a scintillation counter (Wallac, Turku, Finland).

Acute Graft Versus Host Disease In Vivo Model: Severe combined immunodeficient (SCID) male mice aged five to ten weeks were injected with 20 µg rat anti-mouse IL2 receptor β chain antibody (TMβ1, Tanaka, et al., *J Exp Med* 178(3): 1103-7 (1993)) to deplete endogenous natural killer cells. The next day the mice received 2.5 Gy of irradiation using a cesium source. Four hours later the mice received 10 million total human PBMC in PBS by intraperitoneal injection followed immediately by intravenous injection of human anti-human OX40 or negative control hIgG1 (anti-di-nitro-phenol (anti-DNP), Kirin Brewery Co. Ltd.) antibodies at 2, 20, 100, or 200 µg in 100 µl PBS. Alternatively, antibody treatment was delayed until day three or six to test the therapeutic potential of the anti-OX40 antibodies. Mice were weighed every three to four days and received the anti-IL2Rβ antibody weekly. At day twelve the mice were killed and assessed for gross pathology. Spleens were removed for flow cytometric analysis, livers and intestines for histology, and serum was collected for human cytokine and antibody analysis (Watanabe, et al., *Clin. Immunol.* 120:247 (2006)). *Chronic Graft Versus Host Disease In Vivo Model*: A model of chronic GVHD was adapted from the acute xenogenic GVHD model (Watanabe, et al., *Clin. Immunol.* 120:247 (2006)). Disease was induced by the transfer of positively selected human CD4 T cells into SCID mice that were prepared in the same was as described above. Mice received one million positively selected CD4 T cells by intraperitoneal injection at day 0 and 2, 20, or 100 µg anti-OX40 or control antibodies by intravenous injection weekly starting at day 0. Disease was evident by day thirty and mice were assessed at day forty-eight. Spleen and lymph nodes were removed for flow cytometry, skin and lung for histology, and serum for human cytokine analysis.

Human Cytokine Analysis: A panel of eight human cytokines in mouse serum was measured using multiplex technology and following the manufacturer's instructions (Bio-Rad Laboratories, Hercules, Calif.).

Purification of Human Natural Killer Cells: Human natural killer ("NK") cells were purified using a negative isolation kit from Miltenyi Biotec. (Auburn, Calif.). The PBMC were labeled with the biotin conjugated antibody mix specific for T cells, B cells, stem cells, dendritic cells, monocytes, granulocytes, and erythroid cells for fifteen minutes at 4° C. in PBS/0.5% BSA/2 mM EDTA. This was followed by the addition of anti-biotin magnetic beads ("MACS beads"). The cells were incubated at 4° C. for fifteen minutes then washed and applied to a LS/VS+ column that had been pre-washed and inserted in the magnet. The column was washed three times with buffer. The "untouched" CD56+ NK cells were contained in the flow through from the column. Purity was confirmed by flow cytometric analysis using antibodies specific for human CD56 and human CD3, both directly conjugated to fluorochromes (BD Pharmingen.)

Antibody Dependent Cell Cytotoxicity Assay (ADCC): NK cells were purified from human PBMC and cultured for forty-eight hours with 20 ng/ml recombinant human interleukin 2 (BD Pharmingen) in RPMI-1640 supplemented with 10% human AB serum (MP Biomedical, Irvine, Calif.), penicillin/streptomycin, L-glutamine, and 2-mercaptoethanol. These cells were used as effector cells in the Cytotox 96 non-radioactive cytotoxic assay (Promega Corp., Madison, Wis.). The target cells were parental or human OX40 transfected EL-4 cells. Five thousand target cells were incubated with 0.005-10 µg/ml of the anti-human OX40 antibodies or control antibodies for thirty minutes on ice in a round bottom 96 well tissue culture plate. Twenty times as many effector NK cells were added to the wells in a final volume of 100 µl and the plates were spun at 200×g for three minutes before incubation at 37° C. with 5% $CO_2$ for four hours. The plates were spun at 250×g for five minutes and 50 µl of the supernatants were transferred to an ELISA plate. The assay buffer was added to the plates in a volume of 50 µl. Following a thirty minute incubation at room temperature, 50 µl of the stop solution was added to the wells and the absorbance at 490 nm was determined. The controls required included target cells alone (spontaneous), target cells alone treated with lysis buffer for the last forty-five minutes of the incubation (maximum), effector cells alone, wells containing media alone with (volume correction) and without the addition of the lysis buffer. The percent specific lysis is determined using the following formula, after the media background is subtracted from all wells, and the volume correction value is subtracted from the target maximum value. Percent Cytotoxicity=((experimental−effector spontaneous−target spontaneous)/(target maximum−target spontaneous))*100.

Isolation of Human Anti-OX40 Antibody Genes: Cultured hybridoma cells (112V8 (ATCC No. PTA-7219, deposited Nov. 17, 2005)), which produce 112V8 antibody (IgG4), were collected by centrifugation. Total RNA was purified from these cells using RNeasy kit (QIAGEN Inc., Valencia, Calif.) following the manufacturer's instructions. SMART RACE™ cDNA Amplification Kit (Clontech Co., Ltd., Palo Alto, Calif.) was used for cloning of cDNA that encodes the variable region of the immunoglobulin genes from total hybridoma cell RNA. Briefly, first strand cDNA was prepared by reverse transcriptase from two micrograms of RNA. This cDNA was used as a template for polymerase chain reaction ("PCR") to amplify the variable region and a part of the constant region of heavy and light chains ("HV" and "LV," respectively). The amplified sequences also contained the leader sequences. The reaction was as follows: 2.5 U Pfu Ultra DNA polymerase (Stratagene, La Jolla, Calif.); 0.2 µM 3' Primer (for Heavy chain: IgG1p, for Light chain: hk5, Table 1); 1× Universal Primer Mix A for the 5' end (UMP primer Mix A included in the SMART RACE Kit); 200 μM dNTP mix; 1 mM MgCl$_2$; Pfu Ultra Buffer (final concentration is 1×); and cDNA template.

The thermocycling program was five cycles of: 94° C.×30 seconds, 72° C.×3 minutes. Five cycles of: 94° C.×30 seconds, 70° C.×30 seconds, 72° C.×3 minutes. Twenty-five cycles of: 94° C.×30 seconds, 68° C.×30 seconds, 72° C.×3 minutes followed by an extension at 72° C.×7 minutes. Amplified DNA fragments were collected by agarose gel electrophoresis, and purified by QIAquick Gel Extraction Kit (Qiagen Co., Ltd., Germany). Purified DNA fragments of HV and LV were integrated into pCR4 Blunt-TOPO vector using the Zero Blunt TOPO PCR Cloning Kit (Invitrogen Corp.), and each construct plasmid was transformed into *E. coli*, and then cloned. Nucleotide sequences of each insert (HV and LV) in the construct plasmids were analyzed using specific primers (M13F, M13R, Table 1). Based on the sequence obtained from HV and LV, oligonucleotide primers were designed to amplify VH (V8H38, V8H39) and VL (V8L42, V8L43). (Table 1).

112V8 VH and VL were cloned into the IgG1 expression vector. Briefly, oligonucleotide primers, containing 5'-SalI and 3'-NheI restriction enzyme recognition sites were designed to amplify the variable region of the I-TV by PCR. PCR was performed using pTopoV8VH miniprep DNA as a template, V8H38 and V8H39 as primers (Table 1) with Pfu Ultra DNA polymerase. After digestion of the PCR product with NheI and SalI, a 410 bp fragment was subcloned into the IgG1 expression vector (IDEC Pharmaceuticals, San Diego, Calif., N5KG1-Val Lark (a modified vector of N5KG1, U.S. Pat. No. 6,001,358)) that was pre-digested with NheI and SalI (8.9 kilobases DNA fragment). The existence of variable region of the HV was analyzed by restriction digest.

As the second step, LV was inserted into N5KG1-Val Lark-VH vector as follows: the DNA vector was digested by two DNA restriction enzymes, BglII and BsiWI. The 9.1 kb DNA fragment was isolated. Similarly to the Heavy chain construct, a primer set for PCR of LV was designed to contain the recognition sites for 5'BglI and 3'BsiWi. These primers, V8L42 and V8L43, were used to amplify VL from the pTopoV8VL miniprep plasmid DNA. The PCR product was digested with BglII and BsiWI and isolated by agarose gel electrophoresis and gel purification. This fragment, containing V8VL, was ligated to the prepared 9.1 kb vector with T4 DNA ligase and used to transform Top10 cells (Invitrogen Corp.). Positive *E. coli* transformants were selected. This expression vector, pG1K112V8, was purified, and the presence of both 112V8LV and 112V8HV regions were confirmed by restriction analysis.

112Y55 (ATCC No. PTA-7220, deposited on Nov. 17, 2005), 112Y131 (ATCC No. PTA-7218, deposited on Nov. 17, 2005), and 112Z5 (ATCC No. PTA-7216, deposited on Nov. 17, 2005) HV and LV variable regions were isolated and sequenced using the same protocol. The primers used for amplification of the specific HV and LV are listed in Table 1.

The subclass of an antibody in part determines secondary effector functions, such as complement activation or Fc receptor (FcR) binding and antibody dependent cell cytotoxicity (ADCC) (Huber, et al., *Nature* 229(5284): 419-20 (1971); Brunhouse, et al., *Mol Immunol* 16(11): 907-17 (1979)). In identifying the optimal type of antibody for a particular application, the effector functions of the antibodies can be taken into account. For example, hIgG1 antibodies have a relatively long half life, are very effective at fixing complement, and they bind to both FcRI and FcRII. In contrast, human IgG4 antibodies have a shorter half life, do not fix complement and have a lower affinity for the FcR. Replacement of serine 228 with a proline (S228P) in the Fc region of IgG4 reduces heterogeneity observed with hIgG4 and extends the serum half life (Kabat, et al., *Sequences of proteins of immunological interest* 5$^{th}$ Edition (1991); Angal, et al., *Mol Immunol* 30(1): 105-8 (1993)). A second mutation that replaces leucine 235 with a glutamic acid (L235E) eliminates the residual FcR binding and complement binding activities (Alegre, et al., *J Immunol* 148(11): 3461-8 (1992)). The resulting antibody with both mutations is referred to as IgG4PE. The numbering of the hIgG4 amino acids was derived from Kabat (Kabat, et al., *Sequences of proteins of immunological interest* 5$^{th}$ Edition (1991)).

A vector expressing recombinant 112V8 IgG4PE was generated by digesting pG1K112V8 with NheI and BglII to release the fragment containing 112V8VH and 112V8VL. This was ligated to the IgG4PE expression vector (pN5KG4PE-Lark, IDEC Pharmaceuticals, U.S. Pat. No. 6,001,358) cut with the same enzymes. The resulting plasmid, pG4PEK112V8, was confirmed by restriction digest.

RNA from 112F32 hybridoma (ATCC No. PTA-7217, deposit date Nov. 17, 2005) was used to generate vectors to produce recombinant 112F32G1 and 112F32G4 antibodies in the same manner, the 3' primers used for amplification of the heavy and light chain genes in the RACE reactions were HH-2 and HK-2, respectively. Amplification of the 112F32HV was performed using H725' and M2H3'. The 112F32LV amplification primers were F32K5' and K52D3' (Table 1). The IgG4 expression vector pN5KG4 was obtained from IDEC Pharmaceuticals (U.S. Pat. No. 6,001,358.) The resulting vectors, pKLG1/F32K3H and pKLG4/F32K3H, were confirmed by restriction enzyme digest and sequencing.

Nucleotide sequence of cDNA of 112F32 HV (from initiation codon (ATG) to the end of variable region) SEQ ID NO:3

```
ATGGAGTGGG GGCCGTGCTG GGTTTTCCTT GTTGTTATTT TAGAAGGTGT CCAGTGTGGG    60

GTGCAGCTGG TGGAGTCTGG GGGAGGCTTG GTACAGCCTG GGGGGTCCCT GAGACTCTCC   120

TGTGCAGCCT CTGGATTCAC CTTCAGTAGC TATAGCATGA ACTGGGTCCG CCAGGCTCCA   180

GGGAAGGGGC TGGAGTGGGT TCATACATT AGTAGTAGTA GTAGTACCAT AIACTATGCA   240

GACTCTGTGA AGGGCCGATT CACCATCTCC AGAGACAATG CCAAGAACTC ACTGTATCTG   300

CAAATGAACA GCCTGAGAGA CGAGGACACG GCTGTGTATT ACTGTGCGAG AGGAGTGTAT   360

CACAATGGCT GGTCCTTCTT TGACTACTGG GGCCAGGGAA CCCTACTCAC CGTCTCCTCA   420
```

Nucleotide sequence of cDNA of 112F32 LV (from initiation codon (ATG) to the end of variable region) SEQ ID NO:4

```
ATGGACATGA GGGTCCTCGC TCAGCTCCTG GGGCTCCTGC TGCTCTGTTT CCCAGGTGCC   60
AGATGTGACA TCCAGATGAC CCAGTCCCCA TCCTCACTGT CTGCATCTGT AGGAAACAGA  120
GTCACCATTA CTTGTCGGGC GAGTCAGGAT ATTAGCAGCT GGTTAGCCTG GTATCAGCAG  180
AAACCAGAGA AAGCCCCTAA GTCCCTGATC TATGCTGCAT CCAGTTTGCA AAGTGGGGTC  240
CCATCAAGGT TCAGCGGCAG TGGATCTGGG ACAGATTTCA CTCTCACCAT CAGCAGCCTG  300
CAGCCTGAAG ATTTTGCAAC TTATTACTGC AACAGTATA  ATAGTTACCC CCTCACCTTC  360
GGCCAAGGGA CACGACTGGA GATTAAACGA                                   390
```

Nucleotide sequence of cDNA of 112V8 HV (from initiation codon (ATG) to the end of variable region) SEQ ID NO:5

```
ATGGACACAC TTTGCTCCAC GCTCCTGCTG CTGACCATCC CTTCATGGGT CTTGTCCCAG   60
ATCACCTTGA AGGAGTCTGG TCCTACGCTA GTGAAGCCCA AACAGACCCT CACGCTGACC  120
TGCACCTTCT CTGGATTCTC ACTCAGCACT AGTGGAATGG GTGTGGGCTG GATCCGTCAG  180
CCCCCAGGAA AGGCCCTGGA GTGGCTTGCA GTCATTTATT GGGATGATCA TCAACTCTAC  240
AGTCCATCTC TGAAGAGCAG GCTCACCATC ACCAAGGACA CCTCCAAAAA CCAGGTGGTC  300
CTTACAATGA CCAACATGGA CCCTGTGGAC ACAGCCACAT ATTACTGTGC ACACAGACGA  360
GGGGCCTTCC AGCACTGGGG CCAGGGCACC CTGGTCACCG TCTCCTCAGC TTCCACCAA   419
GGGC                                                               423
```

Nucleotide sequence of cDNA of 112V8 LV (from initiation codon (ATG) to the end of the variable region) SEQ ID NO:6

```
ATGGAAACCC CAGCGCAGCT TCTCTTCCTC CTGCTACTCT GGCTCCCAGA TACCACCGGA   60
GAAATTGTGT TGACGCAGTC TCCAGGCACC CTGTCTTTGT CTCCAGGGGA AAGAGCCACC  120
CTCTCCTGCA GGGCCAGTCA GAGTGTTAGC AGCAGCTACT TAGCCTGGTA CCAGCAGAAA  180
CCTGGCCAGG CTCCCAGGCT CCTCATCTAT GGTGCATCCA GCAGGGCCAC TGGCATCCCA  240
GACAGGTTCA GTGGCAGTGG GTCTGGGACA GACTTCACTC TCACCATCAG CAGACTGGAG  300
CCTGAAGATT TTGCAGTGTA TTACTGTCAG CACTATGATA GCTCGCTCAC TTTCGGCGGA  360
GGGACCAAGG TGGAGATCAA ACGAACT                                      387
```

Amino acid sequence of cDNA of 112F32 HV (leader sequence (bold) and variable region) SEQ ID NO:7

```
MEWGPCWVFL VVILEGVQCG VQLVESGGGL VQPGGSLRLS CAASGFTFSS YSMNWVRQAP   60
GKGLEWVSYI SSSSSTIYYA DSVKGRFTIS RDNAKNSLYL QMNSLRDEDT AVYYCARGVY  120
HNGWSFFDYW GQGTLLTVSS                                              140
```

Amino acid sequence of cDNA of 112F32 kappa LV
(leader sequence (bold) and variable region) SEQ ID NO:8

MDMRVLAQLL GLLLLCFPGA RCDIQMTQSP SSLSASVGNR VTITCRASQD ISSWLAWYQQ  60

KPEKAPKSLI YAASSLQSGV PSRFSGSGSG TDFTLTISSL QPEDFATYYC QQYNSYPLTF 120

GQGTRLEIKR 130

Amino acid sequence of cDNA of 112V8 HV (leader
sequence (bold) and variable region) SEQ ID NO:9

MDTLCSTLLL LTIPSWVLSQ ITLKESGPTL VKPKQTLTLT CTFSGFSLST SGMGVGWIRQ  60

PPGKALEWLA VIYWDDHQLY SPSLKSRLTI TKDTSKNQVV LIMTNMDPVD TATYYCAHRR 120

GAFQHWGQGT LVTVSSASTK G 141

Amino acid sequence of cDNA of 112V8 LV (leader
sequence (bold) and variable region) SEQ ID NO:10

METPAQLLFL LLLWLPDTTG EIVLTQSPGT LSLSPGERAT LSCRASQSVS SSYLAWYQQK  60

PGQAPRLLIY GASSRATGIP DRFSGSGSGT DFTLTISRLE PEDFAVYYCQ QYDSSLTFGG 120

GTKVEIKRT 129

TABLE 1

Synthesized DNA primers (SEQ ID NOS: 11-37)

| No | Name | Sequence 5' to 3' | Length |
|---|---|---|---|
| 11 | RACEUPS5' | CTAATACGACTCACTATAGGGC | 22-mer |
| 12 | IgG1p | TCTTGTCCACCTTGGTGTTGCTGGGCTTGTG | 31-mer |
| 13 | HK5 | AGGCACACAACAGAGGCAGTTCCAGATTTC | 30-mer |
| 14 | M13F | GTAAAACGACGGCCAGTG | 18-mer |
| 15 | M13R | CAGGAAACAGCTATGAC | 17-mer |
| 16 | V8H38 | GAGAGAGAGAGCTAGCTGAGGAGACGGTGACCAGGGT | 37-mer |
| 17 | V8H39 | AGAGAGAGAGGTCGACCACCATGGACACACTTTGCTCCACG | 41-mer |
| 18 | V8L42 | AGAGAGAGAGATCTCTCACCATGGAAACCCCAGCGCAGCTTC | 42-mer |
| 19 | V8L43 | AGAGAGAGAGCGTACGTTTGATCTCCACCTTGGTCCCTCC | 40-mer |
| 20 | HH-2 | GCTGGAGGGCACGGTCACCACGCTG | 25-mer |
| 21 | HK-2 | GTTGAAGCTCTTTGTGACGGGCGAGC | 26-mer |
| 22 | F725' | ACCGTGTCGACTGGATTCCAAGGCATTTCCAC | 32-mer |
| 23 | M2H3' | GGTGCTAGCTGAGGAGACGGTGAC | 24-mer |
| 24 | F32K5' | AATCAAGATCTGTCAGGACACA | 22-mer |
| 25 | K52D3' | TATCCCGTACGTTTAATCTCCAGTCGTGTC | 30-mer |
| 26 | Y131HF | AGAGAGAGAGGTCGACCACCATGGACACACTTTGCTCCACG | 41-mer |
| 27 | Y131HR | AGAGAGAGA GGCTAGCTG AAGAGA CGGTGA CCATTGT | 37-mer |
| 28 | Y131LF5 | AGAGAGAGA GGTCGACCACCATGG AAACCCCAG CGCAGCTT | 41-mer |
| 29 | Y131LR | AGAGAGAGA GCGTACGTTTGA TTT CCA CCTTGGTCCCTTG | 40-mer |
| 30 | Y55HF | AGAGAGAGAGGTCGACCACCATGGACACACTTTGCTCCACG | 41-mer |
| 31 | Y55HR | AGAGAGAGAGGCTAGCTGAAGAGACGGTGACCATTGT | 37-mer |

TABLE 1-continued

Synthesized DNA primers (SEQ ID NOS: 11-37)

| No | Name | Sequence 5' to 3' | Length |
|----|------|-------------------|--------|
| 32 | Y55LF | AGAGAGAGAGATCTCTCACCATGGAAACCCCAGCGCAGCTTC | 42-mer |
| 33 | Y55LR | AGAGAGAGAGCGTACGTTTGATTTCCACCTTGGTCCCCTG | 40-mer |
| 34 | Z5HF | AGA GAGAGAGGTCGACCACCATGACCATGATTACGCCAAGC | 41-mer |
| 35 | Z5HR | GAGAGAGAGAGCTAGCTGAGGAGACGGTGACCAGGGT | 37-mer |
| 36 | Z5LF | AGAGAGAGAGATCTCTCACCATGGAAGCCCCAGCTCAGCTTC | 42-mer |
| 37 | Z5LR | AGAGAGAGAGCGTACGTTTAATCTCCAGTCGTGTCCCTTG | 40-mer |

Nucleotide sequence of cDNA of 112Y55 HV (from initiation codon (ATG) to the end of the variable region) SEQ ID NO:38

```
ATGGACACAC TTTGCTCCAC GCTCCTGCTG CTGACCATCC CTTCATGGGT CTTGTCCCAG   60
ATCACCTTGA AGGAGTCTGG TCCTACGCTG GTGAAACCCA CACAGACCCT CACGCTGTCC  120
TGCACCTTCT CTGGGTTCTC ACTCAGCACT AGTGGAGTGG GTGTGGGCTG GATCCGTCAG  180
CCCCCAGGAA AGGCCCTGGA ATGGCTTGCA CTCATTCATT GGGATGATGC TGAGCGCTAC  240
AGTCCATCTC TGAAGAGCAG GCTCACCATC ACCAAGGACA CCTCCAAAAA CCAGGTGGTC  300
CTTACAATGA CCAACATGGA CCTTGTGGAC ACAGCCACAT ATTACTGTGC ACACACCCGG  360
GGGGCTTTTG ATATCTGGGG CCAAGGGACA ATGGTCACCG TCTCTTCA              408
```

Nucleotide sequence of cDNA of 112Y55 LV (from initiation codon (ATG) to the end of the variable region) SEQ ID NO:39

```
ATGGAAACCC CAGCGCAGCT TCTCTTCCTC CTGCTACTCT GGCTCCCAGA TACCACCGGA   60
GAAATTGTGT TGACGCAGTC TCCAGGCACC CTGTCTTTGT CTCCAGGGGA AAGAGCCATC  120
CTCTCCTGCA GGGCCAGTCA GAGTGTTAGC AGCAGCTTCT TAGCCTGGTA CCAACAGAAA  180
CCTGGCCAGG CTCCCAGGCT CCTCATCTAT GGTGCATTTA GCAGGGCCAC TGGCATCCCA  240
GACAGGTTCA GTGGCAGTGG GTCTGGGACA GACTTCACTC TCACCATCAG CAGACTGGAG  300
CCTGAAGATT TTGCAGTGTA TTACTGTCAG CAGTATGATA GCTCACGGAC GTTCGGCCAG  360
GGGACCAAGG TGGAAATCAA A                                           381
```

Nucleotide sequence of cDNA of 112Y131 HV (from initiation codon (ATG) to the end of the variable region) SEQ ID NO:40

```
ATGGACACAC TTTGCTCCAC GCTCCTGCTG CTGACCATCC CTTCATGGGT CTTGTCCCAG   60
ATCACCTTGA AGGAGTCTGG TCCTACGCTG GTGAAACCCA CACAGACCCT CACGCTGACC  120
TGCACCTTCT CTGGATTCTC ACTCAGCACT AGTGGAGTGG GTGTGGGCTG GATCCGTCAG  180
CCCCCAGGAA AGGCCCTGGA GTGGCTTGCA CTCATTTATT GGGATGATCA TAGCCCCTAC  240
AGCCCATCTC TGAAGAGCAG GCTCACCATC ACCAAGGACA CCTCCAAAAA CCAGGTGGTC  300
CTTACAATGA CCAACATGGA CCCTGTGGAC ACAGCCACAT ATTACTGTGC ACGCACCCGG  360
GGGGCTTTTG ATATCTGGGG CCAAGGGACA ATGGTCACCG TCTCTTCA              408
```

Nucleotide sequence of cDNA of 112Y131 LV (from initiation codon (ATG) to the end of the variable region) SEQ ID NO:41

```
ATGGAAGCCC CAGCGCAGCT TCTCTTCCTC CTGCTACTCT GGCTCCCAGA TACCACCGGA   60
GAAATTGTGT TGACACAGTC TCCAGCCACC CTGTCTTTGT CTCCAGGGGA AAGAGCCACC  120
CTCTCCTGCA GGGCCAGTCA GGGTGTTAGC AGCTACTTAG CCTGGTACCA GCAGAAACCT  180
GGCCAGGCTC CCAGGCTCCT CATCTATGAT GCATCCAACA GGGCCACTGG CATCCCAGCC  240
AGGTTCAGTG GCAGTGGGCC TGGGACAGAC TTCACTCTCA CCATCAGCAG CCTAGAGCCT  300
GAAGATTTTG CAGTTTATTA CTGTCAGCAG CGTAGCAACT GGCATCCGAC GTTCGGCCAA  360
GGGACCAAGG TGGAAATCAA ACGAACTGTG GCTGCACCAT C                      381
```

Nucleotide sequence of cDNA of 112Z5 LV (from initiation codon (ATG) to the end of the variable region) SEQ ID NO:42

```
ATGACCATGA TTACGCCAAG CTTGGTACCG AGCTCGGATC CACTAGTAAC GGCCGCCAGT   60
GTGCTGGAAT TCGCCCTTCT AATACGACTC ACTATAGGGC AAGCAGTGGT ATCAACGCAG  120
AGTACGGGGG GAGGCTTGGT ACAGCCTGGC AGGTCCCTGA GACTCTCCTG TGCAGCCTCT  180
GGATTCACCC TTGATGATTA TGGCATGCAC TGGGTCCGGC AAGCTCCAGG GAAGGGCCTG  240
GAGTGGGTCT CAGGTATTAG TTGGAATAGT GATAGTATAG GCTATGTGGA CTCTGTGAAG  300
GGCCGATTCA CCATCTCCAG AGACAACGCC AAGAACTCCC TGTATCTGCA AATGAACAGT  360
CTGAGAGTTG AGGACACGGC CTTGTATTAC TGTGTAAAAG ATATTAGTGG CTGGTACAGC  420
TTTGACTACT GGGGCCAGGG AACCCTGGTC ACCGTCTCCT CA                     462
```

Nucleotide sequence of cDNA of 112Z5 LV (from initiation codon (ATG) to the end of the variable region) SEQ ID NO:43

```
ATGGAAGCCC CAGCTCAGCT TCTCTTCCTC CTGCTACTCT GGCTCCCAGA TACCACCGGA   60
GAAATTGTGT TGACACAGTC TCCAGCCACC CTGTCTTTGT CTCCAGGGGA AAGAGCCACC  120
CTCTCCTGCA GGGCCAGTCA GAGTGTTAGC AGCTACTTAG CCTGGTACCA ACAGAAACCT  180
GGCCAGGCTC CCAGGCTCCT CATCTATGAT GCATCCAACA GGGCCACTGG CATCCCAGCC  240
AGGTTCAGTG GCAGTGGGTC TGGGACAGAC TTCACTCTCA CCATCAGCAG CCTAGAGCCT  300
GAAGATTTTG CAGTTTATTA CTGTCAGCAG CGTAGCAACT GGCCGATCAC CTTCGGCCAA  360
GGGACACGAC TGGAGATTAA A                                            381
```

Amino acid sequence of cDNA of 112Y55 HV (leader sequence (bold) and variable region) SEQ ID NO:44

```
MDTLCSTLLL LTIPSWVLSQ ITLKESGPTL VKPTQTLTLS CTFSGFSLST SGVGVGWIRQ   60
PPGKALEWLA LIHWDDAERY SPSLKSRLTI TKDTSKNQVV LTMTNMDLVD TATYYCAHTR  120
GAFDIWGQGT MVTVSS                                                   136
```

Amino acid sequence of cDNA of 112Y55 LV (leader sequence (bold) and variable region) SEQ ID NO:45

METPAQLLFL LLLWLPDTTG EIVLTQSPGT LSLSPGERAI LSCRASQSVS SSFLAWYQQK 60

PGQAPRLLIY GAFSRATGIP DRFSGSGSGT DFTLTISRLE PEDFAVYYCQ QYDSSRTFGQ 120

GTKVEIK 127

Amino acid sequence of cDNA of 112Y131 HV (leader sequence (bold) and variable region) SEQ ID NO:46

MDTLCSTLLL LTIPSWVLSQ ITLKESGPTL VKPTQTLTLT CTFSGFSLST SGVGVGWIRQ 60

PPGKALEWLA LIYWDDHSPY SPSLKSRLTI TKDTSKNQVV LTMTNMDPVD TATYYCARTR 120

GAFDIWGQGT MVTVSS 136

Amino acid sequence of cDNA of 112Y131 LV (leader sequence (bold) and variable region) SEQ ID NO:47

MEAPAQLLFL LLLWLPDTTG EIVLTQSPAT LSLSPGERAT LSCRASQGVS SYLAWYQQKP 60

GQAPRLLIYD ASNRATGIPA RFSGSGPGTD FTLTISSLEP EDFAVYYCQQ RSNWHPTFGQ 120

GTKVEIK 127

Amino acid sequence of cDNA of 112Z5 HV (leader sequence (bold) and variable region) SEQ ID NO:48

MTMITPSLVP SSDPLVTAAS VLEFALLIRL TIGQAVVSTQ STGGGLVQPG RSLRLSCAAS 60

GFTLDDYGMH WVRQAPGKGL EWVSGISWNS DSIGYVDSVK GRFTISRDNA KNSLYLQMNS 120

LRVEDTALYY CVKDISGWYS FDYWGQGTLV TVSS 154

Amino acid sequence of cDNA of 112Z5 LV (leader sequence (bold) and variable region) SEQ ID NO:49

MEAPAQLLFL LLLWLPDTTG EIVLTQSPAT LSLSPGERAT LSCRASQSVS SYLAWYQQKP 60

GQAPRLLIYD ASNRATGIPA RFSGSGSGTD FTLTISSLEP EDFAVYYCQQ RSNWPITFGQ 120

GTRLEIK 127

Production of recombinant human anti-OX40 antibody from CHO cells: For the production of recombinant antibody, the individual antibody vectors containing the anti-OX40 antibody were electroporated into host cell dhfr-defective strain of Chinese Hamster Ovary cell (CHO cells, ATCC #CRL-9096) and recombinant antibody was isolated from the supernatant of the transfected cells. Briefly, ten microgram of purified DNA expression vector was linearized by a DNA restriction enzyme, NruI, and the DNA was transfected into $3 \times 10^6$ cells of CHO cells using a Bio Rad electroporator (0.8 kV, 25 uF). The transfected cells were seeded in 96-well culture plates, in EX-CELL 325 PF CHO serum-free medium with glutamine (JRH Bioscience, Lenexa, Kans.), supplemented with penicillin/streptomycin (BioWhitaker), HT (Sigma), and Geneticin (Invitrogen Corp.) for selecting CHO cells containing the DNA vector. After the selection of several stable transfectant lines, high human IgG producers were identified by ELISA, and used for production of recombinant antibody.

Example 2

The example describes various characteristics of human monoclonal antibodies to human OX40.

KM Mice™ were immunized with soluble recombinant hOX40:hFc in CFA/IFA, hOX40:hFC+hOX40:hFc-ova conjugate in RIBI, heat denatured hOX40:hFc in RIBI, or irradiated, activated human T cells in RIBI. Several of the mice raised anti-human OX40 specific antibodies, with a range in human IgG OX40 specific titers. Splenocytes from the highest responders were fused with myeloma cells to generate human anti-human OX40 producing hybridomas. The production of anti-OX40 antibodies was determined by both ELISA and flow cytometry using recombinant soluble hOX40:hFc and CHO-OX40 transfectants, respectively. The positive hybridomas were cloned by limiting dilution to yield monoclonal hybridomas. (Table 2)

TABLE 2

Antigens Used for Antibody Generation

| Antibody | Antigen |
|---|---|
| 112F32 | hOX40:hFc |
| 112V8 | Activated human T cells |
| 112Y55 | hOX40:hFc plus hOX40:hFc-ovalbumin |
| 112Y131 | hOX40:hFc plus hOX40:hFc-ovalbumin |
| 112Z5 | Heat denatured hOX40:hFc |

Several antibodies were further characterized for relative binding affinity for human OX40, the ability to block human OX40 ligand binding in vitro, cross-blocking each other, blockade of proliferation in vitro, the ability to block inflammation in vivo, and the ability to mediate ADCC. (Table 3).

112F32, 112V8, 112Y131, 112Y55, and 112Z5 all bound specifically to activated human T cells, but not to resting human T cells (FIG. 1). Human T cells activated for three days were labeled with human anti-human OX40 antibodies at various concentrations and detected with anti-human IgG-PE. The binding of these human anti-human OX40 antibodies was saturable. The maximum binding of each antibody was determined by titrating the amount of antibody needed to label activated human T cells (FIG. 2). A range of relative binding affinities were obtained (KD and BMAX, Table 3). The binding of the purified mouse anti-human OX40 antibody L106 was also determined and 112F32, 112V8, 112Y55, 112Y131, and 112Z5 all had higher BMAX than L106 on activated T cells.

Three "epitope" groups have been identified for these human anti-human OX40 antibodies. 112V8, 112Y55, and 112Y131 all crossblock one another while 112F32 and 112Z5 each have unique binding sites. 112V8, 112Y131, and 112Y55 partially reduce binding of 112Z5, but the reverse is not the case, 112Z5 only blocks itself. This suggests that 112Z5 recognizes a different epitope than 112V8, 112Y55, and 112Y131 and any reduction in binding may be due to steric hinderance. These human anti-OX40 antibodies do not block L106, 315 or ACT35 binding to OX40 (FIGS. 3A and 3B), while L106 blocks itself and ACT35, it only reduced binding of 112V8 and 112Y131 by 10% compared with control antibodies (solid line) that do not bind OX40. This indicates that the antibodies described here recognize a different epitope than L106. Clone 315 did reduce binding of 112V8 and 112Y131, however since these latter antibodies did not block 315 binding, they must bind different epitopes.

A flow cytometric assay was also used to evaluate the ability of the antibodies to block binding to surface expressed OX40 on activated human T cells. Activated T cells were stained with the blocking antibodies followed by addition of biotinylated anti-OX40 antibodies. Additionally, activated human T cells were labeled with mouse anti-human OX40 antibodies to block OX40 binding. Binding of the biotinylated anti-OX40 antibodies to these cells were detected with SA-PE. The cells were analyzed by flow cytometry. The geometric mean of the positive SA-PE staining was used to calculate percent inhibition using the same formula, i.e., (100–(OD sample/OD maximum binding sample))*100. These data (FIGS. 4A and 4B) correlate with the ELISA analysis.

TABLE 3

Characteristics of Human Anti-Human OX40 Monoclonal Antibodies

| Antibody | Original Subclass | Epitope | Labeling of Activated T cells KD μM | Labeling of Activated T cells BMAX Geo Mean | OX40L Blocking by ELISA IC50 (μg/ml) | OX40L Blocking by FACS on T cells IC50 (μg/ml) | In vitro Efficacy | In Vivo Efficacy | ADCC % Lysis at 10 μg/ml@ |
|---|---|---|---|---|---|---|---|---|---|
| 112F32 | IgG4 | A | 0.013 | 103.5 | 0.650 | ni* | +^ | IgG1+ IgG4+ | IgG1 37% IgG4 NT |
| 112V8 | IgG4 | B | 0.036 | 180.8 | 0.051 | 0.62 | + | IgG1+ IgG4+ | IgG1 55.6% IgG4 18% |
| 112Y55 | IgG1 | B | 0.014 | 161.8 | 0.073 | 0.90 | + | + | 54.2% |
| 112Y131 | IgG4 | B | 0.025 | 170.7 | 0.069 | 0.91 | + | + | 18% |
| 112Z5 | IgG1 | C | 0.011 | 118.2 | 0.081 | 14.65 | + | + | 35% |
| L106 | Mouse IgG1 | L | 0.001 | 52.0 | 0.982 | 60.91 | NT | NT | NT |

*ni; not inhibitory at 50 μg/ml
^+: inhibited proliferation in vitro or disease in vivo, not quantitative
NT; not tested
@Percent lysis with irrelevant antibody at 10 μg/ml was 14%

The OX40 antibodies were analyzed by ELISA to determine if the compete with one another for binding to soluble OX40. The individual human antibodies were coated in the wells of a 96 well plate. hOX40:mFc was pre-incubated with soluble anti-OX40 antibodies (blocking antibodies) and then added to the coated wells. Binding of hOX40:mFc to the coated antibody was detected with anti-mouse IgG-HRP. Percent inhibition was determined using the following formula (100–(OD sample/OD maximum binding sample))*100 (FIG. 3A).

Additionally, mouse antibodies were coated in the wells of a 96 well plate (L106, 315, ACT35 or mouse IgG) and hOX40:hFc was pre-incubated with the blocking antibodies. Binding of the hOX40:hFc was detected with sheep anti-human IgG-HRP (FIG. 3B).

Three epitopes are recognized by the human anti-human OX40 antibodies, one by 112F32, a second by 112Z5, and a third by 112V8 and 112Y131. As was the case with the ELISA data, 112Z5 only blocked itself, but its binding was reduced by 112V8 and 112Y131. The same is true for L106 blockade of 112V8 and 112Y131. If L106 is bound to the cells first, 112V8 and 112Y131 are still able to bind efficiently to human OX40. However, 112V8 and 112Y131 inhibited L106 binding. These data taken together suggest that the antibodies sterically hinder L106 from binding, but do not recognize the same epitope. 112F32 and 112Z5 do not block L106 binding. ACT35 did not inhibit binding of 112F32, 112V8, 112Y131, or 112Z5, but clone 315 did reduce binding of 112V8 and 112Y131 by 50%. The binding and detection of antibodies to live cells may induce internalization of the surface molecule so the level of binding of an individual antibody may be reduced due to overall lower surface expression of OX40 and not to blocking the binding of the antibodies. Higher affinity antibodies may cause more internalization than lower affinity antibodies. This may explain the differences between the ELISA and flow cytometric data as well as the differences in results depending on which antibody is used for blocking.

The ability of 112F32, 112V8, 112Y131, 112Y55, and 112Z5 to block soluble hOX40L binding to coated hOX40:hFc fusion protein was tested using an ELISA protocol (FIG. 5A, Table 3). The plates were coated with hOX40:hFc and after blocking non-specific sites the anti-OX40 antibodies were allowed to bind. Without washing OX40L-FLAG was added to the wells. Bound ligand was detected with anti-FLAG-HRP secondary antibody. Percent inhibition was determined using the following formula (100−(OD sample/OD maximum OX40L binding))*100. 112V8, 112Y55, and 112Y131 prevented 85% of the binding of soluble OX40L to hOX40:hFc. 112F32 prevented approximately 70% of the binding of soluble hOX40L to hOX40:hFc and 112Z5 blocked 67% of the maximal binding. These data suggest that these human anti-human OX40 antibodies bind to the portion of OX40 that is involved in ligand binding.

Slightly different results were obtained when a flow cytometric based assay was used to monitor blockade of soluble OX40L binding to activated human T cells that express OX40 (FIG. 5B). Activated human T cells were labeled with anti-OX40 antibodies followed by soluble flag tagged-human OX40L. Binding of OX40L was detected with anti-FLAG-PE antibody. Percent inhibition was determined using the same formula, i.e., (100−(sample/maximum binding))*100. In this study, 112F32 was unable to prevent OX40L binding and blockade by 112Z5 was reduced, while the other antibodies, 112V8, 112Y55, and 112Y131 continued to have similar blocking abilities. The difference in the results may be dependent on the affinity of 112F32 and 112Z5 for OX40. It may also be due to trimerization of the OX40 protein on the cell surface as opposed to dimerization of the soluble OX40:mFc fusion protein.

Alternatively, OX40 expressed on the surface of activated T cells may be in a complex with 4-1BB (Ma, et al., *Blood* 106(6): 2002-10 (2005)) or an inhibitory molecule similar to BTLA (Cheung, et al., *Proc Natl Acad Sci USA* 102(37): 13218-23 (2005); Compaan, et al., *J Biol Chem* 280(47): 39533-6 (2005); Croft, *Trends Immunol* 26(6): 292-4 (2005); Gonzalez, et al., *Proc Natl Acad Sci USA* 102(4): 1116-21 (2005); Sedy, et al., *Nat Immunol* 6(1): 90-8 (2005)) that prevents 112F32, or reduces 112Z5 binding but does not block OX40L binding to OX40. The last three possibilities may point to the specific epitope bound by the individual antibodies. The epitope recognized by L106, a mouse anti-human OX40 antibody, is also dependent on the confirmation of OX40 ligand and OX40, as L106 blocked 95% of OX40L binding to the recombinant OX40 protein, but only 60% of binding to activated T cells. These data indicate that there are multiple epitopes on OX40, some of which completely interfere with OX40L binding, while others only partially block the interaction. Binding of these antibodies to the different epitopes may or may not have unique functional consequences.

Figure 6:
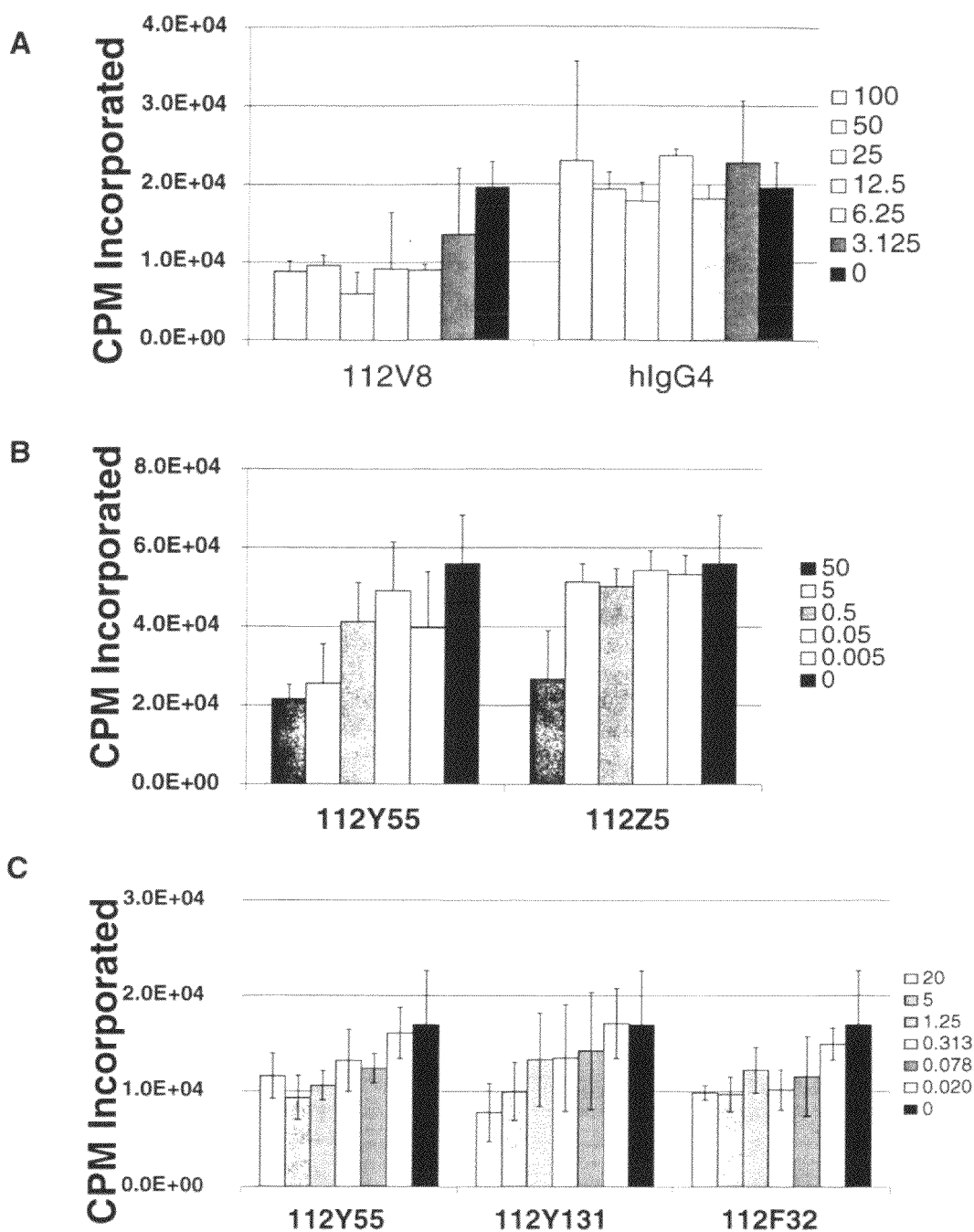

Blockade of ligand binding by either method does not necessarily dictate that OX40 signaling will be impaired by a given antibody. To determine if the human anti-human OX40 antibodies can prevent signaling via OX40, two way mixed lymphocyte cultures were set up using total PBMC from allogeneic donors. Peripheral blood mononuclear cells from allogeneic donors were co-cultured in 96 well U bottom plates for seven days in the presence or absence of various doses of anti-OX40 antibodies or control antibody in triplicate. $1 \times 10^5$ cells/donor were added per well. The plates were pulsed for the last eighteen hours of culture with 1 μCi/well $^3$HTdR. The cells were harvested and counted on a scintillation counter. Proliferation was measured in the presence or absence of control or anti-OX40 antibodies (FIG. 6). 112V8 (FIG. 6A), 112Y55 and 112Z5 (FIG. 6B), and 112Y55, 112Y131, and 112F32 (FIG. 6C) were all able to reduce the amount of proliferation induced by allogeneic cells in a dose dependent manner whereas an negative control hIgG4, anti-human serum albumin, had no effect on proliferation (FIG. 6A). Multiple studies were performed and the magnitude of the responses, maximum CPM incorporated, was dependent on the combination of donor PBMC used for each assay. In mixed lymphocyte cultures both CD4 and CD8 T cells respond to the allogeneic antigens. Reduction in the proliferative response by the human anti-human OX40 antibodies may be due to direct inhibition of both CD4 and CD8 T cells.

Example 3

This example describes mapping epitopes of human anti-human OX40 antibodies with linear peptides of human OX40.

Three peptides within the extracellular domain of human OX40 (Table 4) were chosen to begin mapping of the epitope(s) recognized by 112F32, 112V8, 112Y55, 112Y131, and 112Z5.

TABLE 4

Human OX40 Peptides

| Peptide Name | Peptide Seq | Antibody | | | | |
|---|---|---|---|---|---|---|
| | | 112F32 | 112V8 | 112Y55 | 112Y131 | 112Z5 |
| 112A | RPAGPGFYNDVVSSKPC SEQ ID NO: 52 | − | − | − | − | − |
| 112B | RAGTQPLDSYKPGVDC SEQ ID NO: 53 | − | − | − | − | − |
| 112C | LAGKHTLQPASNSSDAIC SEQ ID NO: 54 | − | − | − | − | − |

The peptides were generated by A & A Lab, LLC and conjugated to keyhole limpet hemocyanin ("KLH") with a maleimide linker following the manufacturer's instructions (Pierce). The peptides were coated at 10 μg/ml in carbonate buffer to 96 well Maxisorp ELISA plates (Nunc) at 4° C. overnight. The plate was washed with PBS/0.1% Tween 20 and then blocked with Casein buffer (Pierce) for three hours at room temperature. Candidate antibodies were added at 10 µg/ml diluted in 10% Casein in PBS/0.1% Tween 20. The remainder of the ELISA was performed as described for the OX40 specific antibody detection ELISA.

None of the human anti-human OX40 antibodies detectably reacted with these human OX40 peptides, whereas serum from mice immunized with the peptides bound the appropriate peptide. These results indicate that 112F32, 112V8, 112Y55, 112Y131, and 112Z5 do not detectably bind to these short linear epitopes from the human OX40 extracellular sequence under the assay conditions used. These data do not preclude these sequences from being recognized by the human anti-human OX40 antibodies if they were included in longer peptide sequences.

Example 4

This example describes in vivo functional analysis of human anti-human OX40 monoclonal antibodies.

An acute xenogenic graft versus host disease (XGVHD) model was used to test the therapeutic potential of the 112V8G1 human anti-human OX40 antibody in vivo (Watanabe, et al., *Clin Immunol* 120:247-259 (2006)). In this model human peripheral blood mononuclear cells are transferred into severe combined immunodeficient (SCID) mice. Prior to transfer the mice are treated with an anti-IL2Rβ chain antibody to deplete endogenous murine natural killer cells, and then they are sub-lethally irradiated to allow migration of the human cells to the intestinal tract. The human T cells expand and induce a graft versus host like disease, resulting in weight loss, hematuria, hydroperitoneum, inflammatory cell infiltrates in the liver and intestinal tract, and eventually death. The disease is primarily mediated by human T cells as transfer of purified T cells induces similar symptoms.

SCID mice were treated as described above plus either 112V8G1 or human IgG1 isotype control (anti-DNP) recombinant antibodies were administered at day 0 to test the prophylactic potential of OX40 blockade. The mice received 100, 20, or 2 pig of 112V8G1 antibody or 100 pig anti-DNP by intravenous injection at day 0. Body weight was determined every three to four days. At day twelve, the mice were killed and analyzed for symptoms of disease and the spleens were collected for flow cytometric analysis. The gross pathology observed at day twelve was scored as follows, diarrhea (0-1), hemorrhaging in the intestine and peritoneal cavity, and peritonitis (each 0-5), with the higher number indicating more severe disease. The sum of all disease symptoms was used to determine the total gross pathology score. The mice that received the control antibody all displayed symptoms of XGVHD, with higher pathology scores than mice that received 112V8G1. All doses of 112V8G1 tested reduced or prevented these symptoms (FIG. 7A.)

Analyses of the spleens were in agreement with this observation. Single cell suspensions of the spleens were analyzed by flow cytometry for the presence of human T cells. Human T cells were present in the spleens of mice treated with the control antibodies, but the number of human T cells in 112V8G1 treated animals were significantly lower than the number of T cells in the control animals (FIG. 7B.) Furthermore, inflammatory human cytokines (interferon-gamma, tumor necrosis factor, and granulocyte-macrophage colony stimulating factor) in the serum were measured using multiplex technology. Inflammatory human cytokines were reduced in 112V8G1 treated animals compared with controls. The most dramatic affect was on the levels of interferon gamma (FIG. 7C.) Appearance of OX40+ T cells in the peripheral blood of allogeneic bone marrow transplant patients has been correlated with the onset of chronic GVHD (Gadisseur, et al., *Bone Marrow Transplant* 23(10): 1013-7 (1999); Kotani, et al., *Blood* 98(10): 3162-4 (2001); Sanchez, et al., *Br J Haematol* 126(5): 697-703 (2004)).

In order to evaluate the efficacy of OX40 blockade in the treatment of chronic GVHD, an animal model system of chronic xenogenic GVHD was established. The model is similar to the acute xenogenic GVHD model except that one million purified CD4+ cells are injected into SCID mice instead of total PBMC. The dose of irradiation is also reduced to 2.12Gy to reduce the level of intestinal damage. The first evidence of disease is hair loss and weight loss, followed by death, which is partially due to infiltration of T cells into the lungs. Disease symptoms become apparent around day thirty. Groups of five mice each were treated with 112V8G1 recombinant antibody at 100, 20, or 2 µg weekly for five weeks or with anti-DNP hIgG1 control antibody at 100 µg weekly for five weeks. Surviving mice were analyzed at week seven. Gross pathology scores were determined by the extent of hair loss, hemorrhaging, and peritonitis (each 0-5) and diarrhea (0-1).

The primary pathology observed was hair loss, and all three doses of 112V801 reduced this disease symptom compared with control treated mice (FIG. 8A). This observation agreed with the reduction of human T cells in the spleens of 112V8G1 treated mice at day 48 post transfer of CD4 T cells (FIG. 8B). In this model the human T cells migrate to the lymph nodes which are easily detected in control animals, but significantly reduced or not found in anti-OX40 treated animals (FIG. 8C). Note, no lymph nodes were found in the animals treated with 112V8G1 at 20 or 100 µg.

Furthermore, unlike the acute model, OX40 positive cells can be easily detected in the spleens and lymph nodes of control treated mice and the number of OX40+ cells was reduced in 112V8G1 treated animals (FIGS. 8B and 8C). Inflammatory cytokines were detected in the serum of mice that received human CD4 T cells and the amount of cytokines detected were reduced in mice treated with 112V8G1 anti-human OX40 compared with control human IgG1. The cytokines produced in this disease model include but are not limited to interleukin 2, interleukin, 4, interleukin 6, interleukin 8, interleukin 10, granulocyte-macrophage colony stimulating factor, interferon gamma and tumor necrosis factor alpha. All cytokines except for interleukin 6 were significantly reduced by treatment with 112V8G1, demonstrating the anti-inflammatory activity of OX40 signaling inhibition by depletion and/or blockade.

112V8G4PE was studied in the acute XGVHD model using a prophylactic regimen. This antibody does not have depleting activity, due to its inability to fix complement or bind Fe receptors and therefore prevention of disease would be dependent on blockade of OX40 signaling or down-modulation of OX40. A single injection of 112V8G4PE at 200, 20, or 2 µg at day 0 was given to five mice per group. Control treated mice received 200 µg of anti-DNP human IgG4 antibody at day 0, 3, or 6. Mice were analyzed at day twelve for gross pathology and the number of human T cells in the spleen (FIGS. 9A and 9B, Table 5). The gross pathology at day twelve was scored on a scale of 0-3 for diarrhea, peritoneal hemorrhaging or ascites, and intestinal hemorrhaging, with 0 being no pathology observed and 3 representing severe disease. Both 200 and 20 µg of 112V8G4PE prevented development of overt pathology, while a dose of 2 µg was not sufficient to prevent disease. The amount of gross pathology correlated with the number of human T cells in the spleen at day twelve. Compared with control treated animals, 200 or 20

μg of 112V8G4PE significantly reduced accumulation of human T cells in the spleen while a dose of 2 μg was ineffective. The differences observed in the titrations of 112V8G4PE (FIGS. 9A and 9B) and 112V8G1 (FIG. 7) may be attributed to the lack of depleting activity of the 112V8G4PE antibody.

112V8G4PE administration was delayed until day three or six to test the therapeutic efficacy of blockade of OX40 signaling. Mice were treated with 200 μg of 112V8G4PE or control human IgG4 antibody at either day three or day six following transfer of human PBMC. Gross pathology was assessed at day fourteen. Blockade of OX40 signaling ameliorated disease when 112V8G4PE anti-human OX40 antibody was given at either day three or day six compared with the level of disease observed in control antibody treated animals (FIG. 9C). The number of human T cells in the spleens of anti-OX40 treated mice was also significantly reduced compared with control treated mice. 112V8G1 also reduced disease if administered at day six. These data demonstrate the efficacy of OX40 blockade by OX40 specific antibodies as a therapeutic approach to reduce disease pathology.

In both the acute and chronic xenogenic models of graft versus host disease 112V8, a human anti-human OX40 antibody, significantly reduced disease pathology, production of inflammatory cytokines, and the number of human T cells in the spleens and lymph nodes compared with control treated animals. These data demonstrate that directly targeting OX40 positive cells is a suitable therapy for the prevention (prophylactic) and amelioration (therapeutic) of T cell-mediated diseases. Similar results were obtained in one or both models with 112F32, 112Y55, 112Y131, and 112Z5 (Table 3).

In the model of acute GVHD, both CD4 and CD8 human T cells are required for disease. The CD4 T cells are necessary for induction, while the CD8 T cells mediate the majority of the pathogenesis. Prevention and amelioration of disease by administration of one of the described human anti-human OX40 antibodies could be due to direct antagonism of both CD4 and CD8 T cells, or may be due to direct blockade of CD4 T cells with indirect affect on CD8 T cells by reducing CD4 help. In addition, OX40 antibodies may promote generation or increase numbers of regulatory T cells. Although not wishing to be bound by any theory, it is possible that one or all of these mechanisms may mediate amelioration of disease.

Although not wishing to be bound to any theory, a potential mechanism of action of these anti-human OX40 antibodies is to induce antibody dependent cell cytotoxicity (ADCC) by natural killer cell or neutrophil effector cells. This process is dependent on the ability of the Fc receptors expressed by the effector cells to bind to the anti-OX40 antibodies bound to OX40 expressed on activated T cells. The ability of immunoglobulins to bind Fc receptors is determined by the subclass of the antibody and by the type of Fc receptor. Human IgG1 antibodies bind to Fc receptors on natural killer cells and neutrophils while human IgG4 antibodies do not (Huber, et al., *Nature* 229(5284): 419-20 (1971); Brunhouse, et al., *Mol Immunol* 16(11): 907-17 (1979)). The human anti-human OX40 antibodies 112F32 (IgG1), 112V8 (IgG1 and IgG4PE), 112Y55 (IgG1), 112Y131 (IgG4), and 112Z5 (IgG1), were tested for their ability to mediate ADCC of OX40 expressing target cells by human natural killer cells.

A non-radioactive cytotoxicity assay was used to determine the percent specific lysis of the target cells following a four hour incubation with the human anti-human OX40 antibodies and human natural killer cells at a ratio of twenty effector cells to one target cell (FIG. 10). EL4-human OX40 target cells were labeled with 0.001-10 μg/ml of anti-OX40 or negative control antibodies then incubated with human natural killer cells. Lysis of the target cells was determined by release of lactose dehydrogenase in a non-radioactive cytotoxicity assay. The percent specific lysis was determined as described in the methods. The human IgG1 anti-human OX40 antibodies induced ADCC of EL4-human OX40 target cells in a dose dependent manner. The human IgG4 anti-OX40 antibodies and a control human IgG1 antibody did not induce specific lysis of the target cells. The level of ADCC activity correlates with the relative binding affinity and the epitope group as those antibodies in epitope group B (112V8 and 112Y55) both had higher ADCC activity than antibodies in groups A (112F32) and C (112Z5).

The results of the analyses described here identify antibodies with a range of binding affinities, three different epitopes, and demonstration of their efficacy in blocking OX40 ligand binding, and preventing or ameliorating T cell mediated inflammatory reactions. The ability of these human anti-human OX40 antibodies (112F32, 112V8, 112Y55, 112Y131, and 112Z5) to reduce proliferation, disease progression and inflammatory cytokine production demonstrates the potential of direct blockade of OX40 as an approach for treatment of T cell mediated inflammatory or autoimmune diseases, including but not limited to rheumatoid arthritis, multiple sclerosis, psoriasis, Crohn's disease, graft versus host disease, and transplantation rejection. Depleting activity of the anti-OX40 antibodies is not necessary for reduction in proliferation or amelioration of disease, which may reduce potential adverse effects due to T cell depletion.

BIBLIOGRAPHY

Akiba, H., Y. Miyahira, et al. (2000). "Critical contribution of OX40 ligand to T helper cell type 2 differentiation in experimental leishmaniasis." *J Exp Med* 191(2): 375-80.

Al-Shamkhani, A., S. Mallett, et al. (1997). "Affinity and kinetics of the interaction between soluble trimeric OX40 ligand, a member of the tumor necrosis factor superfamily, and its receptor OX40 on activated T cells." *J Biol Chem* 272(8): 5275-82.

Alegre, M. L., A. M. Collins, et al. (1992). "Effect of a single amino acid mutation on the activating and immunosuppressive properties of a "humanized" OKT3 monoclonal antibody." *J Immunol* 148(11): 3461-8.

Angal, S., D. J. King, et al. (1993). "A single amino acid substitution abolishes the heterogeneity of chimeric mouse/human (IgG4) antibody." *Mol Immunol* 30(1): 105-8.

Bachmann, M. F., M. Barner, et al. (1999). "CD2 sets quantitative thresholds in T cell activation." *J Exp Med* 190(10): 1383-92.

Bansal-Pakala, P., A. G. Jember, et al. (2001). "Signaling through OX40 (CD134) breaks peripheral T-cell tolerance." *Nat Med* 7(8): 907-12.

Baum, P. R., R. B. Gayle, 3rd, et al. (1994). "Molecular characterization of murine and human OX40/OX40 ligand systems: identification of a human OX40 ligand as the HTLV-1-regulated protein gp34." *Embo J* 13(17): 3992-4001.

Baum, P. R., R. B. Gayle, 3rd, et al. (1994). "Identification of OX40 ligand and preliminary characterization of its activities on OX40 receptor." *Circ Shock* 44(1): 30-4.

Blazar, B. R., A. H. Sharpe, et al. (2003). "Ligation of OX40 (CD134) regulates graft-versus-host disease (GVHD) and graft rejection in allogeneic bone marrow transplant recipients." *Blood* 101(9): 3741-8.

Brocker, T., A. Gulbranson-Judge, et al. (1999). "CD4 T cell traffic control: in vivo evidence that ligation of OX40 on CD4 T cells by OX40-ligand expressed on dendritic cells leads to the accumulation of CD4 T cells in B follicles." *Eur J Immunol* 29(5): 1610-6.

Brugnoni, D., A. Bettinardi, et al. (1998). "CD134/OX40 expression by synovial fluid CD4+ T lymphocytes in chronic synovitis." *Br J Rheumatol* 37(5): 584-5.

Brunhouse, R. and J. J. Cebra (1979). "Isotypes of IgG: comparison of the primary structures of three pairs of isotypes which differ in their ability to activate complement." *Mol Immunol* 16(11): 907-17.

Calderhead, D. M., J. E. Buhlmann, et al. (1993). "Cloning of mouse Ox40: a T cell activation marker that may mediate T-B cell interactions." *J Immunol* 151(10): 5261-71.

Cheung, T. C., I. R. Humphreys, et al. (2005). "Evolutionarily divergent herpesviruses modulate T cell activation by targeting the herpesvirus entry mediator cosignaling pathway." *Proc Natl Acad Sci USA* 102(37): 13218-23.

Compaan, D. M., L. C. Gonzalez, et al. (2005). "Attenuating lymphocyte activity: The crystal structure of the btla-hvem complex." *J Biol Chem*.

Croft, M. (2003). "Costimulation of T cells by OX40, 4-1BB, and CD27." *Cytokine Growth Factor Rev* 14(3-4): 265-73.

Croft, M. (2005). "The evolving crosstalk between co-stimulatory and co-inhibitory receptors: HVEM-BTLA." *Trends Immunol* 26(6): 292-4.

Evans, D. E., R. A. Prell, et al. (2001). "Engagement of OX40 enhances antigen-specific CD4(+) T cell mobilization/memory development and humoral immunity: comparison of alphaOX-40 with alphaCTLA-4." *J Immunol* 167(12): 6804-11.

Gadisseur, A. P., J. W. Gratama, et al. (1999). "Expression of T cell activation antigen CD134 (OX40) has no predictive value for the occurrence or response to therapy of acute graft-versus-host disease in partial T cell-depleted bone marrow transplantation." *Bone Marrow Transplant* 23(10): 1013-7.

Gonzalez, L. C., K. M. Loyet, et al. (2005). "A coreceptor interaction between the CD28 and TNF receptor family members B and T lymphocyte attenuator and herpesvirus entry mediator." *Proc Natl Acad Sci USA* 102(4): 1116-21.

Gramaglia, I., A. Jember, et al. (2000). "The OX40 costimulatory receptor determines the development of CD4 memory by regulating primary clonal expansion." *J Immunol* 165(6): 3043-50.

Gramaglia, I., A. D. Weinberg, et al. (1998). "Ox-40 ligand: a potent costimulatory molecule for sustaining primary CD4 T cell responses." *J Immunol* 161(12): 6510-7.

Grewal, I. S. and R. A. Flavell (1998). "CD40 and CD154 in cell-mediated immunity." *Annu Rev Immunol* 16: 111-35.

Higgins, L. M., S. A. McDonald, et al. (1999). "Regulation of T cell activation in vitro and in vivo by targeting the OX40-OX40 ligand interaction: amelioration of ongoing inflammatory bowel disease with an OX40-IgG fusion protein, but not with an OX40 ligand-IgG fusion protein." *J Immunol* 162(1): 486-93.

Huber, H., S. D. Douglas, et al. (1971). "IgG subclass specificity of human monocyte receptor sites." *Nature* 229(5284): 419-20.

Humphreys, I. R., G. Walzl, et al. (2003). "A critical role for OX40 in T cell-mediated immunopathology during lung viral infection." *J Exp Med* 198(8): 1237-42.

Imura, A., T. Hori, et al. (1996). "The human OX40/gp34 system directly mediates adhesion of activated T cells to vascular endothelial cells." *J Exp Med* 183(5): 2185-95.

Imura, A., T. Hori, et al. (1997). "OX40 expressed on fresh leukemic cells from adult T-cell leukemia patients mediates cell adhesion to vascular endothelial cells: implication for the possible involvement of OX40 in leukemic cell infiltration." *Blood* 89(8): 2951-8.

Ishida and Lonberg (2000). 11*th Antibody Engineering Meeting*.

Kabat, e. a. (1991). *Sequences of proteins of immunological interest. Fifth Edition*.

Kaleeba, J. A., H. Offner, et al. (1998). "The OX-40 receptor provides a potent co-stimulatory signal capable of inducing encephalitogenicity in myelin-specific CD4+ T cells." *Int Immunol* 10(4): 453-61.

Kjaergaard, J., J. Tanaka, et al. (2000). "Therapeutic efficacy of OX-40 receptor antibody depends on tumor immunogenicity and anatomic site of tumor growth." *Cancer Res* 60(19): 5514-21.

Kotani, A., T. Ishikawa, et al. (2001). "Correlation of peripheral blood OX40+(CD134+) T cells with chronic graft-versus-host disease in patients who underwent allogeneic hematopoietic stem cell transplantation." *Blood* 98(10): 3162-4.

Kuroiwa, Y., P. Kasinathan, et al. (2002). "Cloned transchromosomic calves producing human immunoglobulin." *Nat Biotechnol* 20(9): 889-94.

Kuroiwa, Y., P. Kasinathan, et al. (2004). "Sequential targeting of the genes encoding immunoglobulin-mu and prion protein in cattle." *Nat Genet* 36(7): 775-80.

Lane, P. (2000). "Role of OX40 signals in coordinating CD4 T cell selection, migration, and cytokine differentiation in T helper (Th)1 and Th2 cells." *J Exp Med* 191(2): 201-6.

Latza, U., H. Durkop, et al. (1994). "The human OX40 homolog: cDNA structure, expression and chromosomal assignment of the ACT35 antigen." *Eur J Immunol* 24(3): 677-83.

Linsley, P. S., W. Brady, et al. (1991). "Binding of the B cell activation antigen B7 to CD28 costimulates T cell proliferation and interleukin 2 mRNA accumulation." *J Exp Med* 173(3): 721-30.

Linton, P. J., B. Bautista, et al. (2003). "Costimulation via OX40L expressed by B cells is sufficient to determine the extent of primary CD4 cell expansion and Th2 cytokine secretion in vivo." *J Exp Med* 197(7): 875-83.

Locksley, R. M., N. Killeen, et al. (2001). "The TNF and TNF receptor superfamilies: integrating mammalian biology." *Cell* 104(4): 487-501.

Lonberg, N. and D. Huszar (1995). "Human antibodies from transgenic mice." *Int Rev Immunol* 13(1): 65-93.

Ma, B. Y., S. A. Mikolajczak, et al. (2005). "The expression and the regulatory role of OX40 and 4-1BB heterodimer in activated human T cells." *Blood* 106(6): 2002-10.

Mallett, S., S. Fossum, et al. (1990). "Characterization of the MRC OX40 antigen of activated CD4 positive T lymphocytes—a molecule related to nerve growth factor receptor." *Embo J* 9(4): 1063-8.

Maxwell, J. R., C. Ruby, et al. (2002). "Contrasting the roles of costimulation and the natural adjuvant lipopolysaccharide during the induction of T cell immunity." *J Immunol* 168(9): 4372-81.

Maxwell, J. R., A. Weinberg, et al. (2000). "Danger and OX40 receptor signaling synergize to enhance memory T cell survival by inhibiting peripheral deletion." *J Immunol* 164(1): 107-12.

Pakala, S. V., P. Bansal-Pakala, et al. (2004). "Prevention of diabetes in NOD mice at a late stage by targeting OX40/OX40 ligand interactions." *Eur J Immunol* 34(11): 3039-46.

Paterson, D. J., W. A. Jefferies, et al. (1987). "Antigens of activated rat T lymphocytes including a molecule of 50,000 Mr detected only on CD4 positive T blasts." *Mol Immunol* 24(12): 1281-90.

Rogers, P. R. and M. Croft (2000). "CD28, Ox-40, LFA-1, and CD4 modulation of Th1/Th2 differentiation is directly dependent on the dose of antigen." *J Immunol* 164(6): 2955-63.

Rogers, P. R., J. Song, et al. (2001). "OX40 promotes Bcl-xL and Bcl-2 expression and is essential for long-term survival of CD4 T cells." *Immunity* 15(3): 445-55.

Salek-Ardakani, S. and M. Croft (2005). "Regulation of CD4 T cell memory by OX40 (CD134)." *Vaccine*.

Sanchez, J., J. Casano, et al. (2004). "Kinetic of regulatory CD25high and activated CD134+ (OX40) T lymphocytes during acute and chronic graft-versus-host disease after allogeneic bone marrow transplantation." *Br J Haematol* 126(5): 697-703.

Sedy, J. R., M. Gavrieli, et al. (2005). "B and T lymphocyte attenuator regulates T cell activation through interaction with herpesvirus entry mediator." *Nat Immunol* 6(1): 90-8.

Seko, Y., N. Takahashi, et al. (1999). "Expression of tumour necrosis factor (TNF) receptor/ligand superfamily co-stimulatory molecules CD40, CD30L, CD27L, and OX40L in murine hearts with chronic ongoing myocarditis caused by coxsackie virus B3." *J Pathol* 188(4): 423-30.

Sharpe, A. H. and G. J. Freeman (2002). "The B7-CD28 superfamily." *Nat Rev Immunol* 2(2): 116-26.

Stuber, E., M. Neurath, et al. (1995). "Cross-linking of OX40 ligand, a member of the TNF/NGF cytokine family, induces proliferation and differentiation in murine splenic B cells." *Immunity* 2(5): 507-21.

Sugamura, K., N. Ishii, et al. (2004). "Therapeutic targeting of the effector T-cell co-stimulatory molecule OX40." *Nat Rev Immunol* 4(6): 420-31.

Takasawa, N., N. Ishii, et al. (2001). "Expression of gp34 (OX40 ligand) and OX40 on human T cell clones." *Jpn J Cancer Res* 92(4): 377-82.

Tanaka, T., F. Kitamura, et al. (1993). "Selective long-term elimination of natural killer cells in vivo by an anti-interleukin 2 receptor beta chain monoclonal antibody in mice." *J Exp Med* 178(3): 1103-7.

Taylor, L., M. Bachler, et al. (2002). "In vitro and in vivo activities of OX40 (CD134)-IgG fusion protein isoforms with different levels of immune-effector functions." *J Leukoc Biol* 72(3): 522-9.

Thompson, C. B., T. Lindsten, et al. (1989). "CD28 activation pathway regulates the production of multiple T-cell-derived lymphokines/cytokines." *Proc Natl Acad Sci USA* 86(4): 1333-7.

Tittle, T. V., A. D. Weinberg, et al. (1997). "Expression of the T-cell activation antigen, OX-40, identifies alloreactive T cells in acute graft-versus-host disease." *Blood* 89(12): 4652-8.

Totsuka, T., T. Kanai, et al. (2003). "Therapeutic effect of anti-OX40L and anti-TNF-alpha MAbs in a murine model of chronic colitis." *Am J Physiol Gastrointest Liver Physiol* 284(4): G595-603.

Tsukada, N., H. Akiba, et al. (2000). "Blockade of CD134 (OX40)-CD134L interaction ameliorates lethal acute graft-versus-host disease in a murine model of allogeneic bone marrow transplantation." *Blood* 95(7): 2434-9.

Ukyo, N., T. Hori, et al. (2003). "Costimulation through OX40 is crucial for induction of an alloreactive human T-cell response." *Immunology* 109(2): 226-31.

Walker, L. S., A. Gulbranson-Judge, et al. (1999). "Compromised OX40 function in CD28-deficient mice is linked with failure to develop CXC chemokine receptor 5-positive CD4 cells and germinal centers." *J Exp Med* 190(8): 1115-22.

Watanabe, T., J. Masuyama, et al. (2006). "CD52 is a novel costimulatory molecule for induction of CD4+ regulatory T cells." *Clin Immunol* 120:247-259.

Weatherill, A. R., J. R. Maxwell, et al. (2001). "OX40 ligation enhances cell cycle turnover of Ag-activated CD4 T cells in vivo." *Cell Immunol* 209(1): 63-75.

Weinberg, A. D. (2002). "OX40: targeted immunotherapy—implications for tempering autoimmunity and enhancing vaccines." *Trends Immunol* 23(2): 102-9.

Weinberg, A. D., M. Lemon, et al. (1996). "OX-40 antibody enhances for autoantigen specific V beta 8.2+ T cells within the spinal cord of Lewis rats with autoimmune encephalomyelitis." *J Neurosci Res* 43(1): 42-9.

Weinberg, A. D., K. W. Wegmann, et al. (1999). "Blocking OX-40/OX-40 ligand interaction in vitro and in vivo leads to decreased T cell function and amelioration of experimental allergic encephalomyelitis." *J Immunol* 162(3): 1818-26.

Zingoni, A., T. Sornasse, et al. (2004). "Cross-talk between activated human NK cells and CD4+ T cells via OX40-OX40 ligand interactions." *J Immunol* 173(6): 3716-24.

WO 95/12673
WO 95/21251

What is claimed:

1. An isolated or purified monoclonal antibody that specifically binds to an epitope in an amino acid sequence OX40 extracellular domain, wherein the antibody comprises all complementarily determining regions (CDRs) of heavy chain variable region sequence in SEQ ID NO:9 and all complementarity determining regions (CDRs) of light chain variable region sequence in SEQ ID NO:10.

2. An isolated or purified monoclonal antibody that specifically binds to an epitope in an amino acid sequence OX40 extracellular domain, wherein the antibody comprises heavy chain and light chain variable region sequences, wherein the heavy chain variable region sequence comprises the mature heavy chain variable region sequence in SEQ ID NO:9.

3. An isolated or purified monoclonal antibody that comprises the mature heavy chain variable region sequence in SEQ ID NO:9 and complementarity determining regions (CDRs) of the chain variable region sequence in SEQ ID NO:10 and specifically binds to an epitope in an amino acid sequence OX40 extracellular domain.

4. An isolated or purified monoclonal antibody that specifically binds to an epitope in an amino acid sequence OX40 extracellular domain, wherein the antibody comprises the mature heavy chain variable region sequence in SEQ ID NO: 9 and mature light chain variable region sequence in SEQ NO:10, or an antigen binding fragment of mature heavy chain variable region sequence in SEQ ID NO:9 and mature light chain variable region sequence in SEQ ID NO:10.

5. A pharmaceutical composition comprising the monoclonal antibody of any of claims 1, 2, 3, or 4, and a pharmaceutically acceptable carrier or excipient.

6. An antigen binding fragment of the antibody of any of claims 1, 2, 3, or 4, wherein the antigen binding fragment is selected from Fab, Fab', F(ab')$_2$, Fv, Fd, single-chain Fvs (scFv), disulfide-linked Fvs (sdFv) and $V_L$ and $V_H$.

7. The monoclonal antibody of any of claims 1, 2, 3, or 4, wherein the OX40 is human.

8. The monoclonal antibody of any of claims 1, 2, 3, or 4, wherein the OX40 comprises a sequence:
MCVGARRLGRGPCAALLLLGLGLSTVTGLHCVGDTYPSNDRCCHECRPGNG MVSRCSRSQNTVCRPCGPGFYNDVVSSKPCKPCTWCNLRSGSERKQLCTATQDTVC RCRAGTQPLDSYKPGVDCAPCPPGHFSPGDNQACKPWTNCTLAGKHTLQPASNSSD AICEDRDPPATQPQETQGPPARPITVQPTEAWPRTSQGPSTRPVEVPGGRAVAAILGL GLVLGLLGPLAILLAIALLYLLRRDQRLPPDAHKPPGGGSFRTPIQEEQADAHSTLAKI (SEQ ID NO:50).

9. The monoclonal antibody of any of claims 1, 2, 3, or 4, wherein the monoclonal antibody is an IgG 1, IgG2, IgG3, IgG4, IgA, IgE, or IgD isotype.

10. The monoclonal antibody of any of claims 1, 2, 3, or 4, wherein the monoclonal antibody reduces or decreases a symptom of graft versus host disease in an acute or chronic xenograft host disease model, or wherein the antibody causes a remission or regression of graft versus host disease in an acute or chronic xenograft host disease model.

11. An isolated or purified monoclonal antibody that specifically binds to an epitope in an amino acid sequence OX40 extracellular domain, wherein the antibody comprises the mature heavy chain variable region sequence in SEQ ID NO:9 and the mature light chain variable region sequence in SEQ ID NO:10.

* * * * *

SEQUENCE LISTING

<160> NUMBER OF SEQ ID NOS: 54

<210> SEQ ID NO 1
<211> LENGTH: 1302
<212> TYPE: DNA
<213> ORGANISM: Homo sapiens

<400> SEQUENCE: 1

```
atgtgcgtgg gggctcggcg gctgggccgc gggccgtgtg cggctctgct cctcctgggc     60
ctggggctga gcaccgtgac ggggctccac tgtgtcgggg acacctaccc cagcaacgac    120
cggtgctgcc acgagtgcag gccaggcaac gggatggtga gccgctgcag ccgctcccag    180
```

```
aacacggtgt gccgtccgtg cgggccgggc ttctacaacg acgtggtcag ctccaagccg    240
tgcaagccct gcacgtggtg taacctcaga agtgggagtg agcggaagca gctgtgcacg    300
gccacacagg acacagtctg ccgctgccgg gcgggcaccc agcccctgga cagctacaag    360
cctggagttg actgtgcccc ctgccctcca gggcacttct ccccaggcga caaccaggcc    420
tgcaagccct ggaccaactg caccttggct gggaagcaca ccctgcagcc ggccagcaat    480
agctcggacg caatctgtga ggacagggac cccccagcca cgcagcccca ggagacccag    540
ggcccccggg ccaggcccat cactgtccag cccactgaag cctggcccag aacctcacag    600
ggaccctcca gatcttgtga caaaactcac acatgcccac cgtgcccagc acctgaactc    660
ctggggggac cgtcagtctt cctcttcccc ccaaaaccca aggacaccct catgatctcc    720
cggacccctg aggtcacatg cgtggtggtg gacgtgagcc acgaagaccc tgaggtcaag    780
ttcaactggt acgtggacgg cgtggaggtg cataatgcca agacaaagcc gcgggaggag    840
cagtacaaca gcacgtaccg tgtggtcagc gtcctcaccg tcctgcacca ggactggctg    900
aatggcaagg agtacaagtg caaggtctcc aacaaagccc tcccagcccc catcgagaaa    960
accatctcca aagccaaagg gcagccccga gaaccacagg tgtacaccct gcccccatcc   1020
cgggatgagc tgaccaagaa ccaggtcagc ctgacctgcc tggtcaaagg cttctatccc   1080
agcgacatcg ccgtggagtg ggagagcaat gggcagccgg agaacaacta caagaccacg   1140
cctcccgtgc tggactccga cggctccttc ttcctctaca gcaagctcac cgtggacaag   1200
agcaggtggc agcaggggaa cgtcttctca tgctccgtga tgcatgaggc tctgcacaac   1260
cactacacgc agaagagcct ctccctgtct ccgggtaaat ga                      1302

<210> SEQ ID NO 2
<211> LENGTH: 433
<212> TYPE: PRT
<213> ORGANISM: Homo sapiens

<400> SEQUENCE: 2

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175
```

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Arg Ser Cys Asp Lys
        195                 200                 205

Thr His Thr Cys Pro Pro Cys Pro Ala Pro Glu Leu Leu Gly Gly Pro
    210                 215                 220

Ser Val Phe Leu Phe Pro Pro Lys Pro Lys Asp Thr Leu Met Ile Ser
225                 230                 235                 240

Arg Thr Pro Glu Val Thr Cys Val Val Val Asp Val Ser His Glu Asp
                245                 250                 255

Pro Glu Val Lys Phe Asn Trp Tyr Val Asp Gly Val Glu Val His Asn
            260                 265                 270

Ala Lys Thr Lys Pro Arg Glu Glu Gln Tyr Asn Ser Thr Tyr Arg Val
        275                 280                 285

Val Ser Val Leu Thr Val Leu His Gln Asp Trp Leu Asn Gly Lys Glu
    290                 295                 300

Tyr Lys Cys Lys Val Ser Asn Lys Ala Leu Pro Ala Pro Ile Glu Lys
305                 310                 315                 320

Thr Ile Ser Lys Ala Lys Gly Gln Pro Arg Glu Pro Gln Val Tyr Thr
                325                 330                 335

Leu Pro Pro Ser Arg Asp Glu Leu Thr Lys Asn Gln Val Ser Leu Thr
            340                 345                 350

Cys Leu Val Lys Gly Phe Tyr Pro Ser Asp Ile Ala Val Glu Trp Glu
        355                 360                 365

Ser Asn Gly Gln Pro Glu Asn Asn Tyr Lys Thr Thr Pro Pro Val Leu
    370                 375                 380

Asp Ser Asp Gly Ser Phe Phe Leu Tyr Ser Lys Leu Thr Val Asp Lys
385                 390                 395                 400

Ser Arg Trp Gln Gln Gly Asn Val Phe Ser Cys Ser Val Met His Glu
                405                 410                 415

Ala Leu His Asn His Tyr Thr Gln Lys Ser Leu Ser Leu Ser Pro Gly
            420                 425                 430

Lys

<210> SEQ ID NO 3
<211> LENGTH: 420
<212> TYPE: DNA
<213> ORGANISM: Homo sapiens

<400> SEQUENCE: 3
atggagtggg ggccgtgctg ggttttcctt gttgttattt tagaaggtgt ccagtgtggg    60
gtgcagctgg tggagtctgg gggaggcttg gtacagcctg gggggtccct gagactctcc   120
tgtgcagcct ctggattcac cttcagtagc tatagcatga actgggtccg ccaggctcca   180
gggaaggggc tggagtgggt ttcatacatt agtagtagta gtagtaccat atactatgca   240
gactctgtga agggccgatt caccatctcc agagacaatg ccaagaactc actgtatctg   300
caaatgaaca gcctgagaga cgaggacacg gctgtgtatt actgtgcgag aggagtgtat   360
cacaatggct ggtccttctt tgactactgg ggccagggaa ccctactcac cgtctcctca   420

<210> SEQ ID NO 4
<211> LENGTH: 390
<212> TYPE: DNA
<213> ORGANISM: Homo sapiens

<400> SEQUENCE: 4

```
atggacatga gggtcctcgc tcagctcctg gggctcctgc tgctctgttt cccaggtgcc    60
agatgtgaca tccagatgac ccagtcccca tcctcactgt ctgcatctgt aggaaacaga   120
gtcaccatta cttgtcgggc gagtcaggat attagcagct ggttagcctg gtatcagcag   180
aaaccagaga aagcccctaa gtccctgatc tatgctgcat ccagtttgca aagtggggtc   240
ccatcaaggt tcagcggcag tggatctggg acagatttca ctctcaccat cagcagcctg   300
cagcctgaag attttgcaac ttattactgc caacagtata atagttaccc cctcaccttc   360
ggccaaggga cacgactgga gattaaacga                                     390

<210> SEQ ID NO 5
<211> LENGTH: 423
<212> TYPE: DNA
<213> ORGANISM: Homo sapiens

<400> SEQUENCE: 5
atggacacac tttgctccac gctcctgctg ctgaccatcc cttcatgggt cttgtcccag    60
atcaccttga aggagtctgg tcctacgcta gtgaagccca acagaccct cacgctgacc   120 tgcaccttct ctggattctc actcagcact agtggaatgg gtgtgggctg gatccgtcag   180
cccccaggaa aggccctgga gtggcttgca gtcatttatt gggatgatca tcaactctac   240
agtccatctc tgaagagcag gctcaccatc accaaggaca cctccaaaaa ccaggtggtc   300
cttacaatga ccaacatgga ccctgtggac acagccacat attactgtgc cacagacga   360 ggggccttcc agcactgggg ccagggcacc ctggtcaccg tctcctcagc ttccaccaag   420
ggc                                                                423

<210> SEQ ID NO 6
<211> LENGTH: 387
<212> TYPE: DNA
<213> ORGANISM: Homo sapiens

<400> SEQUENCE: 6
atggaaaccc cagcgcagct tctcttcctc ctgctactct ggctcccaga taccaccgga    60
gaaattgtgt tgacgcagtc tccaggcacc ctgtctttgt ctccagggga aagagccacc   120
ctctcctgca gggccagtca gagtgttagc agcagctact tagcctggta ccagcagaaa   180
cctggccagg ctcccaggct cctcatctat ggtgcatcca gcagggccac tggcatccca   240
gacaggttca gtggcagtgg gtctgggaca gacttcactc tcaccatcag cagactggag   300
cctgaagatt ttgcagtgta ttactgtcag cagtatgata gctcgctcac tttcggcgga   360
gggaccaagg tggagatcaa acgaact                                      387

<210> SEQ ID NO 7
<211> LENGTH: 140
<212> TYPE: PRT
<213> ORGANISM: Homo sapiens

<400> SEQUENCE: 7

Met Glu Trp Gly Pro Cys Trp Val Phe Leu Val Val Ile Leu Glu Gly
1               5                   10                  15

Val Gln Cys Gly Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ser Met Asn Trp Val Arg Gln Ala Pro Gly Lys Gly Leu
    50                  55                  60
```

```
Glu Trp Val Ser Tyr Ile Ser Ser Ser Ser Thr Ile Tyr Tyr Ala
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Asp Glu Asp Thr Ala Val
            100                 105                 110

Tyr Tyr Cys Ala Arg Gly Val Tyr His Asn Gly Trp Ser Phe Phe Asp
            115                 120                 125

Tyr Trp Gly Gln Gly Thr Leu Leu Thr Val Ser Ser
            130                 135                 140

<210> SEQ ID NO 8
<211> LENGTH: 130
<212> TYPE: PRT
<213> ORGANISM: Homo sapiens

<400> SEQUENCE: 8

Met Asp Met Arg Val Leu Ala Gln Leu Gly Leu Leu Leu Leu Cys
 1               5                  10                  15

Phe Pro Gly Ala Arg Cys Asp Ile Gln Met Thr Gln Ser Pro Ser Ser
                 20                  25                  30

Leu Ser Ala Ser Val Gly Asn Arg Val Thr Ile Thr Cys Arg Ala Ser
            35                  40                  45

Gln Asp Ile Ser Ser Trp Leu Ala Trp Tyr Gln Gln Lys Pro Glu Lys
 50                  55                  60

Ala Pro Lys Ser Leu Ile Tyr Ala Ala Ser Ser Leu Gln Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
            100                 105                 110

Tyr Asn Ser Tyr Pro Leu Thr Phe Gly Gln Gly Thr Arg Leu Glu Ile
            115                 120                 125

Lys Arg
    130

<210> SEQ ID NO 9
<211> LENGTH: 141
<212> TYPE: PRT
<213> ORGANISM: Homo sapiens

<400> SEQUENCE: 9

Met Asp Thr Leu Cys Ser Thr Leu Leu Leu Thr Ile Pro Ser Trp
 1               5                  10                  15

Val Leu Ser Gln Ile Thr Leu Lys Glu Ser Gly Pro Thr Leu Val Lys
                 20                  25                  30

Pro Lys Gln Thr Leu Thr Leu Thr Cys Thr Phe Ser Gly Phe Ser Leu
            35                  40                  45

Ser Thr Ser Gly Met Gly Val Gly Trp Ile Arg Gln Pro Pro Gly Lys
 50                  55                  60

Ala Leu Glu Trp Leu Ala Val Ile Tyr Trp Asp Asp His Gln Leu Tyr
 65                  70                  75                  80

Ser Pro Ser Leu Lys Ser Arg Leu Thr Ile Thr Lys Asp Thr Ser Lys
                 85                  90                  95

Asn Gln Val Val Leu Thr Met Thr Asn Met Asp Pro Val Asp Thr Ala
            100                 105                 110

Thr Tyr Tyr Cys Ala His Arg Arg Gly Ala Phe Gln His Trp Gly Gln
```

```
            115                 120                 125
Gly Thr Leu Val Thr Val Ser Ser Ala Ser Thr Lys Gly
    130                 135                 140

<210> SEQ ID NO 10
<211> LENGTH: 129
<212> TYPE: PRT
<213> ORGANISM: Homo sapiens

<400> SEQUENCE: 10

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Asp Ser Ser Leu Thr Phe Gly Gly Gly Thr Lys Val Glu Ile Lys Arg
        115                 120                 125

Thr

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctaatacgac tcactatagg gc                                              22

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tcttgtccac cttggtgttg ctgggcttgt g                                    31

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aggcacacaa cagaggcagt tccagatttc                                      30

<210> SEQ ID NO 14
```

-continued

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtaaaacgac ggccagtg                                                 18

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
caggaaacag ctatgac                                                  17

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gagagagaga gctagctgag gagacggtga ccagggt                            37

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agagagagag gtcgaccacc atggacacac tttgctccac g                       41

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agagagagag atctctcacc atggaaaccc cagcgcagct tc                      42

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
agagagagag cgtacgtttg atctccacct tggtccctcc                         40

<210> SEQ ID NO 20
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 20
gctggagggc acggtcacca cgctg                                          25

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gttgaagctc tttgtgacgg gcgagc                                         26

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
accgtgtcga ctggattcca aggcatttcc ac                                  32

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggtgctagct gaggagacgg tgac                                           24

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aatcaagatc tgtcaggaca ca                                             22

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tatcccgtac gtttaatctc cagtcgtgtc                                     30

<210> SEQ ID NO 26
<211> LENGTH: 41
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 26
agagagagag gtcgaccacc atggacacac tttgctccac g                          41

<210> SEQ ID NO 27
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
agagagagag gctagctgaa gagacggtga ccattgt                               37

<210> SEQ ID NO 28
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agagagagag gtcgaccacc atggaaaccc cagcgcagct t                          41

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
agagagagag cgtacgtttg atttccacct tggtcccttg                            40

<210> SEQ ID NO 30
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agagagagag gtcgaccacc atggacacac tttgctccac g                          41

<210> SEQ ID NO 31
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
agagagagag gctagctgaa gagacggtga ccattgt                               37

<210> SEQ ID NO 32
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agagagagag atctctcacc atggaaaccc cagcgcagct tc         42

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
agagagagag cgtacgtttg atttccacct tggtcccctg            40

<210> SEQ ID NO 34
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agagagagag gtcgaccacc atgaccatga ttacgccaag c          41

<210> SEQ ID NO 35
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gagagagaga gctagctgag gagacggtga ccagggt               37

<210> SEQ ID NO 36
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
agagagagag atctctcacc atggaagccc cagctcagct tc         42

<210> SEQ ID NO 37
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
agagagagag cgtacgttta atctccagtc gtgtcccttg            40

<210> SEQ ID NO 38
<211> LENGTH: 408
<212> TYPE: DNA
<213> ORGANISM: Homo sapiens

<400> SEQUENCE: 38
atggacacac tttgctccac gctcctgctg ctgaccatcc cttcatgggt cttgtcccag    60

```
atcaccttga aggagtctgg tcctacgctg gtgaaaccca cacagaccct cacgctgtcc      120
tgcaccttct ctgggttctc actcagcact agtggagtgg gtgtgggctg gatccgtcag      180
cccccaggaa aggccctgga atggcttgca ctcattcatt gggatgatgc tgagcgctac      240
agtccatctc tgaagagcag gctcaccatc accaaggaca cctccaaaaa ccaggtggtc      300
cttacaatga ccaacatgga ccttgtggac acagccacat attactgtgc acacacccgg      360
ggggcttttg atatctgggg ccaagggaca atggtcaccg tctcttca                   408

<210> SEQ ID NO 39
<211> LENGTH: 381
<212> TYPE: DNA
<213> ORGANISM: Homo sapiens

<400> SEQUENCE: 39
atggaaaccc cagcgcagct tctcttcctc ctgctactct ggctcccaga taccaccgga       60
gaaattgtgt tgacgcagtc tccaggcacc ctgtctttgt ctccagggga aagagccatc      120
ctctcctgca gggccagtca gagtgttagc agcagcttct tagcctggta ccaacagaaa      180
cctggccagg ctcccaggct cctcatctat ggtgcattta gcagggccac tggcatccca      240
gacaggttca gtggcagtgg gtctgggaca gacttcactc tcaccatcag cagactggag      300
cctgaagatt ttgcagtgta ttactgtcag cagtatgata gctcacggac gttcggccag      360
gggaccaagg tggaaatcaa a                                                381

<210> SEQ ID NO 40
<211> LENGTH: 408
<212> TYPE: DNA
<213> ORGANISM: Homo sapiens

<400> SEQUENCE: 40
atggacacac tttgctccac gctcctgctg ctgaccatcc cttcatgggt cttgtcccag       60
atcaccttga aggagtctgg tcctacgctg gtgaaaccca cacagaccct cacgctgacc      120
tgcaccttct ctggattctc actcagcact agtggagtgg gtgtgggctg gatccgtcag      180
cccccaggaa aggccctgga gtggcttgca ctcatttatt gggatgatca tagccctac       240 agcccatctc tgaagagcag gctcaccatc accaaggaca cctccaaaaa ccaggtggtc      300
cttacaatga ccaacatgga ccctgtggac acagccacat attactgtgc acgcacccgg      360
ggggcttttg atatctgggg ccaagggaca atggtcaccg tctcttca                   408

<210> SEQ ID NO 41
<211> LENGTH: 401
<212> TYPE: DNA
<213> ORGANISM: Homo sapiens

<400> SEQUENCE: 41
atggaagccc cagcgcagct tctcttcctc ctgctactct ggctcccaga taccaccgga       60
gaaattgtgt tgacacagtc tccagccacc ctgtctttgt ctccagggga aagagccacc      120
ctctcctgca gggccagtca gggtgttagc agctacttag cctggtacca gcagaaacct      180
ggccaggctc ccaggctcct catctatgat gcatccaaca gggccactgg catcccagcc      240
aggttcagtg gcagtgggcc tgggacagac ttcactctca ccatcagcag cctagagcct      300
gaagattttg cagtttatta ctgtcagcag cgtagcaact ggcatccgac gttcggccaa      360
gggaccaagg tggaaatcaa acgaactgtg gctgcaccat c                          401

<210> SEQ ID NO 42
```

<211> LENGTH: 462
<212> TYPE: DNA
<213> ORGANISM: Homo sapiens

<400> SEQUENCE: 42

```
atgaccatga ttacgccaag cttggtaccg agctcggatc cactagtaac ggccgccagt    60
gtgctggaat tcgcccttct aatacgactc actatagggc aagcagtggt atcaacgcag   120
agtacggggg gaggcttggt acagcctggc aggtccctga actctcctg tgcagcctct    180
ggattcaccc ttgatgatta tggcatgcac tgggtccggc aagctccagg aagggcctg    240
gagtgggtct caggtattag ttggaatagt gatagtatag ctatgtgga ctctgtgaag    300
ggccgattca ccatctccag agacaacgcc aagaactccc tgtatctgca aatgaacagt    360
ctgagagttg aggacacggc cttgtattac tgtgtaaaag atattagtgg ctggtacagc    420
tttgactact ggggccaggg aaccctggtc accgtctcct ca                      462
```

<210> SEQ ID NO 43
<211> LENGTH: 381
<212> TYPE: DNA
<213> ORGANISM: Homo sapiens

<400> SEQUENCE: 43

```
atggaagccc cagctcagct tctcttcctc ctgctactct ggctcccaga taccaccgga    60
gaaattgtgt tgacacagtc tccagccacc ctgtctttgt ctccagggga agagccacc    120
ctctcctgca gggccagtca gagtgttagc agctacttag cctggtacca acagaaacct   180
ggccaggctc ccaggctcct catctatgat gcatccaaca gggccactgg catcccagcc   240
aggttcagtg gcagtgggtc tgggacagac ttcactctca ccatcagcag cctagagcct   300
gaagattttg cagtttatta ctgtcagcag cgtagcaact ggccgatcac cttcggccaa   360
gggacacgac tggagattaa a                                             381
```

<210> SEQ ID NO 44
<211> LENGTH: 136
<212> TYPE: PRT
<213> ORGANISM: Homo sapiens

<400> SEQUENCE: 44

```
Met Asp Thr Leu Cys Ser Thr Leu Leu Leu Thr Ile Pro Ser Trp
1               5                   10                  15

Val Leu Ser Gln Ile Thr Leu Lys Glu Ser Gly Pro Thr Leu Val Lys
            20                  25                  30

Pro Thr Gln Thr Leu Thr Leu Ser Cys Thr Phe Ser Gly Phe Ser Leu
        35                  40                  45

Ser Thr Ser Gly Val Gly Val Gly Trp Ile Arg Gln Pro Pro Gly Lys
    50                  55                  60

Ala Leu Glu Trp Leu Ala Leu Ile His Trp Asp Asp Ala Glu Arg Tyr
65                  70                  75                  80

Ser Pro Ser Leu Lys Ser Arg Leu Thr Ile Thr Lys Asp Thr Ser Lys
                85                  90                  95

Asn Gln Val Val Leu Thr Met Thr Asn Met Asp Leu Val Asp Thr Ala
            100                 105                 110

Thr Tyr Tyr Cys Ala His Thr Arg Gly Ala Phe Asp Ile Trp Gly Gln
        115                 120                 125

Gly Thr Met Val Thr Val Ser Ser
    130                 135
```

<210> SEQ ID NO 45
<211> LENGTH: 127
<212> TYPE: PRT
<213> ORGANISM: Homo sapiens

<400> SEQUENCE: 45

```
Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Ile Leu Ser Cys Arg Ala Ser Gln Ser
        35                  40                  45

Val Ser Ser Ser Phe Leu Ala Trp Tyr Gln Gln Lys Pro Gly Gln Ala
    50                  55                  60

Pro Arg Leu Leu Ile Tyr Gly Ala Phe Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Asp Ser Ser Arg Thr Phe Gly Gln Gly Thr Lys Val Glu Ile Lys
        115                 120                 125
```

<210> SEQ ID NO 46
<211> LENGTH: 136
<212> TYPE: PRT
<213> ORGANISM: Homo sapiens

<400> SEQUENCE: 46

```
Met Asp Thr Leu Cys Ser Thr Leu Leu Leu Thr Ile Pro Ser Trp
1               5                   10                  15

Val Leu Ser Gln Ile Thr Leu Lys Glu Ser Gly Pro Thr Leu Val Lys
            20                  25                  30

Pro Thr Gln Thr Leu Thr Leu Thr Cys Thr Phe Ser Gly Phe Ser Leu
        35                  40                  45

Ser Thr Ser Gly Val Gly Val Gly Trp Ile Arg Gln Pro Pro Gly Lys
    50                  55                  60

Ala Leu Glu Trp Leu Ala Leu Ile Tyr Trp Asp Asp His Ser Pro Tyr
65                  70                  75                  80

Ser Pro Ser Leu Lys Ser Arg Leu Thr Ile Thr Lys Asp Thr Ser Lys
                85                  90                  95

Asn Gln Val Val Leu Thr Met Thr Asn Met Asp Pro Val Asp Thr Ala
            100                 105                 110

Thr Tyr Tyr Cys Ala Arg Thr Arg Gly Ala Phe Asp Ile Trp Gly Gln
        115                 120                 125

Gly Thr Met Val Thr Val Ser Ser
    130                 135
```

<210> SEQ ID NO 47
<211> LENGTH: 127
<212> TYPE: PRT
<213> ORGANISM: Homo sapiens

<400> SEQUENCE: 47

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30
```

Leu Ser Pro Gly Glu Arg Ala Thr Leu Ser Cys Arg Ala Ser Gln Gly
              35                  40                  45

Val Ser Ser Tyr Leu Ala Trp Tyr Gln Gln Lys Pro Gly Gln Ala Pro
     50                  55                  60

Arg Leu Leu Ile Tyr Asp Ala Ser Asn Arg Ala Thr Gly Ile Pro Ala
 65                  70                  75                  80

Arg Phe Ser Gly Ser Gly Pro Gly Thr Asp Phe Thr Leu Thr Ile Ser
                 85                  90                  95

Ser Leu Glu Pro Glu Asp Phe Ala Val Tyr Tyr Cys Gln Gln Arg Ser
             100                 105                 110

Asn Trp His Pro Thr Phe Gly Gln Gly Thr Lys Val Glu Ile Lys
         115                 120                 125

<210> SEQ ID NO 48
<211> LENGTH: 154
<212> TYPE: PRT
<213> ORGANISM: Homo sapiens

<400> SEQUENCE: 48

Met Thr Met Ile Thr Pro Ser Leu Val Pro Ser Ser Asp Pro Leu Val
 1               5                  10                  15

Thr Ala Ala Ser Val Leu Glu Phe Ala Leu Leu Ile Arg Leu Thr Ile
             20                  25                  30

Gly Gln Ala Val Val Ser Thr Gln Ser Thr Gly Gly Leu Val Gln
             35                  40                  45

Pro Gly Arg Ser Leu Arg Leu Ser Cys Ala Ala Ser Gly Phe Thr Leu
     50                  55                  60

Asp Asp Tyr Gly Met His Trp Val Arg Gln Ala Pro Gly Lys Gly Leu
 65                  70                  75                  80

Glu Trp Val Ser Gly Ile Ser Trp Asn Ser Asp Ser Ile Gly Tyr Val
                 85                  90                  95

Asp Ser Val Lys Gly Arg Phe Thr Ile Ser Arg Asp Asn Ala Lys Asn
             100                 105                 110

Ser Leu Tyr Leu Gln Met Asn Ser Leu Arg Val Glu Asp Thr Ala Leu
         115                 120                 125

Tyr Tyr Cys Val Lys Asp Ile Ser Gly Trp Tyr Ser Phe Asp Tyr Trp
     130                 135                 140

Gly Gln Gly Thr Leu Val Thr Val Ser Ser
145                 150

<210> SEQ ID NO 49
<211> LENGTH: 127
<212> TYPE: PRT
<213> ORGANISM: Homo sapiens

<400> SEQUENCE: 49

Met Glu Ala Pro Ala Gln Leu Leu Phe Leu Leu Leu Trp Leu Pro
 1               5                  10                  15

Asp Thr Thr Gly Glu Ile Val Leu Thr Gln Ser Pro Ala Thr Leu Ser
             20                  25                  30

Leu Ser Pro Gly Glu Arg Ala Thr Leu Ser Cys Arg Ala Ser Gln Ser
              35                  40                  45

Val Ser Ser Tyr Leu Ala Trp Tyr Gln Gln Lys Pro Gly Gln Ala Pro
     50                  55                  60

Arg Leu Leu Ile Tyr Asp Ala Ser Asn Arg Ala Thr Gly Ile Pro Ala
 65                  70                  75                  80

Arg Phe Ser Gly Ser Gly Ser Gly Thr Asp Phe Thr Leu Thr Ile Ser

Ser Leu Glu Pro Glu Asp Phe Ala Val Tyr Tyr Cys Gln Gln Arg Ser
                85                  90                  95

Asn Trp Pro Ile Thr Phe Gly Gln Gly Thr Arg Leu Glu Ile Lys
            100                 105                 110

115                 120                 125

<210> SEQ ID NO 50
<211> LENGTH: 277
<212> TYPE: PRT
<213> ORGANISM: Homo sapiens

<400> SEQUENCE: 50

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 51
<211> LENGTH: 203
<212> TYPE: PRT
<213> ORGANISM: Homo sapiens

<400> SEQUENCE: 51

Met Cys Val Gly Ala Arg Arg Leu Gly Arg Gly Pro Cys Ala Ala Leu
1               5                   10                  15

```
Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
 50                  55                  60

Arg Pro Cys Gly Pro Gly Phe Tyr Asn Asp Val Val Ser Ser Lys Pro
 65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
            115                 120                 125

Pro Pro Gly His Phe Ser Pro Gly Asp Asn Gln Ala Cys Lys Pro Trp
        130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser
            195                 200

<210> SEQ ID NO 52
<211> LENGTH: 17
<212> TYPE: PRT
<213> ORGANISM: Homo sapiens

<400> SEQUENCE: 52

Arg Pro Ala Gly Pro Gly Phe Tyr Asn Asp Val Val Ser Ser Lys Pro
1               5                   10                  15

Cys

<210> SEQ ID NO 53
<211> LENGTH: 16
<212> TYPE: PRT
<213> ORGANISM: Homo sapiens

<400> SEQUENCE: 53

Arg Ala Gly Thr Gln Pro Leu Asp Ser Tyr Lys Pro Gly Val Asp Cys
1               5                   10                  15

<210> SEQ ID NO 54
<211> LENGTH: 18
<212> TYPE: PRT
<213> ORGANISM: Homo sapiens

<400> SEQUENCE: 54

Leu Ala Gly Lys His Thr Leu Gln Pro Ala Ser Asn Ser Ser Asp Ala
1               5                   10                  15

Ile Cys
```